US011414359B2

United States Patent
McKnight et al.

(10) Patent No.: US 11,414,359 B2
(45) Date of Patent: *Aug. 16, 2022

(54) NITRIFICATION INHIBITORS TO IMPROVE FERTILIZER EFFICIENCY

(71) Applicant: World Source Enterprises, LLC, Charleston (KN)

(72) Inventors: Gary David McKnight, High Point, NC (US); Randall Linwood Rayburn, Burlington, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/985,656

(22) Filed: May 21, 2018

(65) Prior Publication Data

US 2018/0319716 A1 Nov. 8, 2018

Related U.S. Application Data

(63) Continuation-in-part of application No. 15/967,575, filed on Apr. 30, 2018, now Pat. No. 11,198,652, which is a continuation-in-part of application No. 15/854,319, filed on Dec. 26, 2017, now Pat. No. 10,273,194, which is a continuation-in-part of application No. 15/641,264, filed on Jul. 4, 2017, now abandoned.

(60) Provisional application No. 62/358,116, filed on Jul. 4, 2016.

(51) Int. Cl.
| | | |
|---|---|---|
| C05F 11/08 | (2006.01) | |
| C05G 3/90 | (2020.01) | |
| C05C 9/00 | (2006.01) | |
| C05C 1/00 | (2006.01) | |
| C05C 3/00 | (2006.01) | |
| C07C 251/00 | (2006.01) | |
| C05C 9/02 | (2006.01) | |
| C05C 11/00 | (2006.01) | |
| C05F 3/00 | (2006.01) | |
| C05F 17/00 | (2020.01) | |

(52) U.S. Cl.
CPC .................. *C05G 3/90* (2020.02); *C05C 1/00* (2013.01); *C05C 3/00* (2013.01); *C05C 9/00* (2013.01); *C05C 9/02* (2013.01); *C05C 11/00* (2013.01); *C05F 3/00* (2013.01); *C05F 11/08* (2013.01); *C05F 17/00* (2013.01); *C07C 251/00* (2013.01)

(58) Field of Classification Search
None
See application file for complete search history.

(56) References Cited

U.S. PATENT DOCUMENTS

| | | | | |
|---|---|---|---|---|
| 2016/0060184 A1* | 3/2016 | Gabrielson | .............. | C05G 3/08 71/30 |
| 2016/0168041 A1* | 6/2016 | McKnight | ................ | C05D 9/00 71/21 |
| 2016/0355445 A1* | 12/2016 | Bobeck | ................ | C05G 3/0064 |
| 2017/0313631 A1* | 11/2017 | Nave | .......................... | C05C 3/00 |

* cited by examiner

*Primary Examiner* — Wayne A Langel
(74) *Attorney, Agent, or Firm* — BenSchroeder Law, PLLC

(57) ABSTRACT

Disclosed are compositions and methods of making a liquid fertilizer additive of biodegradable polymeric and/or oligomeric nitrification inhibitors comprised of utilizing a non-aqueous polar, aprotic organo liquid (NAPAOL) as the reaction medium for the reaction of aldehyde(s) with cyano-containing nitrification inhibitors that have one or more aldehyde reactive groups selected from the group consisting of a) primary, b) secondary amines, c) amides, d) thiols, e) hydroxyls and f) phenols.

20 Claims, 12 Drawing Sheets

(Example 79)

NITRIFICATION INHIBITORS TO IMPROVE FERTILIZER EFFICIENCY

The present invention claims priority under 35 USC 120 and is a continuation in part of U.S. application Ser. No. 15/967,575 filed Apr. 30, 2018, which is a continuation in part of U.S. application Ser. No. 15/854,319 filed Dec. 26, 2017, which in turn claims priority under 35 USC 120 to U.S. application Ser. No. 15/641,264 filed Jul. 4, 2017, which in turn claims priority under 35 USC 119 to U.S. Provisional Application No. 62/358,116 filed Jul. 4, 2016, the entire contents of all of which are incorporated by reference in their entireties.

FIELD OF THE INVENTION

In embodiments, the present invention relates to liquid formulations comprising nitrification inhibitors chemically bound within a polymer/oligomer, dispersed within a Non-aqueous Organic Solvent Delivery System (abbreviated as NOSDS) for application to nitrogen sources. The method of making these polymeric and/or oligomeric nitrification inhibitors comprise a non-aqueous polar, aprotic organo liquid (abbreviated as NAPAOL) that is utilized as the reaction medium for the reaction of aldehyde(s) with cyano-containing nitrification inhibitors that have one or more aldehyde reactive groups selected from the group consisting of a) primary, b) secondary amines, c) amides, d) thiols, e) hydroxyls and f) phenols and wherein the process parameters are optimized for conserving the cyano group. A non-aqueous solvent delivery system (NOSDS) can be utilized to improve the physical properties of the liquid formulation wherein the NOSDS comprises the reaction medium, NAPAOL, aprotic solvents and protic solvents which are environmentally friendly, have flashpoints above 145° F. and are inherently rated safe for contact with humans and animals.

In embodiments, the present invention relates to liquid formulations containing hydrophobic, biodegradable polymers dispersed within a Non-aqueous Organic Solvent Delivery System (NOSDS) and is designed to coat fertilizer granules with a hydrophobic film utilizing simple application equipment such as mixers, blenders and tumblers. This film can impede the dissolution of fertilizer components by water improving fertilizer efficiency. The NOSDS can be aprotic solvents, protic solvents and mixtures of protic and aprotic solvents which are environmentally friendly, have flashpoints above 145° F., and are inherently rated safe for contact with humans and animals. The hydrophobic polymers are the reaction product of aldehyde(s) and nitrogen containing compounds.

BACKGROUND OF THE INVENTION

Fertilizer efficiency has become a major issue in the world. The major element of fertilizer is nitrogen (N). In one study, using data from over 800 experiments, it was estimated that only 51% of the N applied was recovered by cereals plant (Dobermann and Cassman 2005). In another study, it was reported that average N recovery in cereals in China was 30-35% (Fan 2004). Phosphorous is the second largest element in fertilizer compositions and its efficiency is even lower. It was estimated to be around 10-25% (Unsay 1979). Potassium is the third largest fertilizer composition and its efficiency is around 40% (Baligar V C 1986).

One of the main factors for the low efficiency of fertilizers is due to the excellent water solubility of many of its components. In practice, fertilizers are often just applied once at the beginning of the growing season. After the application, nutrients from fertilizers are dissolved in water and released to soil in amounts that are too much for plants to absorb. The unabsorbed nutrients can be leached to the environment, and find their way to surface water such as ponds, lakes and rivers or continue to leach into the subsurface water table contaminating many of the rural community water supplies. Low efficiency of fertilizer not only increases the cost of fertilization, but also contributes significantly to environmental pollution. In the case of nitrogen based fertilizers, one of the major mechanisms for its poor efficiency is the impact of biologically driven processes on water solubilized sources of nitrogen. Urea is the main component of most nitrogen fertilizers. In the presence of soil moisture, natural or synthetic ureas are dissolved and are converted to ammonium ion by bacterial activity, making the nitrogen available for plant uptake. Ammonium can be further converted by bacteria in soil to nitrate through a process called nitrification. Nitrate is also available for plant uptake. Excess ammonia not absorbed by plants can leach into water which can be toxic to water creatures (US EPA822-R-13-001). Excess nitrates can also leach into water, causing the increasing of nitrate concentration in the ground water. Consumption of nitrate contaminated water by human can cause methemoglobinemia (blue baby syndrome) (Kross, Hallberg et al. 1993). Moreover, excessive nitrate can be converted into nitric oxide or nitrous oxide by certain types of bacteria in the soil, through a biological process called denitrification. Nitrous oxide is a potent greenhouse gas, whose potency on global warming is 300 times stronger than carbon dioxide (http://epa.gov/climatechange/ghgemissions/gases/n2o.html). In the case of phosphate fertilizer, phosphate fertilizer in the soil can be eroded into the river causing eutrophication, which can pose severe damage to the whole water body (Bennett EM 2001). Over usage of potassium fertilizer has been associated with deterioration of soil structure, The other problem associated with the over usage of potassium fertilizer is the disruption of the balance of nutrients in the soil such as Ca, Fe and Zn, that are in a plant available form (S 2012).

The goal of the worldwide agricultural industry is to increase the efficiency and decrease the environmental impact of fertilizer. One method is to apply the fertilizer in small doses but with more frequency. However, this approach will incur increased labor cost and is not economically practical, especially in developed countries, where the labor cost tends to be higher. A preferred method is to slow down the dissolution of water soluble fertilizer components and extend the period of time for release of nutrients in a plant available form. The current technological trend for slowing dissolution of fertilizer is focused on inventions that utilize various types of coatings which control water's access to the fertilizer's water soluble components. While many inventions claim the ability to coat any of the fertilizer components, the major commercialized coating-based products are centered around urea. To implement these inventions usually require separate process steps, heat and specialized application equipment for application of coatings to fertilizer. The choice of coating urea is based on (1) Urea is usually produced through a synthetic process making the additional steps of coating conveniently part of the overall urea preparation process, (2) urea is one of the more costly as well as one of the largest components in a fertilizer formulation and (3) urea bonds well with most organic coatings versus the inorganic nature of the other components of fertilizer. The core of the technology is that coating urea prills (granules) with a water-insoluble, semipermeable, or impermeable (with pores) material delays the release of N from the urea. Urea is highly soluble in water, but the solubility of coated urea is dependent on the coating material, its thickness, and the coverage and uniformity of the coating on the granule.

The first widely used urea coating technology is a sulfur coating in U.S. Pat. No. 3,342,577 (Blauin) which demonstrates a process of sulfur coating of urea particles to slow dissolution. It was developed in the late 1960's by the Tennessee Valley Authority (TVA) as an economical system for reducing the rate of dissolution when urea particles are applied to the soil as fertilizer. The release of nutrients from sulfur-coated fertilizers occurs by diffusion of water through imperfections in the sulfur coating and through coating breakdown. In this technology, urea is coated with molten sulfur. It is sometimes topped with a coating of wax to overcome the numerous granule surface imperfections as well as to mitigate damage to the coating through processing, packaging, storage and transport of the coated urea. Sulfur is water impermeable, but the cracks on the surface allow water to penetrate in the beginning. Overtime, sulfur is degraded by bacteria in the soil and urea is totally released (Christians 2004).

U.S. Pat. No. 4,551,166—(Behnke) discloses that the addition of dicyandiamide (DCD) can be carried out at several points in the urea-formaldehyde condensation reaction and utilize water as the reaction medium. DCD can either be added right at the beginning of the reaction, together with the urea and the formalin, or later during the reaction or at the end of the reaction, before or after cooling. Benke also discloses that the methylene bisurea analogue, methylene bisdicyandiamide, is not formed during the reaction.

Attempts to seal the sulfur coating have been described in U.S. Pat. No. 5,219,465 (Goertz), by utilizing a polymethylene poly(phenyl-isocyanate), a catalyst to promote polyurethane curing with polyester polyols to topcoat the sulfur on the surface. U.S. Pat. No. 5,599,374 (Detrick) relates to a process for producing sulfur-coated, slow release fertilizers having a uniform, durable polymeric coating over the sulfur-coating which improves impact and abrasion resistance properties. This polymer coating is formed by the direct in situ co-polymerization of diethylene glycol-triethanolamine polyol and a diisocyanate on the surface of the sulfur-coated urea granule.

U.S. Pat. No. 5,653,782 (Stern et. al.) describes a process by which fertilizer particles are preheated to a temperature in excess of the melting point of sulfur (115° C.), prior to being mixed with solid sulfur prills. The resulting fertilizer is comprised of fertilizer particles contained in a sulfur matrix.

U.S. Pat. No. 6,338,746 (Detrick et al.) describes a process of first coating a fertilizer with a polymer, then coating the polymer with sulfur and thereafter applying a polymer coating.

U.S. Pat. Application, 20100011825 (Ogle, et al.) teaches that multiple layers of coating for urea granules in which the urea is coated with a polymeric layer, an intermediate layer and sulfur layer outside.

While sulfur represents a low cost coating, it still required separate manufacturing steps, high temperatures (>120 C) and is not attrition resistant during processing, packaging, storage and transporting without the addition of other additives.

Urethane polymer technologies have also been developed to coat urea fertilizer, which allows more precise rate of nitrogen release than sulfur coated urea. U.S. Pat. No. 3,264,089 (Hansen) and U.S. Pat. No. 3,475,154 (Kato) inventions involve preformed polymers in quick drying solvents. As these solvents are flashed off, their fumes create a low flash point hazard and can result in pinhole imperfections on the coated fertilizer. Isocyanate based polymers are utilized in a number of inventions which are based on a plurality of coatings in which a urethane polymer is formed on the surface of a fertilizer particle through separate coating of an isocyanate capable of crosslinking with compounds having multiple active hydrogens such as polyols or polyamine. Most inventions also include a final coating that is hard but not brittle to improve resistance to damage to the coatings during processing, packaging, storage and transport.

U.S. Pat. No. 5,538,531 (Hudson et al.) describes controlled release fertilizers and a method for their production. These controlled release fertilizers have a central mass of particulate fertilizer which contains at least one water soluble plant nutrient surrounded by a plurality of coatings. The inner coating comprises the reaction product of an aromatic, a polyol having from 2 to 6 hydroxyl units and at least one alkyl moiety containing from about 10 to 22 carbon atoms. An outer coating of a wax is also necessary.

U.S. Pat. No. 5,803,946 (Petcavich, et al.), teaches a urea particulate plant nutrient having on its surface an interpenetrating polymer network comprising a biuret, a urethane and tung oil.

U.S. Pat. No. 6,663,686 (Geiger et al.) teaches a process in which wax is used as a component of the polyurethane coating, not as a separate over-coat. The invention describes controlled release can be achieved with less coating materials and by a relatively simple procedure which in turn, permits the reduction of coat thickness.

U.S. Pat. Application, 20040016276 (Wynnyk, et al.), utilizes an isocyanate and castor oil to build a urethane polymer for control release of the water soluble components of fertilizer and incorporates an inorganic and/or an organic particulate filler and, optionally, a wax in a one-step coating process. The addition of the particulate filler is touted as improving processing, handling, packaging and transport.

While many of these inventions have been shown to slow down the dissolution of urea, the processes, equipment and chemistries result in a coated urea that is very expensive when compared to uncoated urea and is mainly used for expensive crops and turf industry (LAL 1998). Many of these coatings also provide no nutritional value for plants.

Although the listed inventions claim to provide a coating to limit dissolution of other fertilizers components such as phosphorus, potassium and micronutrients, the cost of the application of such technologies has impaired their entry into the agricultural marketplace. While many of the coating technologies have strategies to overcome the attrition of coverage of the urea particle, the inorganic nature of the other fertilizer components causes difficulties in the adhesion of the coatings to the inorganic particles. Natural based fertilizers such as manure are also not coated due to the cost of the coating operations, the quick loss of nitrogen value due to existing bacteria population and manure's amorphous physical nature.

Patent CN104803807 (Yuan) teaches us that urea, ammonium phosphate, potassium chloride, diammonium phosphate, monoammonium phosphate, potassium nitrate, potassium dihydrogen phosphate, magnesium humate, zinc humate, urea ion humate or nitro humic acid granules can be coated with dicyclopentadiene, glycerol ester copolymer, polyvinyl alc., and PMSM (p-methylstryrene-maleic anhydride copolymer).

Patent CN 104609983 (Li, et al.) teaches us that a hydrophobic film is formed on the surface of fertilizer granules by in situ reaction of polymethylene polyphenyl polyisocyanate and polyether polyol.

Patent CN 104446875 (Chen, et al.) teaches us that polycondensation reaction of citric acid, polyglycolic acid and potassium carbonate can form a slow releasing potassium fertilizer.

While all these technologies can slow down the dissolution of water soluble inorganic fertilizer components, the cost of the specialized equipment, chemistries and processing to produce the coated particle and the attrition of the coating coverage during processing, packaging, storage and transport has severely limited their utility for agriculture. Moreover, all these fertilizer must be made according to certain specifications in large volume and cannot be tailored to customer's specific needs. In light of the above, it is desirable to develop a slow release fertilizer coating technology which is environmental-friendly, low cost and can be applied with simple application equipment such as mixers blenders or tumblers. Moreover, this technology should be flexible enough to prepare small batches according to the customer's needs.

U.S. Pat. No. 9,440,890 (Gabrielson) teaches reaction products may be formed from the reaction of formaldehyde, DCD, urea, and an ammonia source in water which may be included in agricultural products, including fertilizer compositions and nitrification inhibitor systems. Gabrielson also states that fertilizer compositions that include the reaction product can be beneficial for reducing leaching of nitrification inhibitors applied to soil. However, the reactions are performed in an aqueous medium which limits their applications to systems or processes not negatively impacted by the presence of water. Gabrielson's invention also requires other formaldehyde reactive constituents such as urea and ammonia which have excellent water solubility to assist with the dissolution of dicyandiamide (DCD) since DCD has a limited solubility in water of approximately 32 grams/liter at 20° C. resulting in slower reactivity and low concentrations of DCD incorporated into the resulting polymers and/or oligomers. The resulting composition of the reaction product is reported to be a mixture of a triazonyl-formaldehyde-DCD adduct, a urea-formaldehyde-DCD adduct, and a DCD-formaldehyde-oligomer adduct.

In fact, the reported composition of the formaldehyde reaction product comprises only about 0.1 to 10 wt. % of a DCD-formaldehyde-oligomer adduct based upon the weight of the nitrification inhibitor system. Since the described invention requires water as a reaction medium and due to research reports that the presence of water is essential in driving the degradation of dicyandiamide to diaminomethylene ureas as shown in the following reaction,

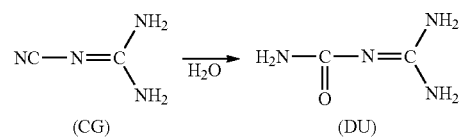

(Ebisuno, Takimoto, Takahashi, Shiba, (1993))

the loss of the cyano-group would diminish the product's nitrification inhibition capabilities either directly or in a slow release mechanism that is dependent on microbial activity to break down the polymer/oligomer releasing dicyandiamide over time.

Gabrielson presents analytical data in Table 7 that utilizes the ionized mass results from a LCMS (liquid chromatograph mass spec) examination of example 2 to derive a few structures of example 2's composition. Example 2 is the reaction products of ammonia, dicyandiamide and urea with formaldehyde, wherein the reaction medium is water. Below in Table 1 is a complete listing of the potential structures for the remaining ionized mass results that were not identified:

TABLE 1

| | LCMS Spectral Peak Identification | |
|---|---|---|
| Peak # | Ionized Mass + Na (23 Da) | Proposed Structure |
| 1 | 148 | 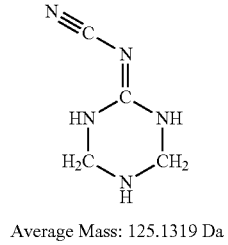<br>Average Mass: 125.1319 Da |
| 2 | | DCD |
| 3 | | Urea |

TABLE 1-continued

LCMS Spectral Peak Identification

| Peak # | Ionized Mass + Na (23 Da) | Proposed Structure |
|---|---|---|
| 4 | 220 | (structure) Average Mass: 197.1978 Da |
| 5 | Unknown/Appears in Nitamin 30L | |
| 6 | Unknown/Appears in Nitamin 30L | |
| 7 | 179 | Urea-Formaldehyde-DCD Average Mass: 156.1459 Da |
| 8 | 251.1 | (structure) Average Mass: 251.2485 Da |
| 9 | 261.1 | (structure) Average Mass: 238.2531 Da |
| 10 | 244.1 | (structure) Average Mass: 132.1212 Da |

TABLE 1-continued

LCMS Spectral Peak Identification

| Peak # | Ionized Mass + Na (23 Da) | Proposed Structure |
|---|---|---|
| 11 | 155.0 Unknown/Appears in Nitamin 30L | Methylene bis Urea<br>Average Mass: 132.1212 Da |
| 12 | 220 | Average Mass: 197.1978 Da |
| 13 | 292.1 | Average Mass: 269.2638 Da<br>or<br>Average Mass: 269.2638 Da |
| 14 | 220 | Average Mass: 197.1978 Da |

TABLE 1-continued

LCMS Spectral Peak Identification

| Peak # | Ionized Mass + Na (23 Da) | Proposed Structure |
|---|---|---|
| 15 | 196.0 | (structure shown) Average Mass: 173.1731 Da |

Upon examination, the data lacks the ionized mass results for methylene bis dicyandiamide (180+23 (Na)=203) and the dicyandiamide-formaldehyde trimer (276+23(Na)=299). It also shows the presence of unreacted DCD. Gabrielson discloses a composition of the formaldehyde reaction product comprises 0.1 to 10 wt. % of a DCD-formaldehyde-oligomer adduct based upon the weight of the nitrification inhibitor system but the analytical data does not indicate the compound to be present.

Gabrielson tests the performance of his innovations as nitrification inhibitors wherein the application levels with urea are based on the DCD content of his examples 1-3. Table 2 show the weight of DCD required for each experiment. Table 2 also translates the weight of DCD utilized in the evaluation into pounds DCD/ton of urea (Standard terminology for Ag Industry).

TABLE 2

| *Level of DCD | Weight of Urea | Weight of nitrogen | Weight of DCD | Lbs DCD/ ton of urea |
|---|---|---|---|---|
| 0.75% | 2.15 | 0.989 | 0.00742 | 6.90 |
| 1.50% | 2.15 | 0.989 | 0.01484 | 13.80 |
| 3.00% | 2.15 | 0.989 | 0.02967 | 27.60 |

*based on nitrogen content of urea
** urea is approximately 46% nitrogen

The expected % DCD content of each example based on the given weights in each examples including the distillation loss of Example 2 was calculated. Table 3 shows the expected weights of each example in the performance experiments as well as translating these weights into pounds/ton of urea (Standard terminology for the Ag Industry)

TABLE 3

| | | 0.75% DCD on N value of urea | | 1.5% DCD on N value of urea | | 3.0% DCD on N value of urea | |
|---|---|---|---|---|---|---|---|
| Example # | Expected % DCD (Bound and free) | grams of Example in 500 ml solution | Lbs of Example/ ton of urea | grams of Example in 500 ml solution | Lbs of Example/ ton of urea | grams of Example in 500 ml solution | Lbs of Example/ ton of urea |
| 1 | 38.36% | 0.0193 | 17.987 | 0.039 | 35.97 | 0.077 | 71.95 |
| 2 | 7.98% | 0.0930 | 86.466 | 0.186 | 172.93 | 0.372 | 345.86 |
| 3 | 18.58% | 0.0399 | 37.137 | 0.080 | 74.27 | 0.160 | 148.55 |

The resulting evaluation on the effectiveness of the nitrification inhibition by the experimental samples showed that example 2 was more effective versus examples 1 and 3 and example #2 was equivalent to C2 (DCD & Urea) but only at the application level of 3% DCD based on the nitrogen content of urea. Example 2 performed poorer versus DCD at lower levels.

Earlier work in U.S. Non-Provisional application Ser. No. 15/641,264 (McKnight) filed Jul. 4, 2017 (to which the present invention claims priority) discussed the use of an aprotic non-aqueous ogano solvent delivery system NOSDS comprising one or more aprotic solvents that can serve as the reaction medium for the formation of biodegradable, hydrophobic polymers that are the reaction product of aldehyde(s) and nitrogen containing compounds. McKnight also detailed a process wherein said biodegradable, hydrophobic polymer involves 1) dissolving the nitrogen containing compound into an aprotic NOSDS at temperatures of 10-140° C. wherein the composition is cooled to 30-60° C. 2) the aldehydes are charged at a rate that controls the exotherm with 5-20° C. of the reaction temperature that is 30-90° C. in a molar ratio of aldehyde to aldehyde reactive sites on the nitrogen containing compound of (0.10-0.90)/1.0. 3) The reaction is held at 30-70° C. and at a pH of 7.5-10.0 for 5 to 12 hours until the free formaldehyde is 40,000 to 5,000 ppm's. 4) The reaction is heated to 70-100° C., the pH is adjusted to 4.0-8.0 and held until free formaldehyde is <700 ppm, wherein the composition is cooled to less than 40° C. and packaged. McKnight also stated that the resulting biodegradable, hydrophobic polymer dispersed within the aprotic NOSDS imparted good water resistant properties to urea. However, it has been determined that the reaction conditions to produce these biodegradable polymers/oligomers were too aggressive for cyano-containing nitrification inhibitors resulting in the conversion of the cyano-group to a carbamide function impacting solubility and most importantly, nitrification inhibition.

Also McKnight demonstrated urea-formaldehyde reactions utilizing dimethyl sulfoxide as the reaction medium in Examples 17 and 18.

Thus, there is a need to for compositions and an improved method of making liquid fertilizer additives of biodegradable polymers and/or oligomers comprised of the reaction products of aldehyde(s) with cyano-containing nitrification inhibitors that have one or more aldehyde reactive groups.

Although the concept of creating a larger molecular weight nitrification inhibitor would assist in slowing its migration through the soil, the industry needs a product that is economical, effective at lower application levels and utilizes a liquid delivery system that is non-aqueous in order to be utilized in all nitrogen source application techniques. It would also be beneficial to have a method to make a modified urea in situ during the urea manufacturing/particle formation processes wherein a liquid fertilizer additive comprising partially reacted/unreacted nitrification inhibitors—aldehyde compositions is added to the molten urea utilizing a non-aqueous polar, aprotic solvent system. Moreover it is beneficial to have urea and ammonia have good solubility in the delivery vehicle. In a variation, the liquid fertilizer additive is added to anhydrous ammonia, a molten pool of urea and/or a molten pool of urea that is either in an ammonia atmosphere, has ammonia dissolved within the molten pool or that has ammonia added during the charge of the liquid fertilizer additive.

SUMMARY OF THE INVENTION

In embodiments, the present invention relates to liquid formulations containing hydrophobic, biodegradable polymers dispersed within a Non-aqueous Organic Solvent Delivery System (NOSDS) and is designed to coat fertilizer granules with a hydrophobic film utilizing simple application equipment such as mixers, blenders and tumblers. This film can impede the dissolution of fertilizer components by water improving fertilizer efficiency. The NOSDS can be aprotic solvents, protic solvents and mixtures of protic and aprotic solvents which are environmentally friendly, have flashpoints above 145° F., and are inherently rated safe for contact with humans and animals. The hydrophobic polymers are the reaction product of aldehyde(s) and nitrogen containing compounds.

In an embodiment, the present invention relates to compositions and an improved method of making liquid fertilizer additives of biodegradable polymers and/or oligomers comprised of the reaction products of aldehyde(s) with cyano-containing nitrification inhibitors that have one or more aldehyde reactive groups selected from the group consisting of a) primary amines, b) secondary amines, c) amides, d) thiols, e) hydroxyls and f) phenols, wherein the cyano-group is conserved.

The present invention also relates to a method of making non-aqueous liquid fertilizer additives that are comprised of high levels of biodegradable polymers and/or oligomers, especially methylene bus nitrification inhibitor (NI) oligomers as shown below:

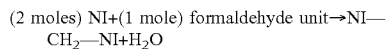

(2 moles) NI+(1 mole) formaldehyde unit→NI—CH$_2$—NI+H$_2$O wherein the reaction of aldehyde(s) with non-cyano- and/or cyano-containing nitrification inhibitors that have one or more aldehyde reactive groups selected from the group consisting of a) primary amines, b) secondary amines, c) amides, d) thiols, e) hydroxyls and f) phenols utilizing a non-aqueous polar, aprotic organo liquid (abbreviated as NAPAOL) as the reaction medium to produce compounds overcoming performance deficiencies related to atmospheric volatility or migration through the soil due to water solubility and low molecular weight. It is thought that these methylene bis NIs as well as polymeric NIs have nitrification inhibition properties as well as providing nitrification inhibition through a slow release mechanism of biodegradation of the oligomer and/or polymer that releases the polymer bound nitrification inhibitor. The utility of a NAPAOL as the reaction medium allows aldehyde reactions with non-cyano-containing nitrification inhibitors that have been previously unavailable due to the poor water solubility of the non-cyano-containing nitrification inhibitors.

The capability of the NAPAOL to also serve as a non-aqueous organo solvent delivery system (abbreviated as NOSDS) allows the application of the liquid composition to nitrogen sources that utilize moisture sensitive application methods. It has been learned that liquid fertilizer additives of biodegradable polymers and/or oligomers comprised of utilizing a non-aqueous polar, aprotic organo liquid (NAPAOL) as the reaction medium for the reaction of aldehyde(s) with cyano-containing nitrification inhibitors that have one or more aldehyde reactive groups selected from the group consisting of a) primary and secondary amines, b) amides, c) thiols, d) hydroxyls and e) phenols assist to conserve the cyano-group. It has also unexpectedly learned that the liquid fertilizer additives of biodegradable polymers and/or oligomers comprised of utilizing a non-aqueous polar, aprotic organo liquid (NAPAOL) as the reaction medium for the reaction of aldehyde(s) with nitrification inhibitors that have one or more aldehyde reactive groups selected from the group consisting of a) primary and secondary amines, b) amides, c) thiols, d) hydroxyls and e) phenols, wherein the resulting product can possesses higher levels of polymer bound and free nitrification inhibitors versus products utilizing a NAPAOL to make solutions of free nitrification inhibitors. In a variation, it has been learned that utilizing a NAPAOL as the reaction medium results in higher compositional weight percent of said biodegradable polymers and/or oligomers versus those produced in an aqueous medium.

In embodiments, the present invention relates to liquid formulations comprising nitrification inhibitors chemically bound within a polymer/oligomer, dispersed within a Non-aqueous Organic Solvent Delivery System (abbreviated as NOSDS) for application to nitrogen sources. The method of making these polymeric and/or oligomeric nitrification inhibitors comprise a non-aqueous polar, aprotic organo liquid (abbreviated as NAPAOL) that is utilized as the reaction medium for the reaction of aldehyde(s) with cyano-containing nitrification inhibitors that have one or more aldehyde reactive groups selected from the group consisting of a) primary, b) secondary amines, c) amides, d) thiols, e) hydroxyls and f) phenols and wherein the process parameters are optimized for conserving the cyano group. A non-aqueous solvent delivery system (NOSDS) can be utilized to improve the physical properties of the liquid formulation wherein the NOSDS comprises the reaction medium, NAPAOL, aprotic solvents and protic solvents which are environmentally friendly, have flashpoints above 145° F. and are inherently rated safe for contact with humans and animals.

DETAILED DESCRIPTION OF THE INVENTION

Figure 1:
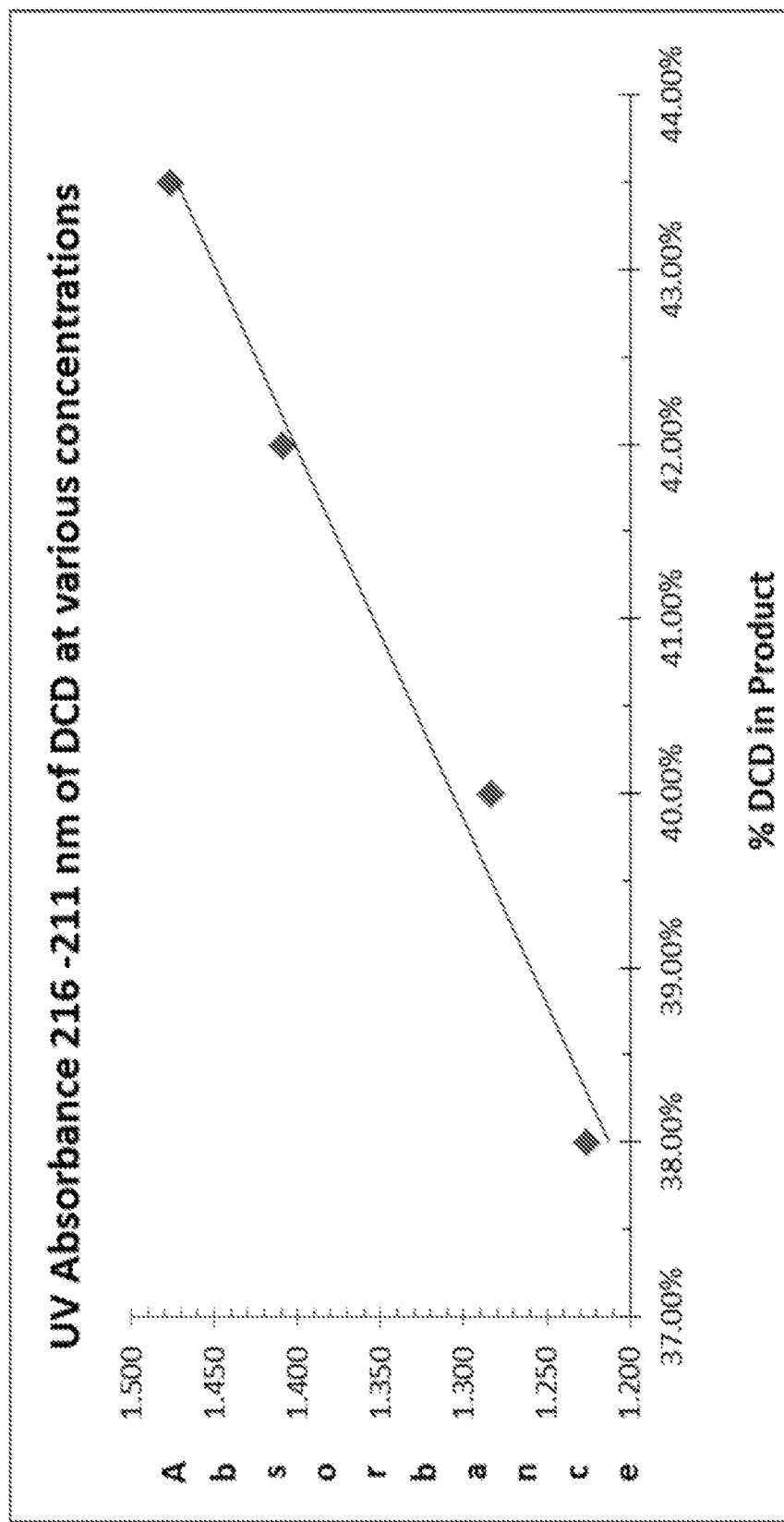
FIG. 1 is the plot of DCD concentration in samples of the present invention versus UV absorbance @211-216 nm.

Definitions:
cyano-containing nitrification inhibitor: nitrogen containing compounds that have nitrification inhibition properties and contain one or more cyano-groups.
non-cyano-containing nitrification inhibitor: nitrogen containing compounds that have nitrification inhibition properties and contain no cyano-groups.
NAPAOL (non-aqueous polar, aprotic organo liquid): an aprotic NOSDS (non-aqueous organo solvent delivery system) that is used specifically as the reaction medium.
biologics: although utilized as bio-active agents are specified as a different category due to their definition as naturally occurring substances, substances produced by natural processes such as fermentation and/or extracts of naturally occurring substances.
nitrogen sources: one or more compounds and/or substances selected from the group consisting of: urea, urea formaldehyde reaction products, ammonia, urea formaldehyde and ammonia reaction products, ammonium nitrate, ammonium sulfate, manure and compost.
treated nitrogen source: a composition comprising a nitrogen source and biologically active agents and/or biologics added either through a coating application or added to the nitrogen source during the nitrogen source's production process either in the melt portion or applied to the nitrogen source during the formation of the nitrogen source's granule.

In one embodiment, the present invention relates to liquid formulations comprised of hydrophobic, biodegradable polymers and a Non-aqueous Organic Solvent Delivery System (NOSDS) and is designed to coat fertilizer granules with a hydrophobic film utilizing simple application equipment such as mixers, blenders and tumblers A NOSDS is comprised of a) one or more protic solvents from the group consisting of: 1) an alcohol from the family of $C_{1-10}$ alkanols, 2) one or more polyols from the group consisting of trimethylol propane, trimethylol ethane, pentaerythritol, sorbitol and sorbitan, glucose, fructose, galactose, and glycerin, 3) poly($C_{1-10}$ alkylene) glycols, 4) one or more alkylene glycols from the group consisting of ethylene glycol, 1,3 propylene glycol, 1,2 propylene glycol, and butylene glycol, 5) isopropylidene glycerol 6) one or more alkylene glycol alkyl ethers represented by the structure:

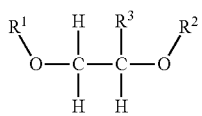

where $R^1$ is: $CH_3$, $C_2H_5$, $C_3H_7$ or $C_4H_9$
where $R^2$ is: H or

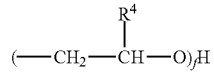

where $R^3$ is: H or $CH_3$
where $R^4$ is H and/or $CH_3$
and f is an integer between 1 and 15
7) one or more alkyl lactates from the group consisting of ethyl, propyl and butyl lactate,
8) one or more alkanolamines represented by the structure:

where $R^5$ is: $C_2H_4OR^8$ or $C_3H_6OH$
where $R^6$ is: H, $C_2H_4OR^8$ or $C_3H_6OH$
where $R^7$ is: H, $C_2H_4OR^8$ or $C_3H_6OH$
where $R^8$ is: $(C_2H_4O)_gH$
and g is an integer between 1-10
and 9) glycerol carbonate.
b) and/or one or more aprotic solvents from the group consisting of 1) dimethyl sulfoxide and/or 2) dialkyl, diaryl, or alkylaryl sulfoxide(s) having the formula:

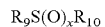

$R_9S(O)_xR_{10}$ wherein $R_9$ and $R_{10}$ are each independently a $C_{1-6}$ alkylene group, an aryl group, or $C_{1-3}$alkylenearyl group or $R_9$ and $R_{10}$ with the sulfur to which they are attached form a 4 to 8 membered ring wherein $R_9$ and $R_{10}$ together are a $C_{1-6}$ alkylene group which optionally contains one or more atoms selected from the group consisting of O, S, Se, Te, N, and P in the ring and x is 1 or 2.
3) one or more alkylene carbonates selected from the group consisting of ethylene carbonate, propylene carbonate and butylene carbonate, 4) one or more polyols capped with acetate or formate wherein the polyol portion selected from the group consisting of ethylene glycol, 1,3 propylene glycol, 1,2 propylene glycol, butylene glycol, trimethylol propane, trimethylol ethane, pentaerythritol, sorbitol and sorbitan, glucose, fructose, galactose and glycerin, 5) one or more alkylene glycol alkyl ethers acetates selected from the group consisting of dipropylene glycol methyl ether acetate, tripropylene glycol methyl ether acetate, and/or tripropylene glycol butyl ether acetate and, 6) isophorone, 7) one or more diesters consisting of dimethylsuccinate, dimethyl adipate, diethyl glutarate, and dimethyl glutarate, 8) dimethylacetamide, 9) dimethylformamide, 10) dimethyl-2-imidazolidinone, 11) 1-Methyl-2-pyrrolidone, 12) hexamethylphosphoramide, 13) 1,2-dimethyloxyethane, 14) 2-methoxyethyl ether, 15)cyclohexylpyrrolidone and 16) limonene.

In one embodiment, the biodegradable, hydrophobic polymers are the reaction product of aldehyde(s) and nitrogen containing compounds. In an embodiment, the aldehyde(s) comprising one or more of the group consisting of:

Q is: O, S

Where $R^{11}$ is: —H, alkyl radical —$C_1H_3$ to —$C_6H_{13}$, —CH=$CH_2$, —$C_4H_3O$, —$C_7H_7$, —$C_6H_5$, —$C_6H_{11}$, CHO, $C_2H_3O$, $C_3H_5O$, $C_4H_7O$, $C_7H_5O$ or —$R^{12}O_2R^{13}$, Where $R^{12}$ is: —C, —$C_2H_2$, —$C_3H_4$, —$C_4H_6$, —$C_5H_8$, —$C_6H_{10}$ Where $R^{13}$ is: —H, $CH_3$, $C_2H_3$, $C_3H_7$, $C_4H_9$ In one embodiment, the nitrogen containing compounds comprising one or more of the group consisting of:

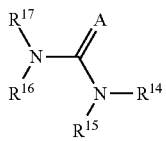

A is: O, S where $R^{14}$ is: —H, alkyl radical —$C_1H_3$ to —$C_6H_{13}$, —$C_6H_5$, —$CONH_2$, —$(CONH)_aNH_2$
Where a is an integer: 1-10 where $R^{15}$ is: —H, alkyl radical —$C_1H_3$ to —$C_6H_{13}$, —$C_6H_5$, —$CONH_2$, —$(CONH)_bNH_2$
Where b is an integer: 1-10 where $R^{16}$ is: —H, alkyl radical —$C_1H_3$ to —$C_6H_{13}$, —$C_6H_5$, —$CONH_2$, —$(CONH)_cNH_2$
Where c is an integer: 1-10 where $R^{17}$ is: —H, alkyl radical —$C_1H_3$ to —$C_6H_{13}$, —$C_6H_5$, —$CONH_2$, —$(CONH)_dNH_2$
Where d is an integer: 1-10 and

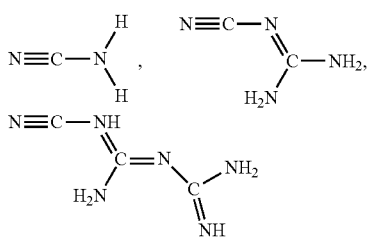

and their tautomeric forms and

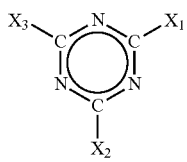

Where $X_1$ is: —$NHR^{18}$, —H, —OH, —$C_6H_5$, —$N(CH_3)_2$, —$CH_3$
Where $R^{18}$ is: H, an alkyl radical —$CH_3$ to —$C_{12}H_{25}$, —$C_2H_4OC_2H_4OH$, $C_2H_4OC_2H_4NH_2$, —$C_3H_6$—$N(CH_3)_2$, $C_2H_4OH$, —$C_6H_5$ Where $X_2$ is: —$NHR^{19}$, —H, —OH, —$C_6H_5$, —$N(CH_3)_2$, —$CH_3$ Where $R^{19}$ is: H, an alkyl radical —$CH_3$ to —$C_{12}H_{25}$, —$C_2H_4OC_2H_4OH$, $C_2H_4OC_2H_4NH_2$, —$C_3H_6$—$N(CH_3)_2$, $C_2H_4OH$, —$C_6H_5$ Where $X_3$ is: —$NHR^{20}$, —H, —OH, —$C_6H_5$, —$N(CH_3)_2$, —$CH_3$ Where $R^{20}$ is: H, an alkyl radical —$CH_3$ to —$C_{12}H_{25}$, —$C_2H_4OC_2H_4OH$, $C_2H_4OC_2H_4NH_2$, —$C_3H_6$—$N(CH_3)_2$, $C_2H_4OH$, —$C_6H_5$ and $NH_2CO$—$R^{21}$ where $R^{21}$ is an alkyl radical CH3 to —$C_{17}H_{35}$ In a variation, an aldehyde can be reacted with a nitrogen containing compound to form a new monomer. A non-limiting example would be the chemical Tetrahydroimidazo[4,5-d]imidazole-2,5(1H,3H)-dione from the reaction of 2 moles of urea and one mole of ethandial and represented by the structure:

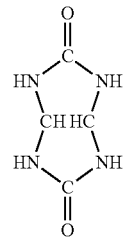

In another variation, the monomeric reaction product of an aldehyde and a nitrogen containing compound can be capped with a $C_1$-$C_4$ alkanol group creating a low temperature crosslinking product.

Non-limiting examples would be 1,3,4,6-Tetrakis(methoxymethyl)glycoluril from the reaction of one mole of Tetrahydroimidazo[4,5-d]imidazole-2,5(1H,3H)-dione with four moles of methanal and then capping with four moles of methanol.

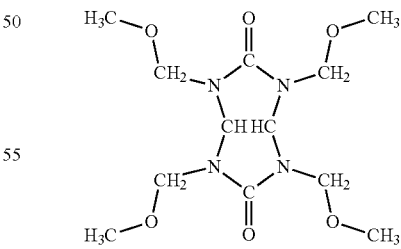

N,N,N',N',N'',N''-Hexakis(methoxymethyl)-1,3,5-triazine-2,4,6-triamine from the reaction of one mole of 1,3,5-triazine-2,4,6-triamine with 6 moles of methanal and then capping with six moles of methanol.

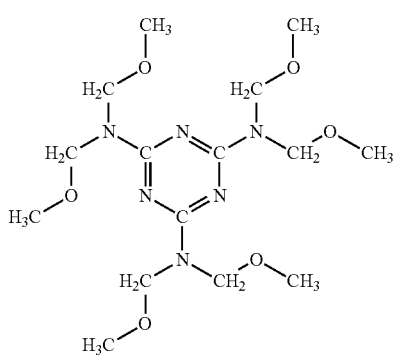

Tetra(methoxymethyl) urea from the reaction of 1 mole of urea with four mole of methanal and then capped with four moles of methanol.

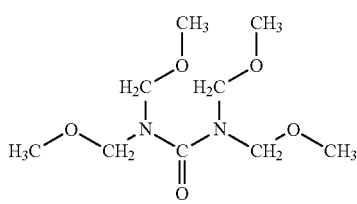

In one embodiment, the biodegradable, hydrophobic polymers that are the reaction product of aldehyde(s) and nitrogen containing compounds contain polyamines such as but not limited to ethylenediamine, diethylenetriamine, triethylenetetramine tetraethylenepentamine and aminoethylethanolamine and/or polyol compounds such as but not limited to one or more polyols from the group consisting of trimethylol propane, trimethylol ethane, pentaerythritol, sorbitol and sorbitan, glucose, fructose, galactose, and glycerin, 3) poly($C_{1-10}$ alkylene) glycols, 4) one or more alkylene glycols from the group consisting of ethylene, 1,3 propylene glycol, 1,2 propylene glycol, and butylene glycol, 5) isopropylidene glycerol 6) one or more alkylene glycol alkyl ethers from the group consisting of tripropylene glycol methyl ether, tripropylene glycol butyl ether, dipropylene glycol butyl ether and tripropylene glycol butyl ether constituting 0.1-5% of its polymer weight in order to modify the coatings' properties such as hydrophobicity, coverage, flexibility of the formed film.

In one embodiment, the biodegradable, hydrophobic polymers that are the reaction product of aldehyde(s) and nitrogen containing compounds contain secondary amines such as diethanolamine, diethylamine, cyclohexylamine, methylethanolamine, diisopropanolamine, methylispropylamine and small molecular weight alcohols such as but not limited to methanol, ethanol, butanol, and hexanol to assist in controlling the molecular weight build of the biodegradable, hydrophobic polymer through chain termination In one embodiment, the biodegradable, hydrophobic polymers are the reaction product of aldehyde(s) and nitrogen containing compounds in which the aldehyde(s) comprising one or more of the group consisting of:
methanal, ethanal, propanal, butanal, pentanal, hexanal, methylethanal, methylpropanal, methylbutanal, phenylacetaldehyde, benzaldehyde, 2-propenal, 3-oxopropanoic, 2-methyl-3-oxopropanoic, 4-oxobutanoic acid, oxoacetic acid, 5-oxopentanoic acid, 6-oxohexanoic acid, 2-oxopropanal, cyclohexanal, furfural methyl esters of 3-oxopropanoic, 2-methyl-3-oxopropanoic acid, 4-oxobutanoic acid, oxoacetic acid, 5-oxopentanoic acid and 6-oxohexanoic acid, ethandial, 1,3-propanedial, butanedial, pentanedial, phthalaldehyde and methanethial
and nitrogen containing compounds comprising one or more of the group consisting of: urea, biuret, polyurea, thiourea, methylurea, dimethylurea, ethylurea, diethylurea, propylurea, dipropylurea, butylurea, dibutylurea, phenylurea, diphenyl urea, pentylurea, dipentylurea, hexyl urea, dihexyl urea, methylthiourea, dimethylthiourea, ethylthiourea, diethylthiourea, propylthiourea, diporpylthiourea, butylthiourea, dibutylthiourea, pentylthiourea, dipentylthiourea, hexylthiourea, dihexylthiourea, phenylthiourea, diphenylthiourea, cyanamide, dicyandiamide, tricyantriamide, melamine, hydroxy oxypentyl melamine, methylaminomelamine, dimethylaminopropylmelamine, 1,3,5-Triazine-2,4,6 triamine, 2,4-diamino-1,3,5-triazine, 2,4-diol-6-Amino-1,3,5-triazine, 2,4-Diamino-6-hydroxy-1,3,5-triazine, 2-Butylamino-4,6-diamino-1,3,5-triazine, 2,4-Diamino-6-methyl-1,3,5-triazine, 2,4-Diamino-6-dimethylamino-1,3,5-triazine, 2-Amino-1,3,5-triazine, ethanamide, propanamide, butanamide, pentanamide, hexanamide, heptanamide, octanamide, nonanamide, decanamide, dodecanamide, tetradecanamide, hexadecanamide, and octadecanamide, ammonia, monoethanolamine, diglycolamine, ethylamine, In one embodiment, the NOSDS of the present invention meet one or more of the following criteria: They are:
environmentally safe;
thermally safe because they have flashpoints above 145° F.;
inherently rated safe for contact with humans and animals;
able to maintain biodegradable, hydrophobic polymers that are the reaction product of aldehyde(s) and nitrogen containing compounds at levels of 1-50% in solution to temperatures down to at least 10° C. This property means that these compositions have improved shelf storage lives.
able to provide improved and even application to fertilizer granules of biodegradable, hydrophobic polymers that are the reaction product of aldehyde(s) and nitrogen containing compounds while not causing clumping of the granules.

In an embodiment, low molecular weight biodegradable, hydrophobic oligomers (LMWBHO) with a molecular weight range of 50-1000 daltons from the reaction of aldehyde(s) and nitrogen containing compounds can be produced utilizing an aprotic NOSDS as the reaction medium. In a variation, the molar ratios of aldehyde groups to aldehyde reactive nitrogens are 0.1-1.5/0.5-1.5. In another variation, these LMWBHOs can be blended with one or more monomeric reaction products of an aldehyde and a nitrogen containing compound that have been alkoxy capped at a % weight ratio of 99.9-90%/0.1-10% of LMWBHO/alkoxy capped monomers. This blend can be applied to the surface of fertilizer granules, then exposed to temperatures 25-100° C. causing crosslinking reaction to occur between the alkoxy capped monomers and the LMWBHO. In a variation, those skilled in the art can add a catalyst such as
methane sulfonic acid, sulfuric acid, para-toluene sulfonic acid. phosphoric acid and methane phosphonic acid
to the coating formulation to improve reactivity and conversion. In a variation, the alkoxy capped monomers comprise one or more of the group consisting of 1,3,4,6-tetrakis (methoxymethyl)glycoluril, N,N,N',N',N'',N''-hexakis(methoxymethyl)-1,3,5-triazine-2,4,6-triamine, tetra(methoxymethyl) urea and di(methoxymethyl) urea. In another variation, an aprotic NOSDS is chosen such as but not limited to DMSO that also solubilizes the surface of urea granules allowing the crosslinking action to include the surface of urea allowing the coating to be chemical bonded to the surface of the urea granule. In a variation, a protic NOSDS can be added to improve the coating properties such as but not limited to viscosity and hydrophobicity.

Additionally, the delivery formulations of the present invention may contain one or more of the following:
  a food coloring or dye that may be used to improve the visual evidence of complete coverage and serve as a visual marker;
  scents or masking agents to improve the odor of the formulations;
  Nonionic, anionic, cationic, zwitterionic, and/or amphoteric surfactants to improve formula application performance of fertilizer granules; and
  Buffering agents.
  Catalyst(s) to improve reaction completion In an embodiment, an aprotic NOSDS comprising of one or more aprotic solvents from the group consisting of 1) Dimethyl Sulfoxide and/or 2) dialkyl, diaryl, or alkylaryl sulfoxide(s) having the formula:

wherein $R_1$ and $R_2$ are each independently a $C_{1-6}$ alkylene group, an aryl group, or $C_{1-3}$alkylenearyl group or $R_1$ and $R_2$ with the sulfur to which they are attached form a 4 to 8 membered ring wherein $R_1$ and $R_2$ together are a $C_{1-6}$ alkylene group which optionally contains one or more atoms selected from the group consisting of O, S, Se, Te, N, and P in the ring and x is 1 or 2.

3) one or more alkylene carbonates selected from the group consisting of ethylene carbonate, propylene carbonate and butylene carbonate, 4) one or more polyols capped with acetate or formate wherein the polyol portion selected from the group consisting of ethylene glycol, 1,3 propylene glycol, 1,2 propylene glycol, butylene glycol, trimethylol propane, trimethylol ethane, pentaerythritol, sorbitol and sorbitan, glucose, fructose, galactose and glycerin, 5) one or more alkylene glycol alkyl ethers acetates selected from the group consisting of dipropylene glycol methyl ether acetate, tripropylene glycol methyl ether acetate, and/or tripropylene glycol butyl ether acetate and, 6) isophorone, 7) one or more diesters consisting of dimethylsuccinate, dimethyl adipate, diethyl glutarate, and dimethyl glutarate, 8) dimethylacetamide, 9) dimethylformamide, 10) dimethyl-2-imidazolidinone, 11) 1-Methyl-2-pyrrolidone, 12) hexamethylphosphoramide, 13) 1,2-dimethyloxyethane, 14) 2-methoxyethyl ether, 15) cyclohexylpyrrolidone and 16) limonene can serve as the reaction medium for the formation of biodegradable, hydrophobic polymers that are the reaction product of aldehyde(s) and nitrogen containing compounds In an embodiment the aldehyde(s) comprise one or more of the group consisting of:

Q is: O, S
Where $R^{11}$ is: —H, alkyl radical —$C_1H_3$ to —$C_6H_{13}$, —CH=$CH_2$, —$C_4H_3O$, —$C_7H_7$, —$C_6H_5$, —$C_6H_{11}$, CHO, $C_2H_3O$, $C_3H_5O$, $C_4H_7O$, $C_7H_5O$ or —$R^{12}O_2R^{13}$,
Where $R^{12}$ is: —C, —$C_2H_2$, —$C_3H_4$, —$C_4H_6$, —$C_5H_8$, —$C_6H_{10}$
Where $R^{13}$ is: —H, $CH_3$, $C_2H_3$, $C_3H_7$, $C_4H_9$
and nitrogen containing compounds comprising one or more of the group consisting of

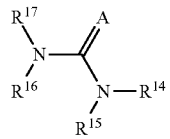

A is: O, S
where $R^{14}$ is: —H, alkyl radical —$C_1H_3$ to —$C_6H_{13}$, —$C_6H_5$, —$CONH_2$, —$(CONH)_aNH_2$
Where a is an integer: 1-10
where $R^{15}$ is: —H, alkyl radical —$C_1H_3$ to —$C_6H_{13}$, —$C_6H_5$, —$CONH_2$, —$(CONH)_bNH_2$
Where b is an integer: 1-10
where $R^{16}$ is: —H, alkyl radical —$C_1H_3$ to —$C_6H_{13}$, —$C_6H_5$, —$CONH_2$, —$(CONH)_cNH_2$
Where c is an integer: 1-10
where $R^{17}$ is: —H, alkyl radical —$C_1H_3$ to —$C_6H_{13}$, —$C_6H_5$, —$CONH_2$, —$(CONH)_dNH_2$
Where d is an integer: 1-10
and

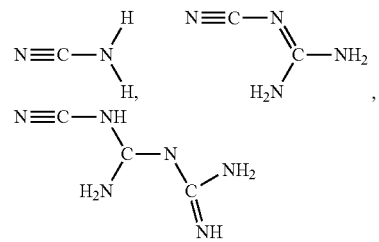

and their tautomeric forms and

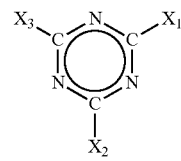

where $X_1$ is: —$NHR^{18}$, —H, —OH, —$C_6H_5$, —$N(CH_3)_2$, —$CH_3$
Where $R^{18}$ is: H, an alkyl radical —$CH_3$ to —$C_{12}H_{25}$, —$C_2H_4OC_2H_4OH$, $C_2H_4OC_2H_4NH_2$, —$C_3H_6$—$N(CH_3)_2$, $C_2H_4OH$, —$C_6H_5$
where $X_2$ is: —$NHR^{19}$, —H, —OH, —$C_6H_5$, —$N(CH_3)_2$, —$CH_3$
Where $R^{19}$ is: H, an alkyl radical —$CH_3$ to —$C_{12}H_{25}$, —$C_2H_4OC_2H_4OH$, $C_2H_4OC_2H_4NH_2$, —$C_3H_6$—$N(CH_3)_2$, $C_2H_4OH$, —$C_6H_5$ where $X_3$ is: $-NHR^{20}$, $-H$, $-OH$, $-C_6H_5$, $-N(CH_3)_2$, $-CH_3$ Where $R^{20}$ is: H, an alkyl radical $-CH_3$ to $-C_{12}H_{25}$, $-C_2H_4OC_2H_4OH$, $C_2H_4OC_2H_4NH_2$, $-C_3H_6-N(CH_3)_2$, $C_2H_4OH$, $-C_6H_5$ and $NH_2CO-R^{21}$ Where $R^{21}$ is an alkyl radical CH3 to $-C17H35$ In a variation, those skilled in the art can add a catalyst such as; methane sulfonic acid, sulfuric acid, para-toluene sulfonic acid. phosphoric acid and methane phosphonic acid to the coating formulation to improve reactivity and conversion. In a variation an aldehyde can be reacted with a nitrogen containing compound within an aprotic NOSDS to form a new monomer. A non-limiting example would be the chemical Tetrahydroimidazo[4,5-d]imidazole-2,5(1H,3H)-dione from the reaction of 2 moles of urea and one mole of ethandialal and represented by the structure:

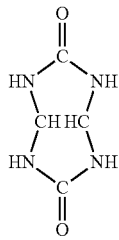

In another variation, the monomeric reaction product of an aldehyde and a nitrogen containing compound can be capped with an $C_1$-$C_4$ alkanol group utilizing an aprotic NOSDS as a reaction medium creating a low temperature crosslinking product.

Non-limiting examples would be 1,3,4,6-Tetrakis(methoxymethyl)glycoluril from the reaction of one mole of Tetrahydroimidazo[4,5-d]imidazole-2,5(1H,3H)-dione with four moles of methanal and then capping with four moles of methanol.

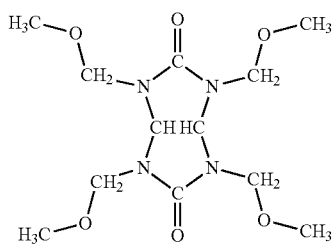

N,N,N',N',N",N"-Hexakis(methoxymethyl)-1,3,5-triazine-2,4,6-triamine from the reaction of one mole of 1,3,5-triazine-2,4,6-triamine with 6 moles of methanal and then capping with six moles of methanol.

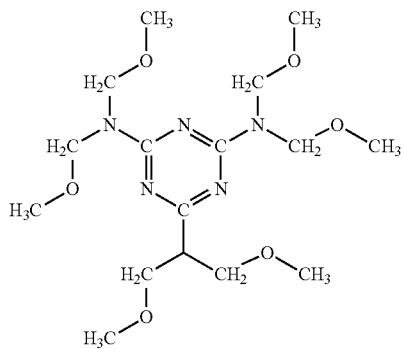

Tetra(methoxymethyl) urea from the reaction of 1 mole of urea with four mole of methanal and then capped with four moles of methanol.

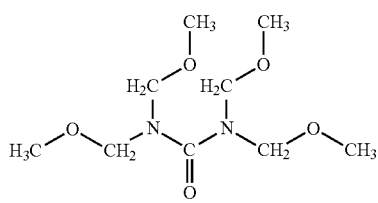

In one embodiment, the biodegradable, hydrophobic polymers that are the reaction product of aldehyde(s) and nitrogen containing compounds formed within an aprotic NOSDS that serves as the reaction medium contains polyamines compounds such as but not limited to ethylenediamine, diethylenetriamine, triethylenetetramine tetraethylenepentamine and aminoethylethanolamine and/or polyol compounds such as but not limited to one or more polyols from the group consisting of trimethylol propane, trimethylol ethane, pentaerythritol, sorbitol and sorbitan, glucose, fructose, galactose, and glycerin, 3) poly($C_{1-10}$ alkylene) glycols, 4) one or more alkylene glycols from the group consisting of ethylene, 1,3 propylene glycol, 1,2 propylene glycol, and butylene glycol, 5) isopropylidene glycerol 6) one or more alkylene glycol alkyl ethers from the group consisting of tripropylene glycol methyl ether, tripropylene glycol butyl ether, dipropylene glycol butyl ether and tripropylene glycol butyl ether constituting 0.1-5% of its polymer weight in order to modify the coatings' properties such as hydrophobicity, coverage, flexibility of the formed film.

In one embodiment, the biodegradable, hydrophobic polymers that are the reaction product of aldehyde(s) and nitrogen containing compounds formed within an aprotic NOSDS that serves as the reaction medium contains secondary amines such as diethylamine, diethanolamine, methylethanolamine, diisopropanolamine, Methylispropylamine and cyclohexylamine and small molecular weight alcohols such as but not limited to methanol, ethanol, butanol hexanol to assist in controlling the molecular weight build of the biodegradable, hydrophobic polymer through chain termination.

In a variation, a protic NOSDS can be added to improve the coating properties such as but not limited to viscosity and hydrophobicity.

Additionally, the delivery formulations of the present invention may contain one or more of the following:

a food coloring or dye that may be used to improve the visual evidence of complete coverage and serve as a visual marker;

scents or masking agents to improve the odor of the formulations;

Nonionic, anionic, cationic, zwitterionic, and/or amphoteric surfactants to improve formula application performance of fertilizer granules; and Buffering agents.

Catalyst(s) to improve reaction completion.

In an embodiment, an aprotic NOSDS comprising of one or more aprotic solvents from the group consisting of 1) Dimethyl Sulfoxide and/or 2) dialkyl, diaryl, or alkylaryl sulfoxide(s) having the formula:

$R_1S(O)xR_2$ wherein $R_1$ and $R_2$ are each independently a $C_{1-6}$ alkylene group, an aryl group, or $C_{1-3}$alkylenearyl group or $R_1$ and $R_2$ with the sulfur to which they are attached form a 4 to 8 membered ring wherein $R_1$ and $R_2$ together are a $C_{1-6}$ alkylene group which optionally contains one or more atoms selected from the group consisting of O, S, Se, Te, N, and P in the ring and x is 1 or 2, 3) one or more alkylene carbonates selected from the group consisting of ethylene carbonate, propylene carbonate and butylene carbonate, 4) one or more polyols capped with acetate or formate wherein the polyol portion selected from the group consisting of ethylene glycol, 1,3 propylene glycol, 1,2 propylene glycol, butylene glycol, trimethylol propane, trimethylol ethane, pentaerythritol, sorbitol and sorbitan, glucose, fructose, galactose and glycerin, 5) one or more alkylene glycol alkyl ethers acetates selected from the group consisting of dipropylene glycol methyl ether acetate, tripropylene glycol methyl ether acetate, and/or tripropylene glycol butyl ether acetate and, 6) isophorone, 7) one or more diesters consisting of dimethylsuccinate, dimethyl adipate, diethyl glutarate, and dimethyl glutarate, 8) dimethylacetamide, 9) dimethylformamide, 10) dimethyl-2-imidazolidinone, 11) 1-Methyl-2-pyrrolidone, 12) hexamethylphosphoramide, 13) 1,2-dimethyloxyethane, 14) 2-methoxyethyl ether, 15) cyclohexylpyrrolidone and 16) limonene.

These can serve as the reaction medium for the formation of biodegradable, hydrophobic polymers that are the reaction product of aldehyde(s) and nitrogen containing compounds with a molecular weight range of 1000-200,000 daltons in a molar ratio of aldehyde groups to aldehyde reactive nitrogens on the nitrogen containing compound of (0.10-0.90)/1.0. The process to make said biodegradable, hydrophobic polymer involves (1) dissolving the nitrogen containing compound into an aprotic NOSDS at temperatures of 10-140° C. wherein the composition is cooled to 30-60° C. 2) the aldehydes are charged at a rate that controls the exotherm with 5-20° C. of the reaction temperature that is 30-90° C. in a molar ratio of aldehyde to aldehyde reactive sites on the nitrogen containing compound of (0.10-0.90)/1.0. 3) The reaction is held at 30-70° C. and at a pH of 7.5-10.0 for 5 to 12 hours until the free formaldehyde is 40,000 to 5,000 ppm's. 4) The reaction is heated to 70-100° C., the pH is adjusted to 4.0-8.0 and held until free formaldehyde is <700 ppm, wherein the composition is cooled to less than 40 C and packaged.

In an embodiment the aldehyde(s) comprise one or more of the group consisting of methanal, ethanal, propanal, butanal, pentanal, hexanal, methylethanal, methylpropanal, methylbutanal, phenylacetaldehyde, benzaldehyde, 2-propenal, 3-oxopropanoic, 2-methyl-3-oxopropanoic acid, 4-oxobutanoic acid, oxoacetic acid, 5-oxopentanoic acid, 6-oxohexanoic acid, 2-oxopropanal, cyclohexanal, furfural, methyl esters of 3-oxopropanoic, 2-methyl-3-oxopropanoic acid, 4-oxobutanoic acid, oxoacetic acid, 5-oxopentanoic acid and 6-oxohexanoic acid, ethandial, 1,3-propanedial, butanedial, pentanedial, phthalaldehyde and methanethial In a variation the aldehydes comprise one or more from the group consisting of the structure:

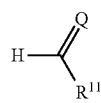

Where Q is: O, S

Where $R^{11}$ is: —H, alkyl radical —$C_1H_3$ to —$C_6H_{13}$, —CH=$CH_2$, —$C_4H_3O$, $C_7H_7$, —$C_6H_5$, —$C_6H_{11}$, CHO, $C_2H_3O$, $C_3H_5O$, $C_4H_7O$, $C_7H_5O$ or —$R^{12}O_2R^{13}$, Where $R^{12}$ is: —C, —$C_2H_2$, —$C_3H_4$, —$C_4H_6$, —$C_5H_8$, —$C_6H_{10}$ Where $R^{13}$ is: —H, $CH_3$, $C_2H_3$, $C_3H_7$, $C_4H_9$ and nitrogen containing compounds comprising one or more of the group consisting of urea, biuret, polyurea, thiourea, methylurea, dimethylurea, ethylurea, diethylurea, propylurea, dipropylurea, butylurea, dibutylurea, phenylurea, diphenyl urea, pentylurea, dipentylurea, hexyl urea, dihexyl urea, methylthiourea, dimethylthiourea, ethylthiourea, diethylthiourea, propylthiourea, diporpylthiourea, butylthiourea, dibutylthiourea, pentylthiourea, dipentylthiourea, hexylthiourea, dihexylthiourea, phenylthiourea, diphenylthiourea, cyanamide, dicyandiamide, tricyantriamide, melamine, hydroxy oxypentyl melamine, methylaminomelamine, dimethylaminopropylmelamine, 1,3,5-Triazine-2,4,6 triamine, 2,4-diamino-1,3,5-triazine, 2,4-diol-6-Amino-1,3,5-triazine, 2,4-Diamino-6-hydroxy-1,3,5-triazine, 2-Butylamino-4,6-diamino-1,3,5-triazine, 2,4-Diamino-6-methyl-1,3,5-triazine, 2,4-Diamino-6-dimethylamino-1,3,5-triazine, 2-Amino-1,3,5-triazine, ethanamide, propanamide, butanamide, pentanamide, hexanamide, heptanamide, octanamide, nonanamide, decanamide, dodecanamide, tetradecanamide, hexadecanamide, and octadecanamide In a variation, the nitrogen containing compounds comprising one or more of the group consisting of the structures:

a)

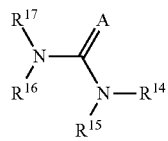

Where A is: O, S

Where $R^{14}$ is: —H, alkyl radical —$C_1H_3$ to —$C_6H_{13}$, —$C_6H_5$, —$CONH_2$, —$(CONH)_aNH_2$ Where a is an integer: 1-10

Where $R^{15}$ is: —H, alkyl radical —$C_1H_3$ to —$C_6H_{13}$, —$C_6H_5$, —$CONH_2$, —$(CONH)_bNH_2$ Where b is an integer: 1-10

Where $R^{16}$ is: —H, alkyl radical —$C_1H_3$ to —$C_6H_{13}$, —$C_6H_5$, —$CONH_2$, —$(CONH)_cNH_2$ Where c is an integer: 1-10
Where $R^{17}$ is: —H, alkyl radical —$C_1H_3$ to —$C_6H_{13}$, —$C_6H_5$, —$CONH_2$, —$(CONH)_dNH_2$
Where d is an integer: 1-10,
b)

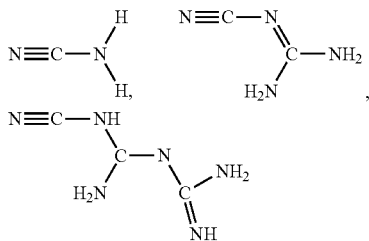

and their tautomeric forms,
c)

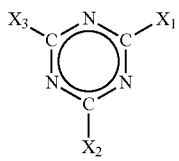

Where $X_1$ is: —$NHR^{18}$, —H, —OH, —$C_6H_5$, —$N(CH_3)_2$, —$CH_3$
Where $R^{18}$ is: H, an alkyl radical —$CH_3$ to —$C_{12}H_{25}$, —$C_2H_4OC_2H_4OH$, $C_2H_4OC_2H_4NH_2$, $C_3H_6$—$N(CH_3)_2$, $C_2H_4OH$, —$C_6H_5$
Where $X_2$ is: —$NHR^{19}$, —H, —OH, —$C_6H_5$, —$N(CH_3)_2$, —$CH_3$
Where $R^{19}$ is: H, an alkyl radical —$CH_3$ to —$C_{12}H_{25}$, —$C_2H_4OC_2H_4OH$, $C_2H_4OC_2H_4NH_2$, —$C_3H_6$—$N(CH_3)_2$, $C_2H_4OH$, —$C_6H_5$
Where $X_3$ is: —$NHR^{20}$, —H, —OH, —$C_6H_5$, —$N(CH_3)_2$, —$CH_3$
Where $R^{20}$ is: H, an alkyl radical —$CH_3$ to —$C_{12}H_{25}$, —$C_2H_4OC_2H_4OH$, $C_2H_4OC_2H_4NH_2$, —$C_3H_6$—$N(CH_3)_2$, $C_2H_4OH$, —$C_6H_5$
and d)
$NH_2CO$—$R^{21}$
Where $R^{21}$ is an alkyl radical $CH_3$ to —$C_{17}H_{35}$ In a variation, a protic NOSDS can be added to improve the coating properties such as but not limited to viscosity and hydrophobicity.

Additionally, the delivery formulations of the present invention may contain one or more of the following:
a food coloring or dye that may be used to improve the visual evidence of complete coverage and serve as a visual marker;
scents or masking agents to improve the odor of the formulations;
Nonionic, anionic, cationic, zwitterionic, and/or amphoteric surfactants to improve formula application performance of fertilizer granules; and
Buffering agents.
Catalyst(s) to improve reaction completion.

In one embodiment, hydrophobic, biodegradable polymers powders are added to the NOSDS under agitation, In a variation, one can aid in the dissolution of the polymer into the NOSDS by using temperatures of 15-140° C.

In another variation one can add a small amount of a surfactant to improve wetting and dispersion of the polymer into the NOSDS. In another variation one can use high shear devices such but not limited to a cowles dissolver, rotor/stator high shear units or a homogenizer to improve the polymer dispersion into NOSDS as well as its physical properties such as viscosity. In another variation one can use any combination of such methods.

In one embodiment one can add a hydrophobic, biodegradable polymer that is dispersed in a liquid into a NOSDS. In a variation if the liquid system does not meet the criteria of NOSDS, it can be displaced with a suitable NOSDS through differential boiling points by temperature and/or reduced pressure.

In one embodiment one skilled in the art can produce a hydrophobic, biodegradable polymer within an aprotic NOSDS. In a variation, the resulting product can be further diluted with a protic NOSDS. In another variation, the resulting product can be further diluted with an aprotic NOSDS. In another variation, the resulting product can be further diluted with a protic and an aprotic NOSDS In an embodiment the NOSDS not only provide the solvating property for the hydrophobic, biodegradable polymer but is also the delivery system for the hydrophobic, biodegradable polymers to the surface of fertilizer granules.

In one embodiment, the liquid formulation containing biodegradable, hydrophobic polymers that are the reaction product of aldehyde(s) and nitrogen containing compounds and NOSDS is used to coat a dry granular fertilizer, which is then applied to cropland and turf. The hydrophobic coating makes the fertilizer more effective in providing nutrients for plant growth over an extended period of time. In a variation, flow modifiers such as but not limited to silicas, powdered lime or a powdered micronutrient salt can be added to the coated fertilizer to improve granules' flow properties.

In one embodiment, coated granular fertilizer products containing additional plant nutrients can be prepared from granular fertilizer, a source or sources of the additional nutrients in powdered form described below. Granular fertilizer can be mixed to distribute the liquid mixture over the granular fertilizer surface using any commonly used equipment to co-mingle a liquid with a granular solid. After distribution of mixture over the granular surface, the additional nutrients in powdered form can be added to the dampened mixture and the resulting combined ingredients can be further mixed to distribute the powdered materials. In an alternate embodiment, the powdered materials may be first mixed with the granular urea and then the solution can be sprayed onto a tumbling bed of the dry ingredients to agglomerate the dry materials. This latter method may be particularly suited to continuous processing. In an embodiment, the formulations use combinations of polar aprotic solvents (sulfoxides, sulfones, dialkyl carbonates) with protic solvents (glycols, triols, and alkanolamines) to produce formulations having acceptable viscosity levels, hydrophobicity and be relatively non-toxic.

In one embodiment, formulations are used to fluidize the biodegradable, hydrophobic polymers that are the reaction product of aldehyde(s) and nitrogen containing compounds and coat the fertilizer granules with a water-resistance layer, which can impede to dissolution of the water soluble components of fertilizer and slow down the leaching of nutrients into soil.

In one embodiment, biodegradable, hydrophobic polymers that are the reaction product of aldehyde(s) and nitrogen containing compounds will degrade in the soil and the degradation product becomes a source of nitrogen fertilizer over time.

The mixing of the materials may be accomplished in a simple mixing tank mixing materials prior to use, using a metering system to inject materials simultaneously, or mixing via a spray injection system.

The mixture can be mixed in any common mixing tank, blenders and tumblers or on a conveyer belt. Although the metering of all ingredients can be based on a weight, it may also be based on a volumetric basis.

A dye or colorant can be added to the mixture to aid in visual assessment of uniform coating during the coating of granular urea. Alternatively, a dye or colorant can be added to the mixture to aid in visual assessment of uniform coating during the coating of urea in aqueous mixtures just prior to application. In one embodiment, the colorant can include any nontoxic common food dye.

EXAMPLES

Example 1

157.43 grams of dicyandiamide is added to 299.4 grams of dimethyl sulfoxide, heated under agitation to 60° C. and held at 60° C. until mixture is clear. The mixture is cooled to 40-45° C. and then 42.17 grams of paraformaldehyde is slowly charged. The batch is held at 45-55° C. for 1.5 hours. The batch is then heated to 60° C. over a one hour period. After 1 hour, 1.0 grams of methane sulfonic acid/70% is charged and batch is slowly heated to 100° C. over a 3 hour period. A vacuum of 40 mm is applied for 30 minutes until distillation ceased, then batch is cooled to <60° C. and off-loaded. Product is clear and viscous.

Example 2

274.12 grams of dicyandiamide is added to 403.03 grams of dimethyl sulfoxide, heated under agitation to 60° C. and held at 60° C. until mixture is clear. 97.91 grams of paraformaldehyde is slowly charged. The batch is held at 60° C. for 9 hours until batch is somewhat clear. The batch is then heated to 80° C. over a one hour period. After 1 hour, 3.72 grams of methane sulfonic acid/70% is charged and batch is slowly heated to 100° C. over a 1.5 hour period. The batch is heated to 110° C. and a vacuum of 135-140 mm is pulled for a 15 minute period. The batch is then heated to 120° C., a vacuum of 135-140 mm is applied for 35 minutes until distillation ceased, then batch is cooled to <60° C. and off-loaded. Product is clear and viscous.

Example 3

117.6 grams of dicyandiamide is added to 99.4 grams of dimethyl sulfoxide and heated under agitation to 85° C. over a 45 minute period. 31.5 grams of paraformaldehyde is charged and then 1.49 grams of methane sulfonic acid/70% is charged. The batch is slowly heated to 150° C. over a 3.5 hour period. The batch is heated to 110° C. and a vacuum of 135-140 mm is pulled for a 15 minute period. The batch is cooled to <60° C. and off-loaded. Product is clear and viscous.

Example 4

111.8 grams of cicyandiamide is added to 98.49 grams of dimethyl sulfoxide, heated under agitation to 80° C., held at 80 C for 1 hr, then heated to 90° C. and held for 30 minutes. 1.24 grams of KOH (flake) is charged, then 35.94 grams of paraformaldehyde is slowly charged, then batch is cooled to 60-70° C. and held for 17 hours. The batch is then heated to 100° C. over a 2 hour period. 10.08 grams of methane sulfonic acid/70% is charged and batch is slowly heated to 100° C. over a 1.5 hour. The batch is heated to 150° C. over a 3 hour period. The batch is then cooled to <60° C. and off-loaded. Product is clear and viscous.

Example 5

42.48 grams of dicyandiamide is added to 54.26 grams of dimethyl sulfoxide and heated under agitation to 80° C. min a 1.5 hour period. The batch is cooled to 40° C., 2.0 grams of paraformaldehyde is charged, the batch is slowly heated to 80° C. over a 1 hour period and then 0.6 gram of methane sulfonic acid/70% is charged. The batch is heated to 90° C. over a 2.25 hour period and 48.8 grams ethylene glycol is added. The batch is cooled to <60° C. and off-loaded. Product is turbid with particles and viscous.

Example 6

47.05 grams of dicyandiamide is added to 50.13 grams of dimethyl sulfoxide and heated under agitation to 80° C. min a 1.25 hour period. The batch is cooled to 44° C., 2.22 grams of paraformaldehyde is charged and the batch is slowly heated to 70° C. over a 1 hour period. The batch is heated to 140° C. over a 2.5 hour period. The batch is cooled to <60° C. and off-loaded. Product is turbid with particles and viscous.

Example 7

31.63 grams of dicyandiamide is added to 33.7 grams of dimethyl sulfoxide and heated under agitation to 80° C. min a 0.5 hour period. The batch is cooled to 45° C., 2.0 grams of paraformaldehyde is charged and the batch is slowly heated to 70° C. over a 1 hour period. The batch is held at 70° C. for 1 hour, then 0.4 grams methane sulfonic acid/70% is charged, mixed at 70° C. for one hour and then the batch is heated to 90° C. over a 2 hour period. A vacuum of 29 mm is pulled on the reactor for 20 minutes, the vacuum is broken, 59.48 grams of ethylene glycol are charged and mixed for 1 hour. The batch is cooled to <60° C. and off-loaded. Product is turbid with particles and viscous.

Example 8

67.0 grams of dicyandiamide is added to 67.4 grams of dimethyl sulfoxide and heated under agitation to a minimum of 90° C. for a 1.0 hour period. The batch is cooled to 45° C., 5.32 grams of paraformaldehyde is charged and the batch is slowly heated to 70° C. over a 7.5 hour period. 0.8 grams methane sulfonic acid/70% is charged and mixed at 70° C. for one hour and then the batch is heated to 90° C. over a 1 hour period. 32.27 grams of ethylene glycol are charged and mixed for 1 hour. The batch is cooled to <60° C. and off-loaded. Product is turbid with particles and viscous.

Example 9

83.64 grams of dicyandiamide is added to 108.73 grams of dimethyl sulfoxide and heated under agitation to 90° C. over a 1.0 hour period. The batch is cooled to 45° C., 6.64 grams of paraformaldehyde is charged and the batch is slowly heated to 75° C. over a 3.0 hour period. 1.0 gram methane sulfonic acid/70% is charged and mixed at 75° C. for 1.5 hours and then the batch is heated to 95° C. over a 2 hour period. A vacuum of 20 mm is pulled for 40 minutes, the vacuum is broken and the batch is cooled to <60° C. and off-loaded. Product is clear and viscous.

Example 10

96.8 grams of dicyandiamide is added to 80 grams of dimethyl sulfoxide and heated under agitation to 90° C. over a 0.75 hour period. The batch is cooled to 45° C., 23.05 grams of paraformaldehyde is charged and the batch is slowly heated to 70° C. over a 4.5 hour period. The batch is held at 70° C. for a period of 10 hours. 1.0 gram methane sulfonic acid/70% is charged and mixed at 70° C. for 0.5 hours and then the batch is heated to 95° C. over a 2.25 hour period. A vacuum of 20 mm is pulled for 40 minutes, the vacuum is broken and the batch is cooled to <60° C. and off-loaded. Product is clear and viscous.

Example 11

82.51 grams of dicyandiamide is added to 107.14 grams of dimethyl sulfoxide, heated under agitation to 85° C. and held at 85° C. for 1.25 hour period. The batch is cooled to 45° C., 7.39 grams of paraformaldehyde is charged and the batch is mixed over a 3.5 hour period. The batch is heated to 75° C. over a period of 2.5 hours. 1.0 gram methane sulfonic acid/70% is charged and mixed at 75° C. for 1.5 hours and then the batch is heated to 100° C. over a 2.25 hour period. A vacuum of 50-55 mm is pulled for 30 minutes, the vacuum is broken, 1.97 grams of triethanolamine is charged and the batch is cooled to <60° C. and off-loaded. Product is clear and fluid.

Example 12

106.63 grams of dicyandiamide is added to 106.32 grams of dimethyl sulfoxide, heated under agitation to 85° C. and held at 85° C. for 1.0 hour period. The batch is cooled to 50.8° C., 11.25 grams of paraformaldehyde is charged, and the batch is mixed over a 1.25 hour period. The batch is heated to 85° C. over a period of 5.75 hours. The batch is held at 85° C. for a period of 15 hours. Batch was cooled to 75° C., 1.27 gram methane sulfonic acid/70% is charged, mixed at 75° C. for 1.5 hours and then the batch is heated to 100° C. over a 2.0 hour period. A vacuum of 50-55 mm is pulled for 30 minutes, the vacuum is broken, 2.55 grams of triethanolamine is charged, and the batch is cooled to <60° C. and off-loaded. Product is hazy and viscous.

Example 13

102.44 grams of dicyandiamide is added to 80 grams of dimethyl sulfoxide, heated under agitation to 80° C. and held at temperature for a 1.0 hour period. The batch is cooled to 44.0° C., 14.64 grams of paraformaldehyde is charged and the batch is mixed over a 0.75 hour period. The batch is heated to 85° C. over a period of 2 hours. The batch is held at 80° C. for a period of 1 hour. Batch is cooled to 61° C., 0.88 grams methane sulfonic acid/70% is charged, mixed 1 hour and allowed to exotherm to 70° C. The batch is then heated to 100° C. over a 3.75 hour period. A vacuum of 45-55 mm is pulled for 30 minutes, the vacuum is broken, 2.04 grams of triethanolamine is charged and the batch is cooled to <60° C. and off-loaded. Product is clear and viscous.

Example 14

138.47 grams of dicyandiamide is added to 120 grams of dimethyl sulfoxide, heated under agitation to 80° C., and held at temperature for a 1.0 hour period. The batch is cooled to 60° C., 32.97 grams of paraformaldehyde is charged, and the batch is mixed over a 1.15 hour period. The batch is heated to 80° C. over a period of 2 hours. The batch is cooled to 61° C., 2.57 grams methane sulfonic acid/70% is charged, mixed 1 hour and allowed to exotherm to 70° C. The batch is then heated to 100° C. over a 2 hour period. A vacuum of 45-55 mm is pulled for 30 minutes, the vacuum is broken, 5.99 grams of triethanolamine is charged, and the batch is cooled to <60° C. and off-loaded. Product is clear and viscous.

Example 15

180.18 grams of dicyandiamide is added to 140 grams of dimethyl sulfoxide, heated under agitation to 80° C. and held at temperature for a 1.0 hour period. The batch is cooled to 56° C., 19.01 grams of paraformaldehyde is charged, and the batch is mixed over a 1 hour period. The batch is heated 80° C. over a period of 2 hours. The batch is cooled to 60.3° C., 3.25 grams methane sulfonic acid/70% is charged, mixed 1 hour and allowed to exotherm to 70° C. The batch is then heated to 115° C. over a 6 hour period. A vacuum of 45-55 mm is pulled for 30 minutes, the vacuum is broken, 7.56 grams of triethanolamine and 17.6 grams of tripropylene glycol monomethyl ether are charged and the batch is cooled to <60° C. and off-loaded. Product is clear and viscous.

Example 16

174.57 grams of dicyandiamide is added to 140 grams of dimethyl sulfoxide, heated under agitation to 80° C. and held at temperature for a 1.0 hour period. The batch is cooled to 55° C., 24.94 grams of paraformaldehyde is charged, and the batch is mixed over a 1.15 hour period. The batch is heated 80° C. over a period of 2 hours. The batch is cooled to 60° C., 3.99 grams methane sulfonic acid/70% is charged, mixed 1 hour and allowed to exotherm to 70° C. The batch is then heated to 115° C. over a 4 hour period. A vacuum of 45-55 mm is pulled for 30 minutes, the vacuum is broken, 6.50 grams of triethanolamine is charged and the batch is cooled to <60° C. and off-loaded. Product is clear and viscous.

Example 17

100.45 grams of urea is added to 80 grams of dimethyl sulfoxide, heated under agitation to 80° C. and held at temperature for 1.0 hour period. The batch is cooled to 53.6° C., 2 drops of 45% KOH and 16.74 grams of paraformaldehyde are charged and the batch is mixed over a 1.15 hour period. The batch is heated 75° C. over a period of 2 hours. The batch is held at 75° C. for an additional period of 1 hour. The batch is cooled to 44.7° C., 3.99 grams methane sulfonic acid/70% is charged, mixed 1 hour and allowed to exotherm to 60.7° C. The batch is then heated to 90° C. over a 2 hour period. A vacuum of 45-55 mm is pulled for 30 minutes, the vacuum is broken, 1.88 grams of triethanolamine is charged, and the batch is cooled to <60° C. and off-loaded. Product is opaque and very viscous.

Example 18

142.12 grams of urea is added to 99.58 grams of dimethyl sulfoxide, heated under agitation to 80° C. min and held at temperature for a 1.0 hour period. The batch is cooled to 45° C., 2 drops of 45% KOH and 60.06 grams of paraformaldehyde are charged and the batch is mixed over a 1.15 hour period. The batch is heated 70° C. over a period of 2 hours. The batch is held at 70° C. for an additional period of 1 hour. 128 grams of methanol is charged to the batch. The batch is then heated to reflux for one hour and then cooled to 44.7° C. The pH is adjusted to 5.5-6.5 with nitric acid/20% and the batch is allowed to exotherm to reflux. After 45 minutes, heat is returned to the reactor for 1 hour to maintain reflux. The pH is adjusted to 8.8-9.5 with 45% KOH and methanol/water is removed. When distillation ceases the batch is placed under vacuum of <40 mm until distillation ceases. The batch is cooled to 45° C. The pH is adjusted to 5.5-6.5 with nitric acid/20% and the batch is allowed to exotherm to reflux. After 10 minutes, heat is returned to the reactor for 1 hour to maintain reflux. The pH is adjusted to 8.8-9.5 with 45% KOH and methanol/water is removed. When distillation ceases the batch is placed under vacuum of <40 mm until distillation ceases. The batch is cooled to 45° C. The pH is adjusted to 5.5-6.5 with nitric acid/20% and the batch is allowed to exotherm to reflux. After 10 minutes, heat is returned to the reactor for 1 hour to maintain reflux. The pH is adjusted to 8.8-9.5 with 45% KOH and methanol/water is removed. When distillation ceases, the batch is placed under vacuum of <40 mm until distillation ceases. The batch is cooled to <60° C. and off-loaded. Product is opaque and very viscous. Clear at 70-90° C.

Many of these hydrophobic, biodegradable polymers that have been produced within the NOSDS, dimethyl sulfoxide are high viscosity and a few demonstrate poor shelf stability. Formulations have been prepared utilizing other NOSDSs to impart improvements in these properties. The following table illustrates samples that were formulated using standard overhead mixing and temperatures of 40-120° C.

| Ingredients | Ex. 19 | Ex. 20 | Ex. 21 | Ex. 22 | Ex. 23 | Ex. 24 | Ex. 25 | Ex. 26 | Ex. 27 | Ex. 28 | Ex. 29 | Ex. 30 | Ex. 31 | Ex. 32 | Ex. 33 |
|---|---|---|---|---|---|---|---|---|---|---|---|---|---|---|---|
| Example 2 | 62.2 | 62.6 | 62.6 | 62.6 | 62.6 | 62.6 | 62.6 | 62.6 | 62.6 | | | | | | |
| Example 6 | | | | | | | | | | 62.1 | 62.1 | 62.1 | | | |
| Example 11 | | | | | | | | | | | | | | 85.0 | 75.0 |
| Example 17 | | | | | | | | | | | | | 50.0 | | |
| TPM | | | | | | | | | | | | | | 15.0 | 25.0 |
| DPG | | | | | | | | | | | | 37.9 | | | |
| DMSO | 37.8 | | | | | | | | | | | | 50.0 | | |
| DPMAc | | | | | | | | | | | | | | | |
| DimGlut | | 37.8 | | | | | | | | | | | | | |
| Ethyl Lactate | | | | | 37.4 | | | | | | | | | | |
| IPDG | | | 37.4 | | | | | | | | | | | | |
| DBE-3 | | | | 37.4 | | | | | | | | | | | |
| PropCarb | | | | | | | | 37.4 | | | | | 37.9 | | |
| HexGly | | | | | | | | | | 37.4 | | | | | |
| PG | | | | | | | 37.4 | | | | | | | | |
| EG | | | | | | 37.4 | | | | | | | | | |
| ButCarb | | | | | | | | | | | 37.9 | | | | |
| Appearance | Clr | Clr | P | Clr | Clr | Clr | Clr | Clr | P | Clr | Clr | Clr | P | Clr | Clr |
| Freeze/thaw | G | G | DNR | G | G | G | G | G | DNR | G | G | G | DNR | G | G |

Clr = Clear
P = Poor
G = Good
DNR = Did not Run
TPM: Tripropyleneglycol methyl ether
DPG: Dirpopylene Glycol
DMSO: Dimethyl Sulfwdde
DPMAc: dipropyleneglycol methyl ether acetate
DimGlut: Dimethyl Glutarate
IPDG: Isopropylideneglycerol
DBE-3: dimethyl adipate , glutarate and succinate
PropCarb: propylene Carbonate
HexGly: Hexylene Glycol
PG: propylene glycol
EG: ethylene glycol
L-62: EO/PO blocked copolymer
ButCarb: Butylene Carbonate

| Ingredients | Ex. 34 | Ex. 35 | Ex. 36 | Ex. 37 | Ex. 38 | Ex. 39 | Ex. 40 | Ex. 41 | Ex. 42 | Ex. 43 | Ex. 44 | Ex. 45 | Ex. 46 | Ex. 47 |
|---|---|---|---|---|---|---|---|---|---|---|---|---|---|---|
| Example 11 | 85.0 | 75.0 | | | | | | | | | | | | |
| Example 12 | | | 50.0 | 50.0 | 50.0 | 50.0 | | | | | | | | |
| Example 13 | | | | | | | 87.0 | 64.0 | 95.0 | 50.0 | 75.0 | | | |
| Example 15 | | | | | | | | | | | | 95.0 | | |
| Example 16 | | | | | | | | | | | | | 50.0 | 75.0 |

-continued

| Ingredients | Ex. 34 | Ex. 35 | Ex. 36 | Ex. 37 | Ex. 38 | Ex. 39 | Ex. 40 | Ex. 41 | Ex. 42 | Ex. 43 | Ex. 44 | Ex. 45 | Ex. 46 | Ex. 47 |
|---|---|---|---|---|---|---|---|---|---|---|---|---|---|---|
| TPM |  |  | 50.0 |  |  |  |  | 36.0 | 5.0 |  |  | 5 |  |  |
| DPG | 15.0 | 25.0 |  |  |  | 50.0 |  |  |  | 50.0 | 25 |  | 50 | 25 |
| DMSO |  |  |  |  |  |  |  |  |  |  |  |  |  |  |
| DPMAc |  |  |  |  |  |  |  | 13.0 |  |  |  |  |  |  |
| L-62 |  |  |  |  | 50.0 |  |  |  |  |  |  |  |  |  |
| ButCarb |  |  |  | 50.0 |  |  |  |  |  |  |  |  |  |  |
| Appearance | Clr | Clr | Clr | Clr | Clr | Clr | Clr | Clr | Clr | Clr | Clr | Clr | Clr | Clr |
| Freeze/thaw | G | G | G | G | G | G | G | G | G | G | G | G | G | G |

Clr = Clear
P = Poor
G = Good
DNR = Did not Run
TPM: Tripropyleneglycol methyl ether
DPG: Dirpopylene Glycol
DMSO: Dimethyl Sulfwdde
DPMAc: dipropyleneglycol methyl ether acetate
DimGlut: Dimethyl Glutarate
IPDG: Isopropylideneglycerol
DBE-3: dimethyl adipate, glutarate and succinate
PropCarb: propylene Carbonate
HexGly: Hexylene Glycol
PG: propylene glycol
EG: ethylene glycol
L-62: EO/PO blocked copolymer
ButCarb: Butylene Carbonate The following examples are formulations of the hydrophobic, biodegradable polymers that have been produced within the dimethyl sulfoxide and formulated with other aprotic and protic solvents and biologically active agents such as urease and nitrification inhibitors.

As shown by the above examples, biologically active agents can be added to the hydrophobic, biodegradable polymers that have been produced within the NOSDS, dimethyl sulfoxide and further can be added to the hydrophobic, biodegradable polymers that have been produced

| Ingredients | Ex. 48 | Ex. 49 | Ex. 50 | Ex. 51 | Ex. 52 | Ex. 53 | Ex. 54 | Ex. 55 | Ex. 56 | Ex 57 |
|---|---|---|---|---|---|---|---|---|---|---|
| Example 32 | 95.0 |  |  |  |  |  |  |  |  |  |
| Example 33 |  | 93.0 |  |  |  |  |  |  |  |  |
| Example 34 |  |  | 93.0 |  |  |  |  |  |  |  |
| Example 35 |  |  |  | 93.0 |  |  |  |  |  |  |
| Example 36 |  |  |  |  | 93.0 |  |  |  |  |  |
| Example 37 |  |  |  |  |  | 93 |  |  |  |  |
| Example 11 |  |  |  |  |  |  |  |  |  | 85 |
| Example 44 |  |  |  |  |  |  | 90.9 | 95 | 95 |  |
| N-(n-butyl) thiophosphoric triamide | 5.0 | 7.0 | 7.0 | 7.0 | 7.0 | 7.0 |  |  |  | 15 |
| 2-Chloro-6-(trichloromethyl) pyridine |  |  |  |  |  |  | 9.1 |  |  |  |
| aminomethyl(N-n butylaminomethyl) phosphinic acid |  |  |  |  |  |  |  | 5 |  |  |
| aminomethyl(N-n hexylaminomethyl) phosphinic acid |  |  |  |  |  |  |  |  | 5 |  |
| Appearance | Clr | Clr | Clr | Clr | Clr | Clr | Clr | Clr | Clr | Clr |
| Freeze/thaw | G | G | G | G | G | G | G | G | G | G |

Clr = Clear
P = Poor
G = Good
DNR = Did not Run
Note:
dicyandiamide was not included in these experiments since many of the samples already possessed free dicyandiamide such as example 11 and example 12.

within the NOSDS, dimethyl sulfoxide and further formulated with protic and aprotic solvents to produce stable products.

A number of the examples were tested for improving urea's resistance to dissolution. The experimental samples were applied to urea using standard overhead mixer with an anchor agitator. The amount of the sample to charge was determined by the specific gravity of the sample times the volumetric treatment level. For example: Determining the amount of Example 32 to be charged at a rate of 3 quarts/ton of urea:

Specific gravity=1.163 gm/ml=9.68 lb/gal

At an application level of 3 quart/ton of urea=7.26 lbs of Example 32/2000 lbs of urea The application level would be 0.363% of Example 32

The 200 grams of urea was placed in a vessel, agitation was set so not to sling the urea out of the vessel and the calculated amount of the experimental sample was dripped onto the agitating urea. After completing the sample addition, the urea was agitated for an additional minute to insure uniform coverage. Some samples required approximately 1-2% of hydrophobic silica as a flow aide to improve the flow properties of the treated urea. The treated urea was set aside for 24 hours in either at room temperature or at 50° C. The dissolution test method was performed in 100 mls of distilled water in a 150 ml beaker by dropping one granule of either treated or untreated urea into the water. Time was measured from when the urea entered the water until it had dissolved.

Example 58

| Treatment level 4 quarts/ton | |
|---|---|
| Experimental Sample # | % improvement over urea dissolution |
| Ex 19 | 13% |
| Ex 24 | 17% |
| Ex 25 | 33% |
| Ex 22 | 42% |

Example 59

| Treatment level 3 quarts/ton 50 C. for 3 days | |
|---|---|
| Experimental Sample # | % improvement over urea dissolution |
| Ex 31 + silica | 77% |
| Ex 31 | 51% |
| Ex 36 | 39% |
| Ex 38 + silica | 82% |
| Ex 38 + silica | 72% |
| Ex 39 | 46% |

Example 60

| Treatment level 3 quarts/ton 50 C. for 3 days | |
|---|---|
| Experimental Sample # | % improvement over urea dissolution |
| Ex 32 | 41% |
| Ex 33 | 33% |
| Ex 34 | 34% |
| Ex 35 | 77% |

* Note:
Testing of Ex 32 & Ex 33 showed a large gel in place of the treated urea that did not disperse for over three days A couple of experimental samples containing biological active agents were tested for improving urea's resistance to dissolution utilizing the previous testing procedure.

| Treatment level 3 quarts/ton 50 C. for 3 days | |
|---|---|
| Experimental Sample # | % improvement over urea |
| Ex 49 | 48% |
| Ex 50 | 22% |
| Ex 57 | 25% |

Example 61

106.82 grams of DMSO and 82.26 grams of DCD were charged to a reaction flask, heated to 86.4° C., held until contents were clear and then cooled to 50° C. 7.37 grams of paraformaldehyde were charged and then mixed for 30 minutes. The contents were then heated to 86.2° C. over a 3 hour period and held until the solution became clear. The contents were cooled to 59.9° C. and then 1.19 grams of methane sulfonic acid/70% were added. The contents were mixed for 5 minutes and then the contents were slowly heated to 110° C. over a 2.5 hr period of time. At 110° C., a vacuum of 45-65 mm Hg was applied to the reaction flask for 0.5 hrs, the vacuum was broken with nitrogen and then the contents were cooled to <45° C. and packaged. The amount of distillate collected was 11.26 grams, the yield 178.82 grams and the calculated amount of DCD was 46.21%.

Example 62

106.82 grams of DMSO and 82.26 grams of DCD were charged to a reaction flask, heated to 95° C., held until contents were clear and then cooled to 65° C. 7.37 grams of paraformaldehyde were charged and the contents were then heated to 81° C. over a 0.75 hour period and held 1.3 hrs until the solution became clear. The contents were cooled to 41.7° C. and then 1.19 grams of methane sulfonic acid/70% were added. The contents were mixed for 5 minutes and then the contents were slowly heated to 110° C. over a 2.1 hr period of time. At 110° C., a vacuum of 54-65 mm Hg was applied to the reaction flask for 0.8 hr, the vacuum was broken by nitrogen, 2.37 grams of triethanolamine/99% were charged and then the contents were cooled to <45° C. and packaged. The yield 189.08 grams and the calculated amount of DCD was 43.5%.

Example 63

101.6 grams of DMSO and 87.05 grams of DCD were charged to a reaction flask, heated to 110° C., held until contents were clear and then cooled to 60° C. 7.80 grams of paraformaldehyde were charged and then the contents were heated to 85° C. over a 8.5 hour period. 1.19 grams of methane sulfonic acid/70% were added. The contents were mixed for 5 minutes and then the contents were slowly heated to 95° C. over a 2 hr period of time. At 95° C., a vacuum of 35-50 mm Hg was applied to the reaction flask for 0.5 hr, the vacuum was broken by nitrogen and then the contents were cooled to <45° C. and packaged. The yield 189.4 grams and the calculated amount of DCD was 45.96%.

Example 64

140 grams of DMSO and 174.57 grams of DCD were charged to a reaction flask, heated to 82° C., held for 1 hr and then cooled to 65° C. 24.94 grams of paraformaldehyde were charged, the contents were then heated to 75° C. and held at temperature for 3.5 hrs. 3.99 grams of methane sulfonic acid/70% were added over a 0.75 hr period, the contents were mixed for 5 minutes and then the contents were slowly heated to 110° C. over a 2.1 hr period of time. At 110° C., a vacuum was applied to the reaction flask for 0.8 hr, the vacuum was broken by nitrogen and then the contents were cooled to <45° C. and packaged. The yield 309.5 grams and the calculated amount of DCD was 57.24%.

Example 65

140 grams of DMSO and 162.12 grams of DCD were charged to a reaction flask, heated to 82° C. and held for 1 hr and then cooled to 65° C. 38.60 grams of paraformaldehyde were charged, mixed for 0.5 hr and the contents were then heated to 85° C. over a 3.75 hr period and held at temperature for 0.75 hrs. 3.53 grams of methane sulfonic acid/70% were added over a 0.3 hr period, the contents were mixed for 5 minutes and then the contents were slowly heated to 110° C. over a 3.8 hr period of time. At 110° C., a vacuum of 27-31 mm Hg was applied to the reaction flask for 0.7 hr, the vacuum was broken by nitrogen and then the contents were cooled to <45° C. and packaged. The amount of distillate collected was 33.15 grams, the yield 299.03 grams and the calculated amount of DCD was 53.33%.

Example 66

140 grams of DMSO and 153.37 grams of DCD were charged to a reaction flask, heated to 85° C., held for 1 hr. 45.65 grams of paraformaldehyde were charged, mixed for 0.5 hr and then the contents were then heated to 85° C. over a 3.75 hr period and held at temperature for 1.25 hrs. 4.17 grams of methane sulfonic acid/70% were added over a 0.25 hr period, the contents were mixed for 5 minutes and then the contents were slowly heated to 110° C. over a 4.5 hr period of time. At 110° C., a vacuum of 23.6-31 mm Hg was applied to the reaction flask for 0.5 hr, the vacuum was broken by nitrogen and then the contents were cooled to <45° C. and packaged. The amount of distillate collected was 46.09 grams, the yield 287.27 grams and the calculated amount of DCD was 52.35%.

Example 67

181.18 grams of DMSO and 144.87 grams of DCD were charged to a reaction flask, heated to 85° C., held for 1 hr and then cooled to 65° C. 13.45 grams of paraformaldehyde were charged, mixed for 0.5 hr and the contents were then heated to 110° C. over a 9.5 hr period and held at temperature for 0.5 hrs. No methane sulfonic acid/70% was added. The contents were cooled to 90° C. over a 0.5 hr period of time. At 90° C., a vacuum of 28-31 mm Hg was applied to the reaction flask for 0.5 hr, the vacuum was broken by nitrogen and then the contents were cooled to <45° C. and packaged. The amount of distillate collected was 49.27 grams, the yield 329.93 grams and the calculated amount of DCD was 43.91%.

Example 68

181.18 grams of DMSO and 144.87 grams of DCD were charged to a reaction flask, heated to 80° C. and held for 1 hr. At 80° C., 13.45 grams of paraformaldehyde were charged, mixed for 0.5 hr and the contents were then heated to 85° C. and held at temperature for 8.5 hrs. No methane sulfonic acid/70% was added. The contents were heated to 90-95° C. and held at temperature for a 12 hr period of time. At 90° C., a vacuum of 22.3-28.0 mm Hg was applied to the reaction flask for 1.0 hr, the vacuum was broken by nitrogen and then the contents were cooled to <45° C. and packaged. The amount of distillate collected was 11.36 grams, the yield 322.35 grams and the calculated amount of DCD was 44.95%.

Example 69

179.47 grams of DMSO and 144.28 grams of DCD were charged to a reaction flask and heated to 45° C. and an inert vessel was achieved by pulling a vacuum then breaking with nitrogen and repeating this procedure 2 times. 13.74 grams of paraformaldehyde were charged and mixed for 0.5 hr and the contents were then heated to 90° C. over a 9 hr period. At 90° C. 2.04 grams of methane sulfonic acid/70% were added. The contents were mixed for 5 minutes and then the contents were slowly heated to 95° C. and held for a 2 hr period of time. At 95° C., a vacuum of 28 mm Hg was applied to the reaction flask for 0.5 hr, the vacuum was broken by nitrogen and then the contents were cooled to <45° C. and packaged. The amount of distillate collected was 11.55 grams, the yield 322.37 grams and the calculated amount of DCD was 44.76%.

Example 70

179.47 grams of DMSO and 144.28 grams of DCD were charged to a reaction flask and heated to 40° C., an inert vessel was achieved by pulling a vacuum then breaking with nitrogen and repeating this procedure 2 times. 13.74 grams of paraformaldehyde were charged and mixed for 0.5 hr and the contents were then heated to 112.6° C. over a 6.5 hr period. No methane sulfonic acid/70% was added. At 110° C., a vacuum of 2 mm Hg was applied to the reaction flask for 0.5 hr, the vacuum was broken by nitrogen and then the contents were cooled to <45° C. and packaged. The amount of distillate collected was 19.17 grams, the yield 314.18 grams and the calculated amount of DCD was 45.65%.

Example 71

179.47 grams of DMSO, 13.74 grams of paraformaldehyde and 144.28 grams of DCD were charged to a reaction flask at a temperature of 35° C., an inert vessel was achieved by pulling a vacuum then breaking with nitrogen and repeating this procedure 2 times. mixed for 0.5 hr and the contents were then heated to 100° C. over a 2 hr period and held at 100° C. for a period of 5 hrs. No methane sulfonic acid/70% was added. At 100° C., a vacuum was applied to the reaction flask for 0.7 hr, the vacuum was broken by nitrogen and then the contents were cooled to <45° C. and packaged. The amount of distillate collected was 18.4 grams, the yield 313.8 grams and the calculated amount of DCD was 45.70%.

Example 72

179.47 grams of DMSO, 13.74 grams of paraformaldehyde and 144.28 grams of DCD were charged to a reaction flask at a temperature of 35° C., an inert vessel was achieved by pulling a vacuum then breaking with nitrogen and repeating this procedure 2 times. mixed for 0.5 hr and the contents were then heated to 80° C. over a 2 hr period and held at 80° C. for a period of 7 hrs. At 80° C. 2.04 grams of methane sulfonic acid/70% were added. The contents were mixed for 5 minutes and then the contents were mixed at 80° C. for a 1 hr period of time. The contents were then heated to 90 C and a vacuum was applied to the reaction flask for a period of 2 hr, the vacuum was broken by nitrogen and then the contents were cooled to <45° C. and packaged. The amount of distillate collected was 13.47 grams, the yield 320.65 grams and the calculated amount of DCD was 46.39%.

Example 73

193.68 grams of DMSO and 104.19 grams of DCD were charged to a reaction flask at a temperature of 18° C., an inert vessel was achieved by pulling a vacuum then breaking with nitrogen and repeating this procedure 2 times. 16.91 grams of paraformaldehyde charged, mixed for 0.25 hr and the contents were then heated to 70° C. over a 0.5 hr period and held at 70° C. for a period of 13 hrs. No methane sulfonic acid/70% was added. The contents were then heated to 90 C and held for 4 hours. 35.22 grams of DCD were charged a vacuum of 15 mm Hg was applied to the reaction flask for a period of 1.5 hr while the temperature was allowed to cooled to 80° C. The vacuum was broken by nitrogen and then the contents were cooled to <45° C. and packaged. The amount of distillate collected was 15.86 grams, the yield was 329.73 grams and the calculated amount of DCD was 42.12%.

Example 74

204.23 grams of DMSO and 120.84 grams of DCD were charged to a reaction flask at a temperature of 18° C., an inert vessel was achieved by pulling a vacuum then breaking with nitrogen and repeating this procedure 2 times. 19.62 grams of paraformaldehyde mixed for 0.25 hr and the contents were then heated to 70° C. over a 0.5 hr period and held at 70° C. for a period of 3.5 hrs. At 70° C., 2.08 grams of methane sulfonic acid/70% were added. The contents were mixed for 5 minutes and then the contents were mixed at 70° C. for a 1 hr period of time. The contents were then heated to 80 C and held for 3 hours at temperature and under a vacuum. The vacuum was broken by nitrogen and then the contents were cooled to <45° C. and packaged. The amount of distillate collected was 17.89 grams, the yield was 326.32 grams with a strong smell of formaldehyde and the calculated amount of DCD was 36.69%.

Example 75

204.23 grams of DMSO and 120.84 grams of DCD were charged to a reaction flask at a temperature of 18° C., an inert vessel was achieved by pulling a vacuum then breaking with nitrogen and repeating this procedure 2 times, charged 19.62 grams of paraformaldehyde mixed for 0.25 hr and the contents were then heated to 84.3° C. over a 0.5 hr period and held at 80° C. for a period of 3.5 hrs. At 80° C., 2.08 grams of methane sulfonic acid/70% were added and mixed for 1 hr, At 80° C., the contents were placed under a vacuum of 15-30 mm Hg and held at 80° C. for a period of 1.5 hr. The contents were then heated to 90 C and held for 3 hours at temperature and under a vacuum. The vacuum was broken by nitrogen, 3.23 grams of triethanolamine/99% was charged and then the contents were cooled to <45° C. and packaged. The amount of distillate collected was 28.93 grams, the yield was 315.99 grams and the calculated amount of DCD was 38.24%.

Example 76

754.11 grams of DMSO and 619.74 grams of DCD were charged to a reaction flask at a temperature of 20° C., an inert vessel was achieved by pulling a vacuum then breaking with nitrogen and repeating this procedure 2 times, charged 63.19 grams of paraformaldehyde mixed for 0.25 hr and the contents were then heated to 80° C. over a 0.75 hr period and held at 80° C. for a period of 6 hrs. At 80° C., 8.67 grams of methane sulfonic acid/70% were added. The contents were mixed for 5 minutes and then the contents were placed under a vacuum of <50 mm Hg for period of a 1 hr. The contents were then heated to 90-95° C. and held for 4.5 hours at temperature and under a vacuum. The vacuum was broken by nitrogen, a portion was removed for analytical purpose (coded Example 76 base) and then 9.42 grams of triethanolamine/99% and 29.95 grams of a polysuccinimide were charged and mixed until homogeneous. The contents were cooled to <45° C. and packaged. The data of the example 76 base is the amount of distillate collected was 42.09 grams, the yield was 1425.28 grams and the calculated amount of DCD was 44.95%.

Example 77

71.01 grams of DMSO and 66.72 grams of 3,5-dimethylpyrazole were charged to a reaction flask at a temperature of 18° C., an inert vessel was achieved by pulling a vacuum then breaking with nitrogen and repeating this procedure 2 times, charged 10.42 grams of paraformaldehyde mixed for 0.25 hr and the contents were then heated to 80.0° C. over a 4.0 hr period. At 80° C., 0.89 grams of methane sulfonic acid/70% was added and mixed for 1 hr. The contents were then heated to 110 C over a period of time of 2.5 hrs and held for 0.5 hours at temperature. Contents were cooled to 90° C. and placed under a vacuum of 29 mm Hg for a period of time of 1.5 hrs. The vacuum was broken by nitrogen and then the contents were cooled to <45° C. and packaged. The amount of distillate collected was 9.55 grams and the yield was 135.28.

Example 78

75.28 grams of DMSO and 61.87 grams of DCD were charged to a reaction flask at a temperature of 20.4° C., an inert vessel was achieved by pulling a vacuum then breaking with nitrogen and repeating this procedure 2 times, charged 11.05 grams of paraformaldehyde mixed for 0.25 hr and the contents were then heated to 80° C. held at 80° C. over a 3.0 hr period of time. At 80° C., 0.87 grams of methane sulfonic acid/70% was added and mixed for 1 hr. At 80° C., the contents were placed under a vacuum of 15-30 mm Hg and the contents were then heated to 90 C and held for 0.3 hours at temperature and under a vacuum. The vacuum was broken by nitrogen, and then the contents were cooled to <45° C. and packaged. The amount of distillate collected was 9.45 grams, the yield was 132.71 grams with a slight smell of formaldehyde and the calculated amount of DCD was 46.62%.

Example 79

70.44 grams of DMSO and 59.88 grams of DCD were charged to a reaction flask at a temperature of 18.6° C., an inert vessel was achieved by pulling a vacuum then breaking with nitrogen and repeating this procedure 2 times, charged 17.82 grams of paraformaldehyde mixed for 0.25 hr and the contents were then heated to 80° C. held at 80° C. over a 2.0 hr period of time. At 80° C., 0.89 grams of methane sulfonic acid/70% was added and the contents were placed under a vacuum of 16-30 mm Hg for a period of 0.5 hrs. The contents were then heated to 90 C and held for a period of 2 hours at temperature and under a vacuum of 16 mm Hg. The vacuum was broken by nitrogen, the vessel was placed under vacuum and then the vacuum was broken by a hard sparge of nitrogen (was repeated 3 times) and then the contents were cooled to <45° C. and packaged. The amount of distillate collected was 12.01 grams, the yield was 129.0 grams and the calculated amount of DCD was 46.12%.

Example 80

23.67 grams of sulfolane and 22.24 grams of 3,5-dimethylpyrazole were charged to a reaction flask at a temperature of 18° C., 10.42 grams of paraformaldehyde were charged and mixed for 0.25 hr and the contents were then heated to 80.0° C. over a 2.0 hr period. At 80° C., 0.30 grams of methane sulfonic acid/70% was added and mixed for 1 hr. The contents were then heated to 100 C over a period of time of 1 hr and held for 0.5 hours at temperature. Contents were placed under a vacuum of 19 mm Hg for a period of time of 0.5 hrs. The vacuum was broken by nitrogen and then the contents were cooled to <45° C. and packaged. The amount of distillate collected was 0 grams and the yield was 47.7 grams.

Example 81

64.72 grams of DMSO, 55.03 grams of DCD and 12.16 grams of 3,5-dimethylpyrazole were charged to a reaction flask at a temperature of 20.4° C., an inert vessel was achieved by pulling a vacuum then breaking with nitrogen and repeating this procedure 2 times, charged 19.44 grams of paraformaldehyde, contents were mixed for 0.25 hr and the contents were then heated to 80° C. held at 80° C. over a 2.0 hr period of time. Contents were cooled to 60° C. and 0.91 grams of methane sulfonic acid/70% was added, the contents were placed under a vacuum of 15 mm Hg and the contents were then heated to 90 C and held for 3 hours at temperature and under a vacuum. The vacuum was broken by nitrogen, 0.99 grams of triethanolamine/99% were charged and then the contents were cooled to <45° C. and packaged. The amount of distillate collected was 13.94 grams, the yield was 126.98 grams and the calculated amount of DCD was 43.58%.

Example 82

77.74 grams of DMSO and 63.88 grams of DCD were charged to a reaction flask at a temperature of 15.4° C., an inert vessel was achieved by pulling a vacuum then breaking with nitrogen and repeating this procedure 2 times, charged 6.51 grams of paraformaldehyde mixed for 0.25 hr and the contents were then heated to 80° C. held at 80° C. over a 3.0 hr period of time. Contents were cooled 40° C., 0.89 grams of pTSA was added and the contents were placed under a vacuum of 29-30 mm Hg. The contents were then heated to 90 C and held for a period of 2 hours at temperature and under a vacuum of 21 mm Hg. The vacuum was broken by nitrogen, ½ of the contents were removed and coded Example 82 and then Example 82 was cooled to <45° C. and packaged. The amount of distillate collected was 6.48 grams, the yield was 139.48 grams and the calculated amount of DCD was 45.8%. The remaining content was continued as Example 83.

Example 83

The remaining contents of Example 82 in the reaction flask were heated to 90-95° C. and 10 grams of distilled water were added. The contents were held at 90-90° C. for a period of 2 hrs and then placed under vacuum until charged water was removed (approx. 11.6 grams of distillate recovered). The contents were then cooled and packaged.

Example 84

Heat 51.6 grams of DMSO to 60° C. under agitation and then charge 48.4 grams of 3,5-dimethylpyrazole (DMP). Mix @60° C. until clear. Package in a seal container and maintain sample @50-70° C. for clarity and homogeneity Example 85

Aluminum weigh pans were weighed and the weight recorded. Approximately 2 grams of sample were weighed into aluminum weigh pan and then placed in an oven @60° C. for 24 hours. After 24 hours, the sample in the aluminum weigh pan was removed from the oven and weighed. The weights were compared and percentage of non-volatile matter was calculated as shown in Chart 1.

CHART 1

| Example | pan wt | Sample initial wt | difference | Weight after 24 hrs @60° C. | % remaining |
|---|---|---|---|---|---|
| *DMSO | 2.645 | 3.674 | 1.029 | 2.645 | 0% |
| Example 77 | 2.644 | 4.874 | 2.230 | 3.251 | 27.22% |
| Example 84 | 2.633 | 4.836 | 2.203 | 2.642 | 0.41% |

*DMSO was 0% remaining after 12 hrs

The results of the volatility test show that the DMP oligomer from example 67 has >50% weight retention versus unreacted DMP from Example 84. The >50% is based on the results that show DMSO has completely volatilized in 24 hours and the footnote that states this volatility occurred after 12 hours.

Example 86

90.9 grams of Example 61 were blended with 9.1 grams of propylene glycol at 30° C. and then packaged. Sample appearance was clear.

Example 87

90.9 grams of Example 61 were blended with 9.1 grams of ethylene glycol at 30° C. and then packaged. Sample appearance was clear.

Example 88

91.4 grams of Example 63 were blended with 8.62 grams of DMSO at 30° C. and then packaged. Sample appearance was clear.

Example 89

91.4 grams of Example 63 were blended at 30° C. with 8.62 grams a 50% ammonium neutralized polyaspartate (polyaspartate polymer weight 3000-5000 grams/mole) dispersed in DMSO and then packaged. Sample appearance was clear.

Example 90

30 grams of Example 64 were blended with 44.45 grams of DMSO, 0.3 grams of triethanolamine, 25.25 grams of DCD were heated to 80° C. mixed until clear, cooled to <40 C and then packaged. Sample appearance was clear.

Example 91

30 grams of Example 65 were blended with 43.54 grams of DMSO, 0.3 grams of triethanolamine, 26.16 grams of DCD were heated to 80° C. mixed until clear, cooled to <40° C. and then packaged. Sample appearance was clear.

Example 92

78.6 grams of Example 64 were blended with 21.4 grams of DMSO at 30° C. and then packaged. Sample appearance was clear.

Example 93

78.6 grams of Example 64 were blended with 21.4 grams of ethylene glycol at 30° C. and then packaged. Sample appearance was clear.

Example 94

78.6 grams of Example 64 were blended with 21.4 grams of polyethylene glycol at 30° C. and then packaged. Sample appearance was clear.

Example 95

83 grams of Example 65 were blended with 17 grams of DMSO at 30° C. and then packaged. Sample appearance was clear.

Example 96

85.13 grams of Example 65 were blended with 14.9 grams of DMSO at 30° C. and then packaged. Sample appearance was clear.

Example 97

97 grams of Example 68 were blended with 2 grams of a polysuccinimide (polymer weight 3000-5000 grams/mole) and 1 gram of a solvent dispersed blue dye at 60° C. and cooled and package. Sample appearance was blue and clear.

Example 98

81.84 grams of Example 73 were blended with 0.66 grams of DMSO, and 14.50 grams of DCD were heated to 80° C. mixed until clear, cooled to <40 C and then packaged. Sample appearance was clear.

Example 99

30 grams of Example 73 were blended at 30° C. with 70 grams a 50% ammonium neutralized polyaspartate (polyaspartate polymer weight 3000-5000 grams/mole) dispersed in DMSO and then packaged. Sample appearance was clear.

Example 100

41.72 grams of Example 73 were blended with 25 grams of a polysuccinimide (polymer weight 3000-5000 grams/mole) and 33.29 grams DMSO at 60° C. and cooled and package. Sample appearance was clear.

Example 101

28.57 grams of tripropylene glycol methyl ether were blended with 0.5 grams of triethanolamine and 40.0 grams of Example 73 and then heated to 40° C. While mixing, 30.93 grams of N-(-n-butyl) thiophosphoric triamide were added and mixed until all particles were dissolved. The sample was clear and packaged.

Example 102

Blends in examples 86-101 were evaluated for sample storage stability and are listed in Chart 2:

CHART 2

| Example # | Stable @ 25° C. for 7 days | Freeze thaw stable (3 times) | Stable @ 50° C. for 3 days |
| --- | --- | --- | --- |
| 86 | Pass | Pass | Pass |
| 87 | Pass | Pass | Pass |
| 88 | Pass | Pass | Pass |
| 89 | Pass | Pass | Pass |
| 90 | Pass | Pass | Pass |
| 91 | Pass | Pass | Pass |
| 92 | Pass | Pass | Pass |
| 93 | Pass | Pass | Pass |
| 94 | Pass | Pass | Pass |
| 95 | Pass | Pass | Pass |
| 96 | Pass | Pass | Pass |
| 97 | Pass | Pass | Pass |
| 98 | Pass | Pass | Pass |
| 99 | Pass | Pass | Pass |
| 100 | Pass | Pass | Pass |
| 101 | Pass | Pass | Pass |

Evaluation shows that blended formulations have good storage stability.

Example 103

Some of the samples were analyzed for viscosity, pH, formaldehyde content and dispersibility in distilled water to yield a borderline translucent dispersion. The results as well as the molar ratio of the reactants are as shown in Chart 3:

CHART 3

| Example # | ratio of DCD to one mole of formaldehyde | Brookfield Viscosity | pH (5%) | *Dispersion of samples | ppm free formaldehyde |
|---|---|---|---|---|---|
| ***62 | 3.988 | 214 | 8.32 | 0.717 | 103 |
| 63 | 3.988 | | | | 48 |
| 88 | Adjusted Ex #63 | | | 0.960 | |
| ***90 | Ex #64 adjusted with DMSO and Free DCD | 119 | 8.22 | 0.860 | 148 |
| 64 | 2.5 | | | | |
| ***91 | Ex #65 adjusted with DMSO and Free DCD | 173 | 8.22 | 0.586 | 198 |
| 65 | 1.5 | | | | |
| **67 | 3.85 | 320 | 8.6 | 4.800 | 53 |
| 68 | 3.85 | | | 2.452 | 54 |
| 69 | 3.75 | 354 | 7.1 | 2.877 | 59 |
| **71 | 3.75 | | | 2.181 | 206 |
| 72 | 3.75 | 330 | 7.05 | 3.615 | 490 |
| **73 | 2.2 adjusted insitu with free DCD | 203 | 8.11 | 2.336 | 118 |
| 76 | 3.5 | 275 | 7.17 | 1.685 | 66 |
| 78 | 2 | 820 | 7.12 | 2.988 | 603 |
| 79 | 1.2 | 4780 | 7.09 | 0.700 | 180 |
| 82 | 3.5 | 275 | 7.15 | 3.920 | 41 |
| 83 | 3.5 | 303 | 7.25 | 1.070 | 21 |

*grams of sample in 100 grams of Distilled Water (Barely Translucent in Appearance)
**No acid catalyst charged
***sample contains triethanolamine Most of the viscosity, pH and free formaldehyde data in Chart 3 are within expected ranges. However, some of the examples required further dilution to test dispersibility. Most of the above samples that did not need dilution contain 42-46% polymer bound and free DCD. One example (e.g., example #63) required additional dilution to achieve a total DCD with DMSO of 43-44%. Similarly, examples #90 and #91 represent adjusting examples #64 and #65 to achieve a total DCD with DMSO of 43-44%, and also achieved a ratio of polymer bound to free DCD ratios close to the 52:48 of other examples.

It was expected that examples produced with similar molar ratios would have similar dispersibility in water. It was also expected that water dispersibility would decrease as the DCD to formaldehyde ratio decreased which would result in an increase in polymer bound to free DCD ratio. Comparing the water dispersibility of examples 62 and 88 to examples 67 and 68 did not support this expectation. Without being bound by theory, it is believed that the variation in solubility is related to the cyano group's presence as well as the distribution of polymer molecular weight (i.e., if more of the higher molecular species are present, the water solubility is diminished). Reaction parameters such as catalyst versus non-catalyst, the temperature at which the catalyst is charged, the time and temperatures of the process conditions, the speed of removal of water either from the catalyst charge or from the by-product, water from the second reaction and the % of a NAPAOL in the reaction composition are believed to be the conditions that influence water solubility.

Example 104

To determine the percent retention of the cyano group present in the examples, an UV analytical procedure was ran in which a calculated concentration of total (polymer found and free) DCD for a number of examples was performed and a dilution of the examples were performed to reach a calculated concentration of total DCD of 8.7 ppm using a isopropanol/water solvent system.

Procedure:
1) A UV spectrophotometer, DU Beckman 640, was utilized to determine the absorbance at specific UV wavelength of a diluted sample that was contained in a 10 mm Quartz Cuvette
2) A blank was prepared that included water, propanol and NAPAOL in the amounts present in the dilution of an example to 8.7 ppm of total DCD.
3) A standard curve was plotted for UV absorbance for known concentrations of DCD solutions of 8.7 ppm, 8.4 ppm, 8.0 ppm and 7.6 ppm representing respectively 43.5%, 42%, 40% and 38% DCD in solution. FIG. 1 is the plot of DCD concentration versus UV absorbance @ 211-216 nm.
4) The calculated concentration of examples was adjusted to a 43.5% level during the dilution process as shown in Chart 4:

CHART 4

| Example # | Calculated total DCD | Dil 1 Weight of Example | Dil 2 Total DCD conc | Dil 3 Total DCD conc | Dil 4 Total DCD Conc |
|---|---|---|---|---|---|
| 62 | 43.50% | 5.00 | 0.2175 | 0.0004350 | 0.0000087 |
| 88 | 42% | 5.18 | 0.2175 | 0.0004350 | 0.0000087 |
| 90 | 42.42% | 5.13 | 0.2175 | 0.0004350 | 0.0000087 |
| 91 | 42.42% | 5.13 | 0.2175 | 0.0004350 | 0.0000087 |
| 67 | 43.91% | 4.95 | 0.2175 | 0.0004350 | 0.0000087 |
| 68 | 44.94% | 4.84 | 0.2175 | 0.0004350 | 0.0000087 |
| 69 | 44.76% | 4.86 | 0.2175 | 0.0004350 | 0.0000087 |
| 71 | 45.70% | 4.76 | 0.2175 | 0.0004350 | 0.0000087 |
| 72 | 46.39% | 4.69 | 0.2175 | 0.0004350 | 0.0000087 |
| 73 | 42.13% | 5.16 | 0.2175 | 0.0004350 | 0.0000087 |
| 76 | 43.33% | 5.02 | 0.2175 | 0.0004350 | 0.0000087 |
| 78 | 46.62% | 4.67 | 0.2175 | 0.0004350 | 0.0000087 |
| 82 | 45.80% | 4.75 | 0.2175 | 0.0004350 | 0.0000087 |
| 83 | 45.80% | 4.75 | 0.2175 | 0.0004350 | 0.0000087 |

Dil-1: weight of example in 45 grams of 50/50 IPA/Water to yield concentration of total DCD of 4.35%
Dil-2: 5 grams of Dil 1, & 45 grams 50/50 IPA/Water
Dil-3: 50 grams Dil 2/450 Water
Dil-4: 2 gm Dil 3/100 mls Each sample dilution was placed in the Beckman DU 640 Spectrophotomer and read and recorded 4 times at UV wavelengths of 211-216 nm. Chart 5 shows the average of the three highest UV absorbance readings at 211-216 nm and the resulting sample's absorbance is compared to the concentration curve of the standard for DCD to estimate the sample's % total DCD.

CHART 5

| Example # | Average of UV Absorbance Readings | estimated Total DCD versus standard | Estimated % cyano-retained |
|---|---|---|---|
| Standard | 1.467 | 43.50% | |
| 62 | 1.395 | 41.80% | 96.09% |
| 88 | 1.334 | 40.55% | 93.22% |
| 90 | 1.305 | 39.95% | 91.84% |
| 91 | 1.278 | 39.40% | 90.57% |
| 67 | 1.365 | 41.20% | 94.71% |
| 68 | 1.313 | 40.15% | 92.30% |
| 69 | 1.343 | 40.80% | 93.79% |
| 71 | 1.331 | 40.60% | 93.33% |
| 72 | 1.316 | 40.25% | 92.53% |
| 73 | 1.378 | 41.50% | 95.40% |
| 76 | 1.400 | 42.05% | 96.67% |
| 78 | 1.331 | 40.50% | 93.10% |
| 82 | 1.426 | 42.50% | 97.70% |
| 83 | 1.281 | 39.50% | 90.80% |

Comparison of the data from example 62 and example 88 shows a significant drop in absorbance of example 88 indicating a loss of cyano-function. Examination of the reaction conditions for both examples reveals that even though example 62 was heated to 118° C., the methane sulfonic acid(MSA)/70% catalyst was charged at 42° C., whereas the reaction product for example 88 (example 63) was only heated to 95° C., the MSA/70% catalyst was charged at 85° C. Without being bound by theory, it is believed that the time, the temperature of the contents of the reaction vessel, the temperature at which the catalyst is introduced and the presence or absence of water have a major impact on cyano-function loss.

Examples 90, 91 and 73 are examples of low ratio DCD:Formaldehyde where the final ratio of polymer bound and free DCD are adjusted by the post reaction addition of free DCD. Examples 90 and 91 have low absorbance readings while example 73 has higher absorbance readings. Examples 90 and 91 were based on the reaction product of examples 64 and 65 respectively where the MSA/70% was charged at 85° C. and the reaction was heated to 110° C., removal of water was at the end of the reaction phase and the % composition of DMSO was around 45% during the reaction. Example 73 was at approximately 65% DMSO during the reaction phase and the MSA/70% was charged at 70° C. and the extra DCD was charged and the reactor placed under vacuum to remove the water by-product during the second reaction.

Examples 76, 82 and 83 are very similar in formulation and in process with the exception that example 76 has the catalyst MSA/70 charged to the reaction vessel at 80° C. while Example 82 utilizes the catalyst pTSA/100% and the catalyst is charged to the reaction vessel at 38° C. Without being bound by theory, it is believed that the catalyst MSA/70 contains some water, which degrades the cyano group. In comparison the catalyst pTSA/100% is substantially free of water and consequently does not degrade the available cyano groups. This theory is further supported by Example 83, which is example 82 with approximately 9-10% distilled water added. In both examples 82 and 83, the water is stripped out.

The UV absorption results show that utilizing a non-water containing catalyst that is charged at a low temperature results in higher absorption readings. Example 83 shows that the presence of water during reaction temperature results in lower UV absorption numbers.

Example 105

35 grams of DMSO was warmed to 45° C., then 15 grams of 2-chloro-6-trichloromethyl)pyridine was charged and the composition was mixed for 45 minutes until mixture was clear. 50 grams of Example 76 was charge and the new composition was mixed for 1 hour. The product was packaged. A check of the sample after 6 weeks of storage found it was still clear. Another sample of the composition was placed in an oven @ 50° C. and after three days was found to be stable.

Example 106

49.44 grams of example 76 were charged to reaction flask and placed under agitation. The pH was adjusted to 9.6 with NaOCH$_3$/25% and agitated for 15 minutes. 5.56 grams of paraformaldehyde were charged and composition was heated to 70° C. and held for five hours and then heated to 80° C. for 30 minutes. The composition was then cooled to 40° C. and held under agitation. The appearance of the composition was slightly hazy.

Example 107

To reactor 285 grams of molten urea was charged and then the vessel was deoxygenate 3 times by evacuating with vacuum and sparged with ammonia gas to slow degradation of urea under molten conditions. All sparging tubes and themometers had to be removed to prevent breakage and an a stainless steel agitator shaft and blade were utilized due to the difficulty in agitating granular urea. The urea was heated with agitation until molten and then the thermometer and sparge tube were re-inserted. The temperature reading was 148.3° C. and the molten urea was again sparged with ammonia gas. 15 grams of Example 106 were slowly charged to the molten urea while controlling the exotherm with charge rate and removing heating mantel. After 30 minutes, example 106 charge was completed and the composition was agitated at 145-155° C. under an ammonia atmosphere to 15 minutes. The composition had a slight hazy appearance and was then poured on a dimpled steel sheet, cooled and packaged for further evaluation.

Example 108

15.17 grams of dicyandiamide were charged to reaction flask that contained 29.0 grams of DMSO under agitation. The composition was heated to 80° C. and mixed at 80° C. until the dicyandiamide had dissolved. The composition was then cooled to 45° C. where 10.83 grams of paraformaldehyde were charged and mixed until a consistent slurry was formed.

Example 109

To reactor 285 grams of molten urea was charged and then the vessel was deoxygenate 3 times by evacuating with vacuum and sparged with ammonia gas to slow degradation of urea under molten conditions. All sparging tubes and themometers had to be removed to prevent breakage and an a stainless steel agitator shaft and blade were utilized due to the difficulty in agitating granular urea. The urea was heated with agitation until molten and then the thermometer and sparge tube were re-inserted. The temperature reading was 148.3° C. and the molten urea was again sparged with ammonia gas. 15 grams of Example 108 were slowly charged to the molten urea while controlling the exotherm with charge rate and removing heating mantel. After 30 minutes, example 106 charge was completed and the composition was agitated at 145-155° C. under an ammonia atmosphere to 15 minutes. The composition showed a slight milky appearance and was then poured on a dimpled steel sheet, cooled and packaged for further evaluation.

Example 110

49.48 grams of example 79 and 20 grams of DMSO were charged to reaction flask and placed under agitation. The pH was adjusted to 9.4 with NaOCH$_3$/25% and agitated for 15 minutes. 5.52 grams of paraformaldehyde were charged and composition was heated to 70° C. and held for five hours and then heated to 80° C. for 30 minutes. The composition was then cooled to 40° C. and held under agitation. The appearance of the composition was slightly hazier than example 106 and slightly viscous.

Example 111

To reactor 285 grams of molten urea was charged and then the vessel was deoxygenate 3 times by evacuating with vacuum and sparged with ammonia gas to slow degradation of urea under molten conditions. All sparging tubes and themometers had to be removed to prevent breakage and an a stainless steel agitator shaft and blade were utilized due to the difficulty in agitating granular urea. The urea was heated with agitation until molten and then the thermometer and sparge tube were re-inserted. The temperature reading was 148.3° C. and the molten urea was again sparged with ammonia gas. 15 grams of Example 110 were heated to 65° C. were slowly charged to the molten urea while controlling the exotherm with charge rate and removing heating mantel. After 30 minutes, example 106 charge was completed and the composition was agitated at 145-155° C. under an ammonia atmosphere to 15 minutes. The composition had a slight hazier appearance compared to example 107 and was then poured on a dimpled steel sheet, cooled and packaged for further evaluation.

Example 112

A number of the examples were tested for nitrification inhibition on urea. The experimental samples were applied to urea using standard overhead mixer with an anchor agitator. The amount of the sample to charge was determined by the specific gravity of the sample times the volumetric treatment level. For example:

Determining the amount of Example 76 to be charged at a rate of 3 quarts/ton of urea:

Specific gravity=1.163 gm/ml=9.68 lb/gal

At an application level of 3 quart/ton of urea=7.26 lbs of Example 76/2000 lbs of urea The application level would be 0.363% of Example 76

The 200 grams of urea was placed in a vessel, agitation was set so not to sling the urea out of the vessel and the calculated amount of the experimental sample was dripped onto the agitating urea. After completing the sample addition, the urea was agitated for an additional minute to insure uniform coverage.

The examples 62, 68, 73, 75 and 76 were adjusted to a calculated DCD level of 30% with DMSO and FD&C Blue #1 Food Color as shown in the Chart 6:

CHART 6

| Ingredients | DCD/30% | Ex-62/30% | Ex-68/30% | Ex-73/30% | Ex-75/30% | Ex-76/30% |
|---|---|---|---|---|---|---|
| DCD-34% | 88.3% | | | | | |
| DMSO | 10.5% | 29.73 | 31.94 | 27.54 | 18.49 | 27.27 |
| FD&C Blue #1 | 1.2% | 1.3 | 1.3 | 1.3 | 1.3 | 1.3 |
| Example 62 | | 68.97 | | | | |
| Example 68 | | | 66.76 | | | |
| Example 73 | | | | 71.16 | | |
| Example 75 | | | | | 80.21 | |
| Example 76 | | | | | | 71.43 |

Each sample was applied to 200 grams of urea at a 3 quart/ton application rate.

Example 113

Figure 6:
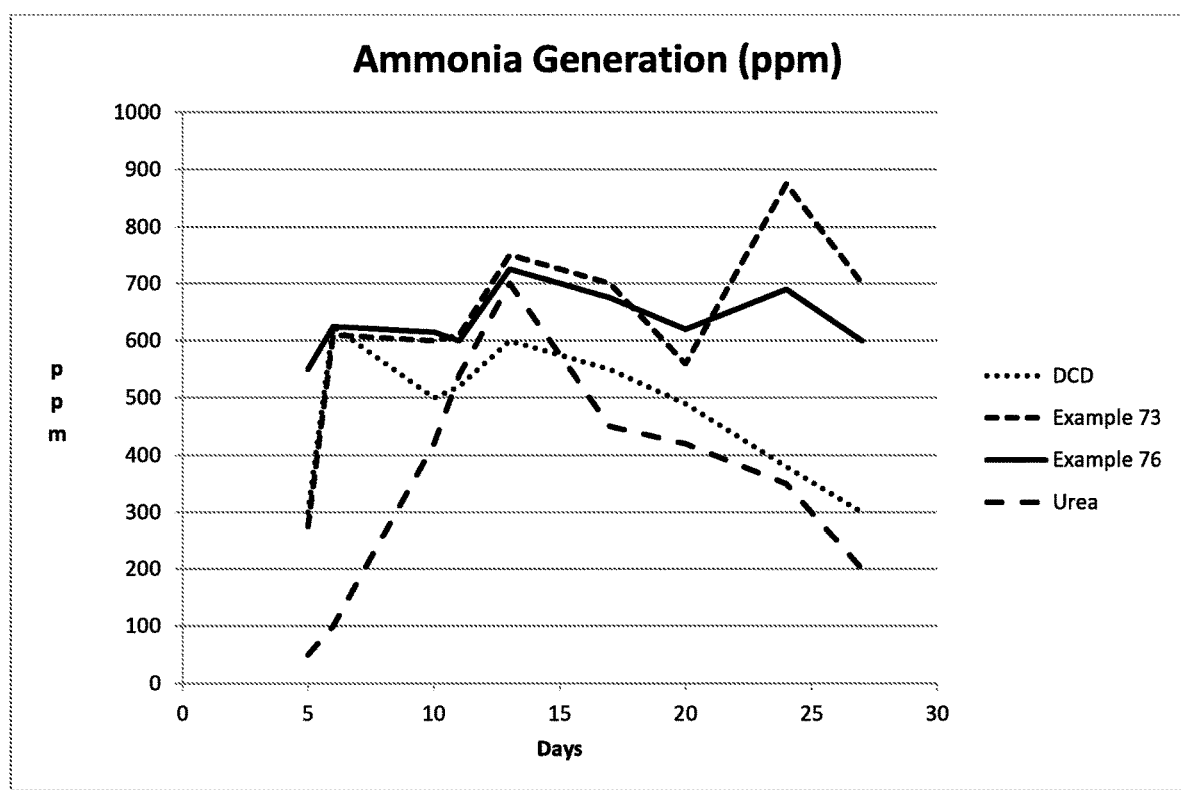
FIG. 6 is a graph of nitrification inhibition properties of Examples 73 and 76 versus dicyandiamide

In 143.5 cubic inch plastic containers with a hole in the side large enough for a Drager tube to be safely inserted, 200 grams of West Texas Soil (Estacado Clay Loam) with a moisture content of 37% and 75 grams of distilled water were added and mixed. The surface area of the soil was calculated to 47.8 sq inches. Exactly 1.1 grams of each urea sample was added to the surface of the soil and the plastic container and its hole were sealed. The headspace of each sealed container was analyzed for ppm ammonia by using a handheld Drager pump attached to the Drager tube which was inserted into the plastic container's hole and the pump was manually engaged 10 times. The readings were then recorded. Regardless of whether a reading of ppm ammonia was made each day on the samples' containers, each container was opened and fanned to insure that the reading of ammonia build up was for a 24 hour cycle. The results of test are in the Chart 7 which provides the data for graph listed as "FIG. 6" ((good nitrification inhibition results in high ammonia ppm readings):

CHART 7

| Sample ID on Urea | Ammonia Generated (ppm) Days | | | | | | | | |
|---|---|---|---|---|---|---|---|---|---|
| | 5 (ppm) | 6 (ppm) | 10 (ppm) | 11 (ppm) | 13 (ppm) | 17 (ppm) | 20 (ppm) | 24 (ppm) | 27 (ppm) |
| DCD/30% | 300 | 625 | 500 | 520 | 600 | 550 | 490 | 380 | 300 |
| Example 73/30% | 275 | 610 | 600 | 610 | 750 | 700 | 560 | 875 | 700 |
| Example 76/30% | 550 | 600 | 615 | 600 | 725 | 675 | 620 | 690 | 600 |
| Urea (untreated) | 50 | 100 | 420 | 540 | 700 | 450 | 420 | 350 | 200 |

A nitrate concentration analysis was performed on the soil after 30 days using a standard colormetric method in which a 1M KCl extraction of the soil is performed and is then passed through a copperized cadmium column. After diazotizing with sulfanilamide and followed by coupling with N-(1-naphthyl)ethylenediamine dihydrochloride, a color intensity is read at 520 nm. The Chart 8 contains the results of the analysis (good nitrification inhibition results in low nitrate ppm readings):

CHART 8

| Sample ID on urea | ppm of nitrate |
|---|---|
| DCD/30% | 9 |
| Example 73/30% | <1 |

CHART 8-continued

| Sample ID on urea | ppm of nitrate |
|---|---|
| Example 76/30% | <1 |
| Urea (untreated) | 81 |

Example 73 and Example 76 were combinations of DCD-formaldehyde oligomer with free DCD. While both were similar in composition, the free DCD was added to Example 73 post reaction while the free DCD was present during the reaction in Example 76. Because of the composition of the reactants in both examples, one would expect a broader oligomer/polymer molecular weight distribution in example 73 due to the 2.2:1 DCD to formaldehyde molar ratio while the excess DCD present in the reaction of example 76 due to the 3.5:1 DCD to formaldehyde ratio would result in a higher percentage of the methylene bis dicyandiamide oligomer. Results showed that both examples out performed DCD by itself.

Example 114

Figure 7:
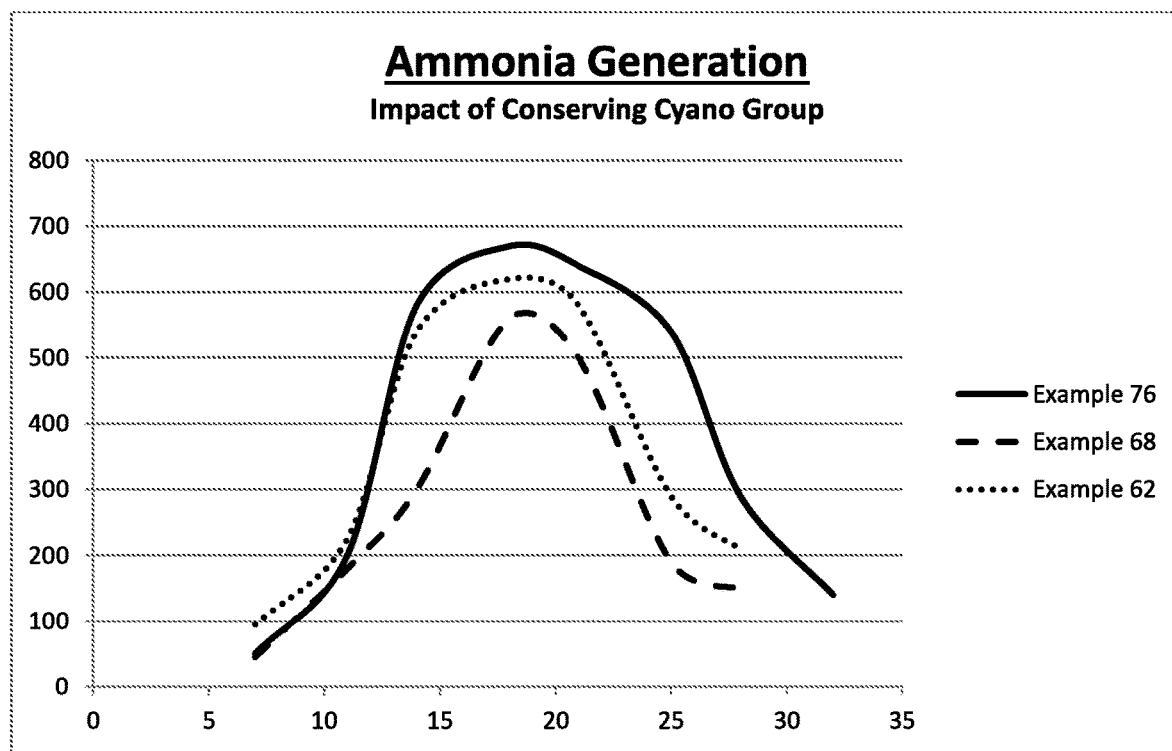
FIG. 7 is a graph on the impact of the presence of the cyano group on nitrification inhibition properties

In 66.1 cubic inch plastic containers with a hole in the side large enough for a Drager tube to be safely inserted, 200 grams of West Texas Soil (Estacado Clay Loam) with a moisture content of 37% and 75 grams of distilled water were added and mixed. The surface area of the soil was calculated to 33.1 sq inches. Exactly 0.75 grams of each urea sample was added to the surface of the soil and the plastic container and its hole were sealed. The headspace of each sealed container was analyzed for ppm ammonia by using a handheld Drager pump attached to the Drager tube which was inserted into the plastic container's hole and the pump was manually engaged 10 times. The readings were then recorded. Regardless of whether a reading of ppm ammonia was made each day on the samples' containers, each container was opened and fanned to insure that the reading of ammonia build up was for a 24 hour cycle. The results of test are in the Chart 9 below which provides the data for graph listed as "FIG. 7":

CHART 9

Ammonia Generated (ppm)
Impact of conserving cyano group

| Sample ID opn urea | *Estimated % cyano group retained | 7 (ppm) | 11 (ppm) | 14 (ppm) | 18 (ppm) | 21 (ppm) | 25 (ppm) | 28 (ppm) | 32 (ppm) |
|---|---|---|---|---|---|---|---|---|---|
| Example 62/30% | 96.09% | 95 | 225 | 540 | 620 | 580 | 290 | 210 | |
| Example 68/30% | 92.30% | 45 | 180 | 300 | 560 | 500 | 190 | 150 | |
| Example 76/30% | 96.67% | 50 | 200 | 580 | 670 | 640 | 540 | 290 | 140 |

*From Example #104/Chart #5

Example 62, Example 68 and Example 76 were combinations of DCD-formaldehyde oligomer with free DCD. All three were similar in composition and the free DCD was present during the reaction in in all three examples. Because of the composition of the reactants in the three examples are close, one would expect similar nitrification inhibition properties. However, the lower cyano group retention negatively impacted the nitrification inhibition of example 68.

Example 115

Figure 8:
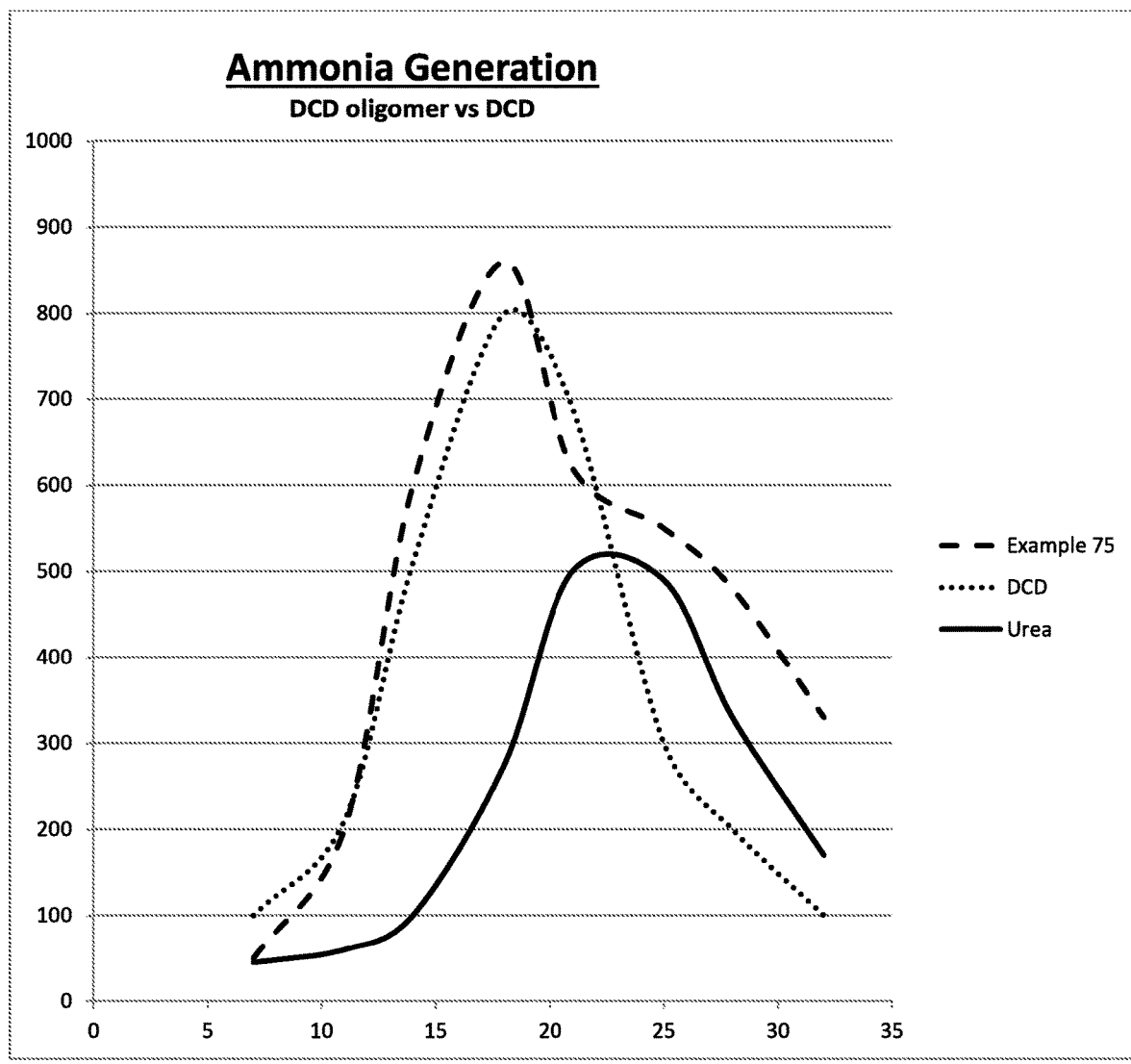
FIG. 8 is the nitrification inhibition property of Example 75 versus dicyandiamide.
Figure 9:
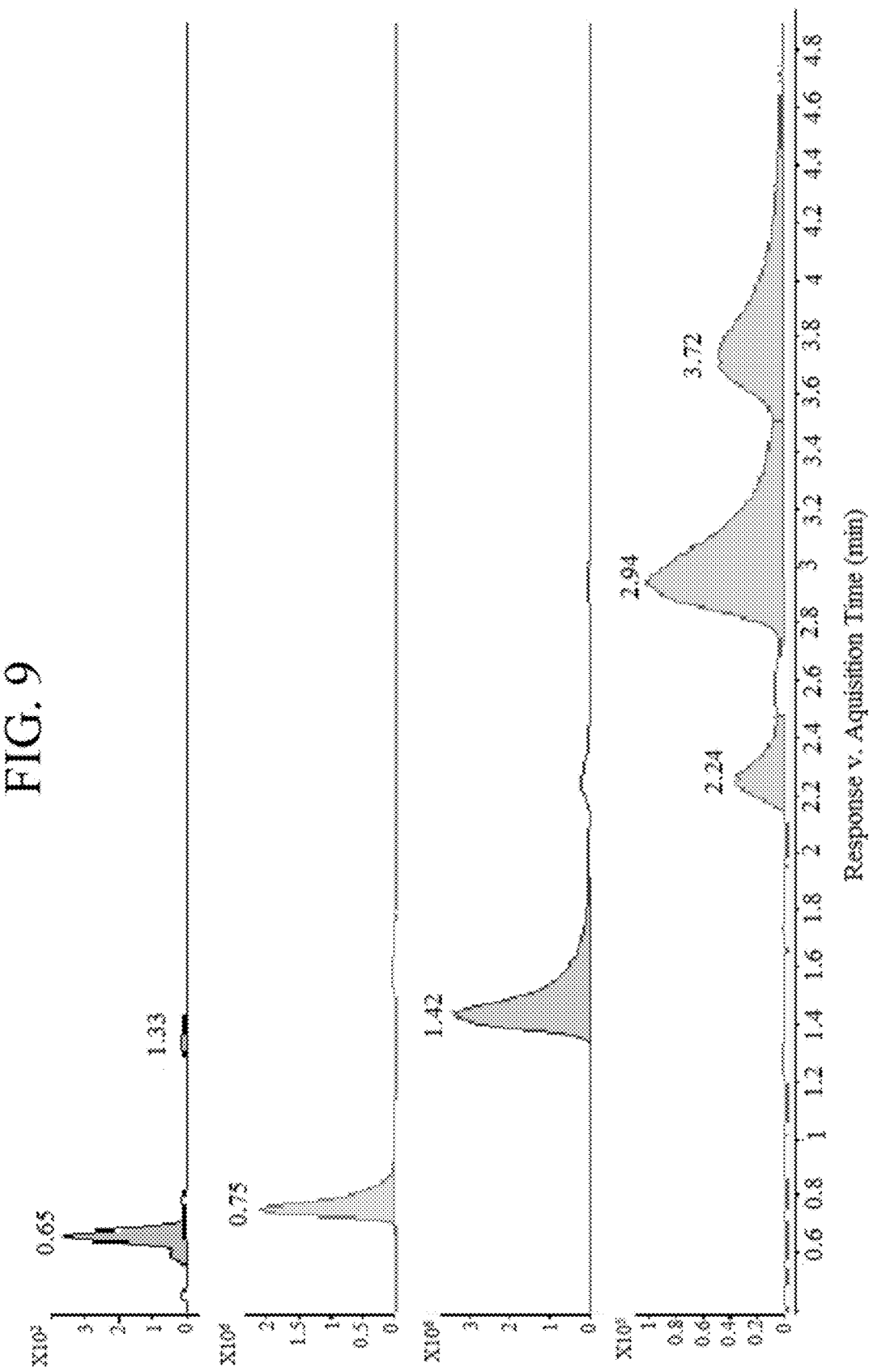
FIG. 9 is the chromatogram of Example 76.
Figure 10:
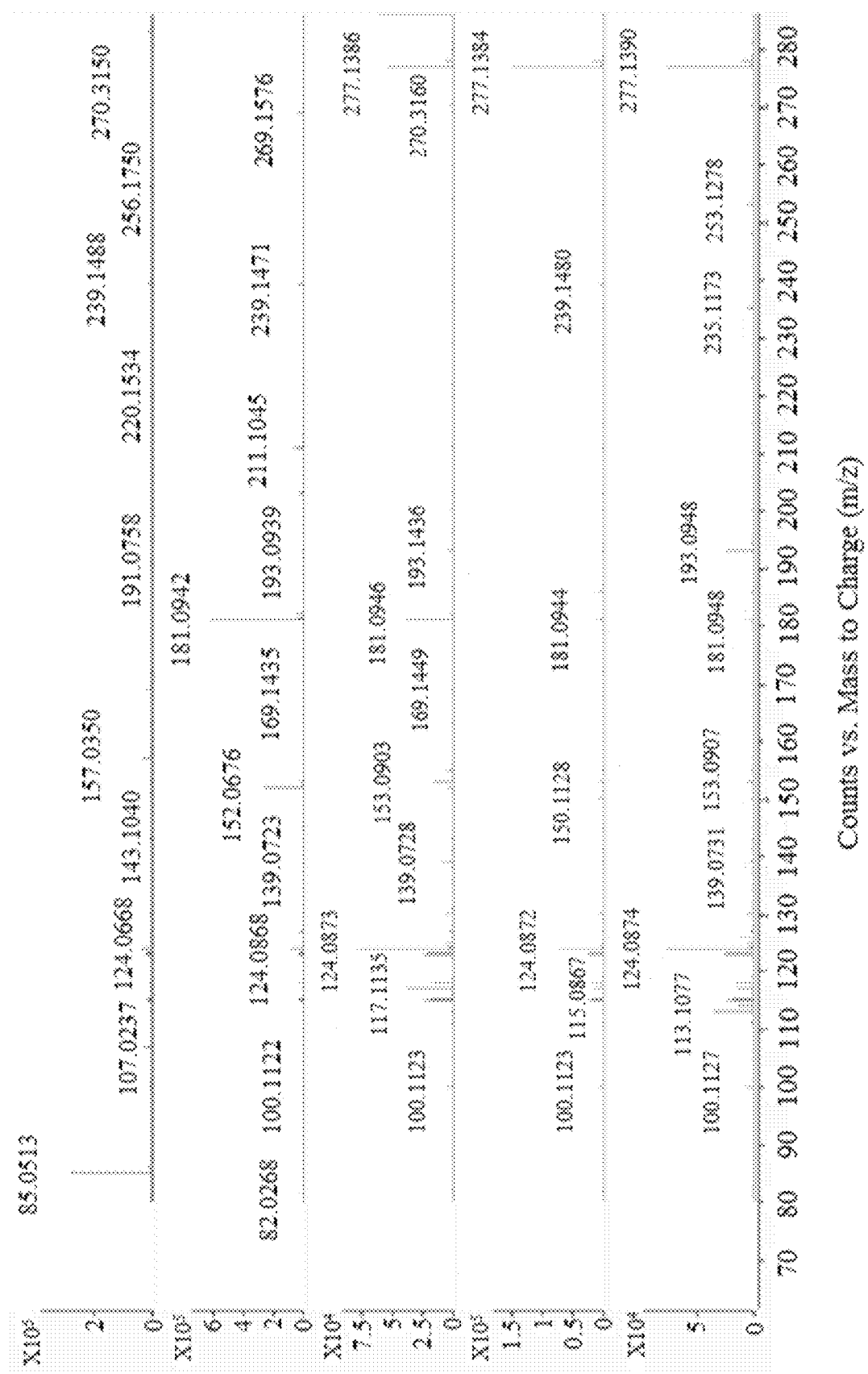
FIG. 10 is the mass spectra of Example 76.

In 66.1 cubic inch plastic containers with a hole in the side large enough for a Drager tube to be safely inserted, 200 grams of West Texas Soil (Estacado Clay Loam) with a moisture content of 37% and 75 grams of distilled water were added and mixed. The surface area of the soil was calculated to 33.1 sq inches. Exactly 0.75 grams of each urea sample was added to the surface of the soil and the plastic container and its hole were sealed. The headspace of each sealed container was analyzed for ppm ammonia by using a handheld Drager pump attached to the Drager tube which was inserted into the plastic container's hole and the pump was manually engaged 10 times. The readings were then recorded. Regardless of whether a reading of ppm ammonia was made each day on the samples' containers, each container was opened and fanned to insure that the reading of ammonia build up was for a 24 hour cycle. The results of test are in the Chart 10 below which provides the data for graph listed as "FIG. 8":

CHART 10

Ammonia Generated (ppm)
DCD-Formaldehyde oligomer versus DCD only

| Sample ID | 7 (ppm) | 11 (ppm) | 14 (ppm) | 18 (ppm) | 21 (ppm) | 25 (ppm) | 28 (ppm) | 32 (ppm) |
|---|---|---|---|---|---|---|---|---|
| DCD/30% | 100 | 210 | 510 | 800 | 690 | 300 | 200 | 100 |
| Example 75/30% | 50 | 200 | 600 | 860 | 620 | 550 | 480 | 330 |
| urea | 45 | 60 | 100 | 275 | 500 | 490 | 330 | 170 |

Example 75 is DCD-formaldehyde oligomer without the addition of free DCD. The composition of the reactants in example 75 is 2.2:1 molar ratio of DCD to formaldehyde. That molar ratio would lead one would expect some level of unreacted DCD to be present. While both DCD and Example 75 performed equivalently, at 25 days, the DCD performance drops off more substantially versus Example 75. The results show that the DCD-formaldehyde oligomers do have improved longevity versus DCD only.

Example 116

Analysis of the dicyandiamide-formaldehyde Reaction Products Utilizing DMSO as the NAPAOL by FTIR.

The reaction of formaldehyde with the amine groups of dicyandiamide results in a simple composition when the molar ratio of DCD to formaldehyde is 1.2:1 to 4.0:1. Under reaction parameters established in preparation of many of the examples yield a final product that contains DCD-formaldehyde adducts, unreacted DCD, DMSO and a trace of formaldehyde (<200 ppm). The DCD-formaldehyde adduct is DCD units crosslinked through a methylene bridge between two DCD amine groups.

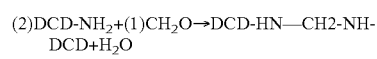

Although there is no major function group changes during the reaction, there is a modification of the amine groups and the introduction of N—CH$_2$—N group. Regions of interest are 3500-3100 cm$^{-1}$ (primary amine stretching and secondary amine stretching) and 1130 cm$^{-1}$ (N—CH$_2$—N vibration).

Chart 11 list the examples and their molar ratios of DCD to formaldehyde

CHART 11

| FIG. # | FTIR Scan ID | Molar ratio of DCD to Formaldehyde |
|---|---|---|
| #5 | DCD | NA |
| #2 | Example 76 | 3.5:1 |
| #3 | Example 74 | 2.2:1 |
| #4 | Example 79 | 1.2:1 |

Figure 2:
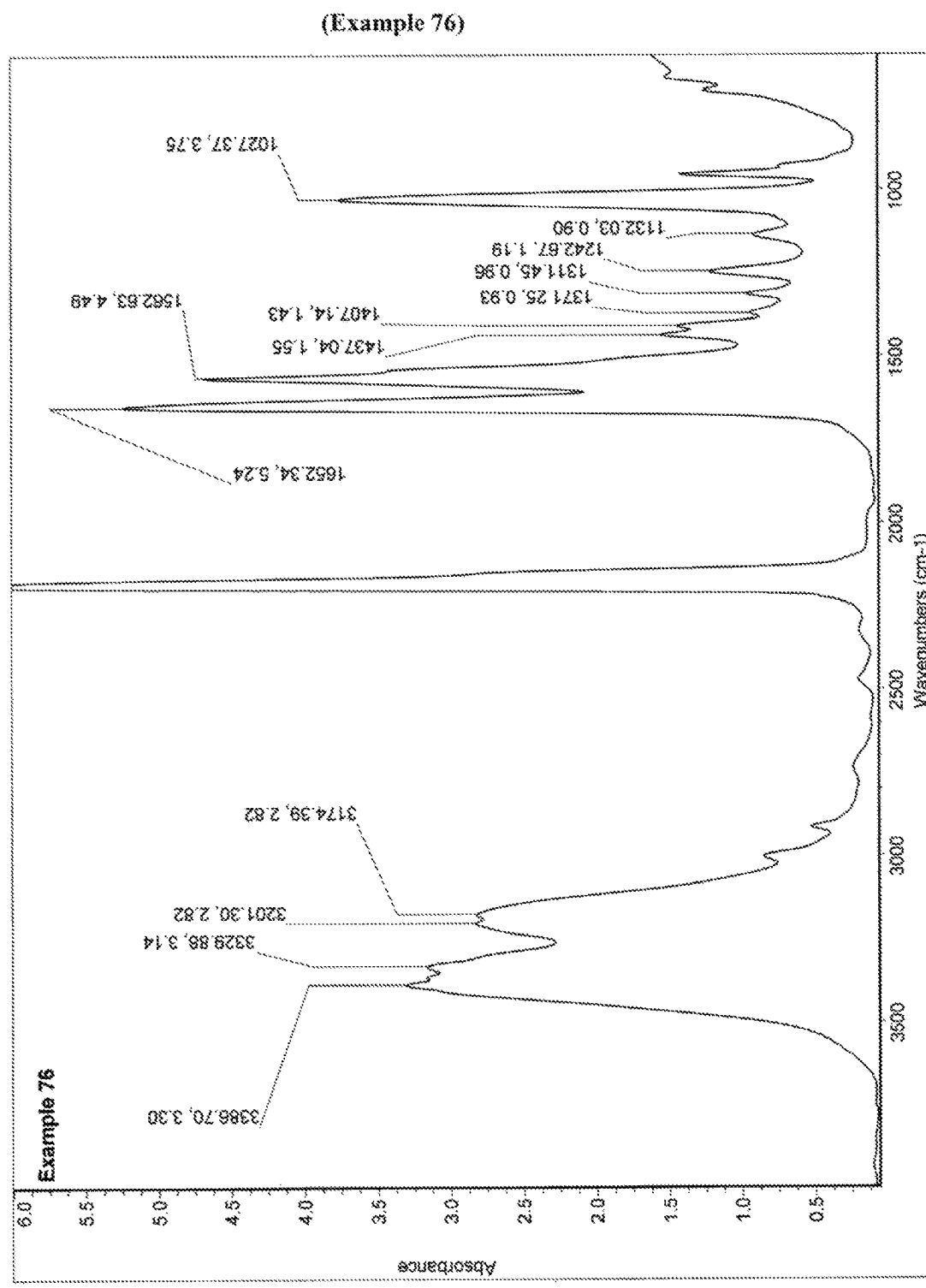
FIG. 2 is an FTIR scan of Example 76.
Figure 3:
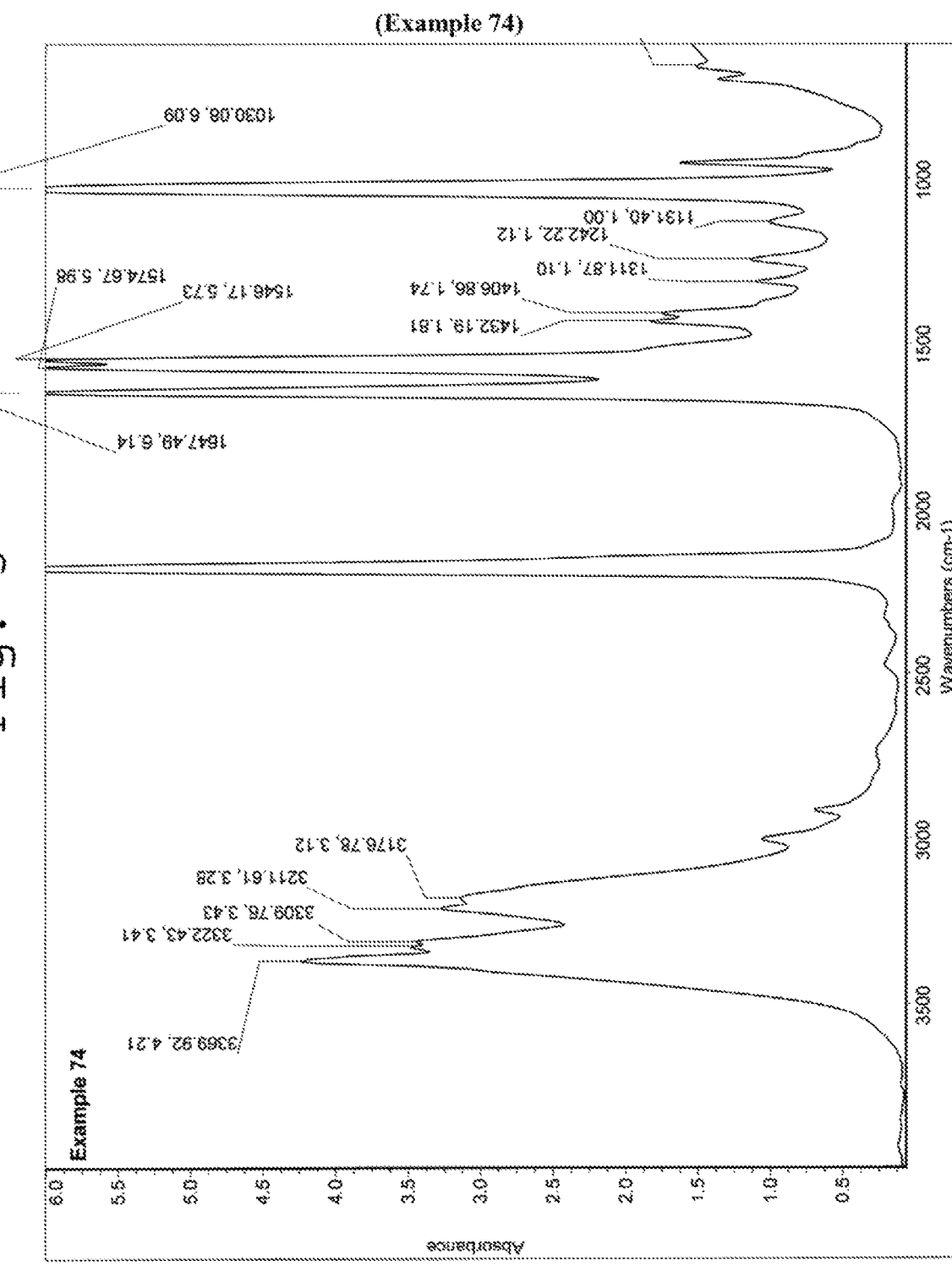
FIG. 3 is an FTIR scan of Example 74.
Figure 4:
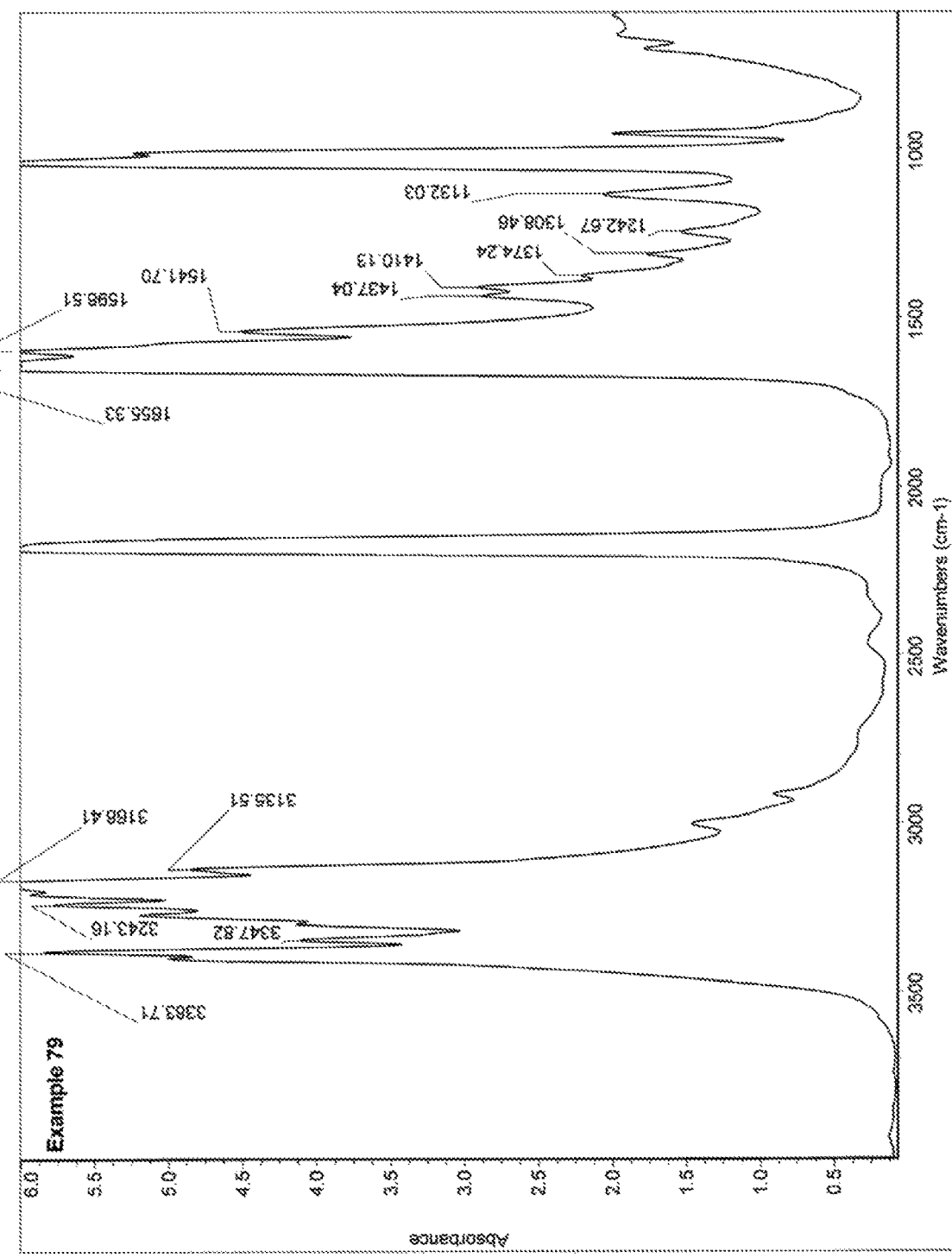
FIG. 4 is an FTIR scan of Example 79

Examination of the FTIRs in FIGS. 2-4 shows the deformation of the peaks in the region of 3400-3100 cm$^{-1}$ (N—H stretching) as changes in the molar ratios increases the weight percent of formaldehyde in the reaction resulting in the conversion of more primary amine to secondary amines.

Figure 5:
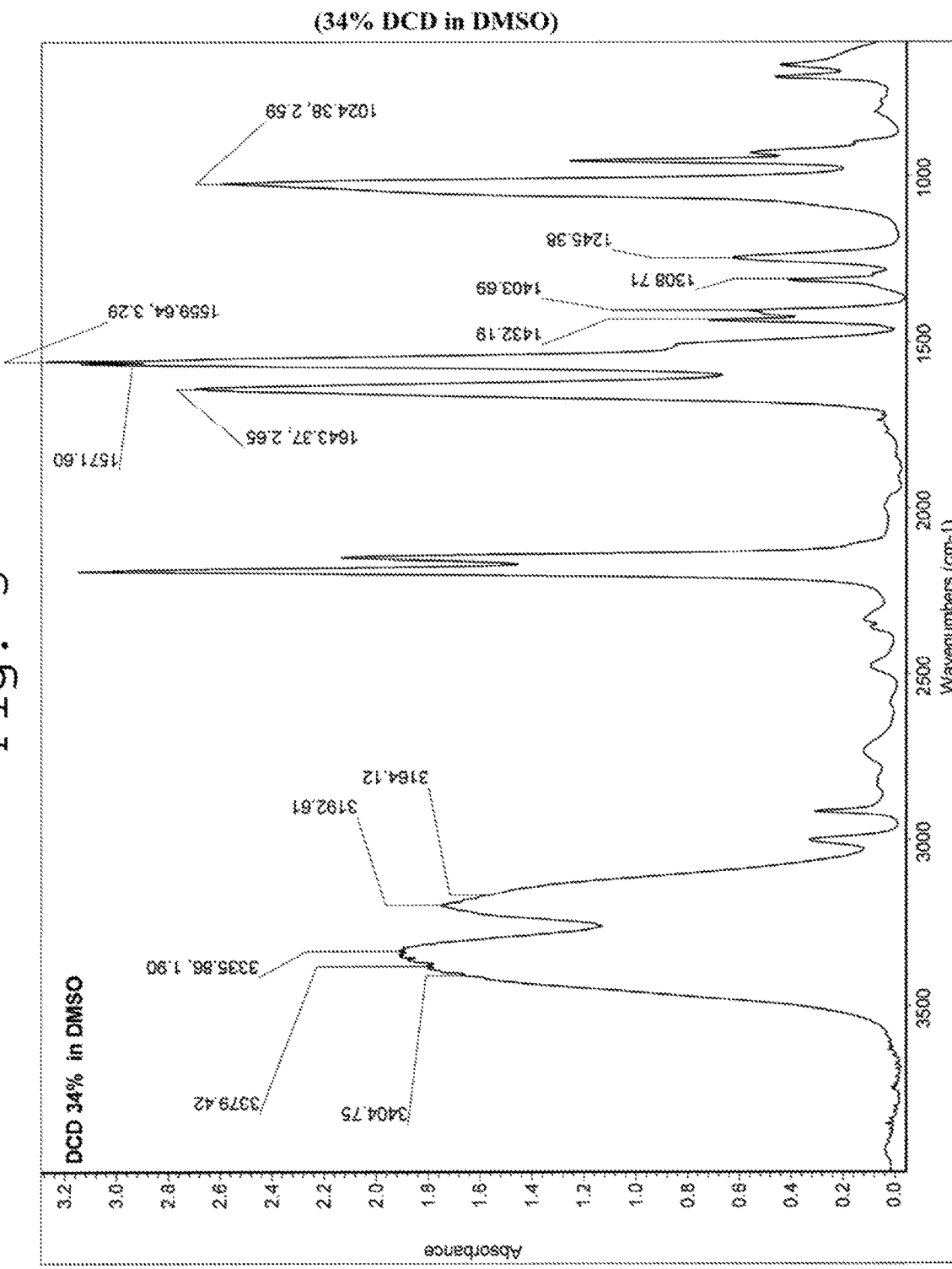
FIG. 5 is an FTIR scan of a 34% solution of Dicyandiamide in DMSO

In examination of FIG. 5 (DCD), there is no peak in the 1130-1135 cm-1 region. FIG. 2 (Example 76) shows a small peak at 1132 cm-1. The peak at 1132 cm-1 (N—C—N stretching) becomes more pronounced as the weight % of methylene bridges increases due to the increase in the weight percent of formaldehyde in the reaction. The examination of the peak at 1130-1135 cm-1 in FIG. 4 shows a more intensity versus FIG. 2

Comparing FIG. 5 (DCD) to FIG. 2-4 shows that the DCD has been modified and that a DCD-formaldehyde oligomer/polymer has been formed.

The presence of water degrades the available cyano groups. It should be clear that there are advantages to the instant invention when the reactions are performed in the absence of water. Using an aqueous medium limits applications to systems or processes not negatively impacted by the presence of water. The present invention has the advantage of not requiring other formaldehyde reactive constituents such urea and ammonia which are needed to impart water solubility to assist with the dicyandiamide (DCD) since DCD has a limited solubility in water of approximately 32 grams/liter at 20° C. The low DCD amounts in aqueous solution result in slower reactivity and low concentrations of the resulting polymers and oligomers. Performing the reaction in the absence of water does not generate the side products that result from the comparable reactions that are done in the presence of water. This is because when the reactions are performed in the absence of water, the additional components that are necessary when the reaction is performed in water are not present. For example, when the reaction is done in water with urea and ammonia, the resulting composition of the reaction product is a mixture of the following undesirable by-products: triazonyl-formaldehyde-DCD adducts, a urea-formaldehyde-DCD adduct and the desirable polymers and/or oligomers. When the reaction is performed in the presence of water, the composition of the formaldehyde reaction product comprises only about 0.1 to 10 wt. % of a DCD-formaldehyde-oligomer adduct based upon the weight of the nitrification inhibitor system. In contrast, when the reaction is performed in the absence of water, as in the present invention, much higher amounts of DCD-formaldehyde-oligomer adduct is generated.

Moreover, as shown by the above examples, biologically active agents can be added to the hydrophobic, biodegradable polymers that have been produced within the NOSDS, dimethyl sulfoxide and further can be added to the hydrophobic, biodegradable polymers that have been produced within the NOSDS, dimethyl sulfoxide and further formulated with protic and aprotic solvents to produce products that slow the dissolution of urea into water.

Example 117

Qualitative analysis by HPLC (High Pressure Liquid Chromatography) and MS (Mass Spectroscopy) were performed on example 76 and example 78 utilizing Agilent Technologies Model 6520 QTOF for MS and Agilent Technologies Model 1200 LS for HPLC with the following parameters:
Elution method: isocratic elution with 4% ammonium acetate buffer (1 mM) and 96% acetonitrile (ACN)
Flow rate: 0.5 ml per minute
Time: 5 minutes
Injection: 1 µL
Column: HILIC Acquity BEH Amide column (2.1×50 mm, 1.7µ)

Figure 11:
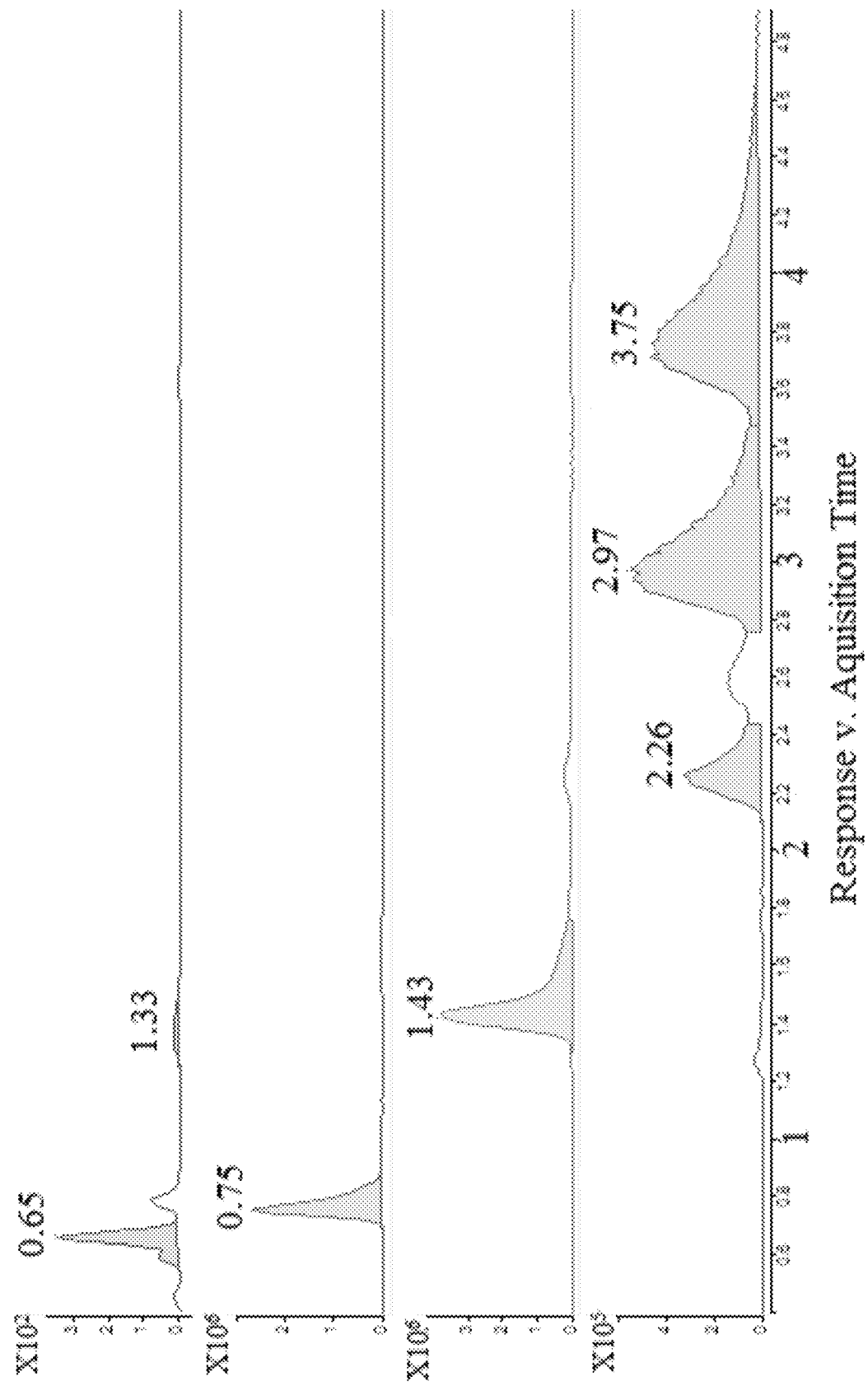
FIG. 11 is the chromatogram of Example 78.
Figure 12:
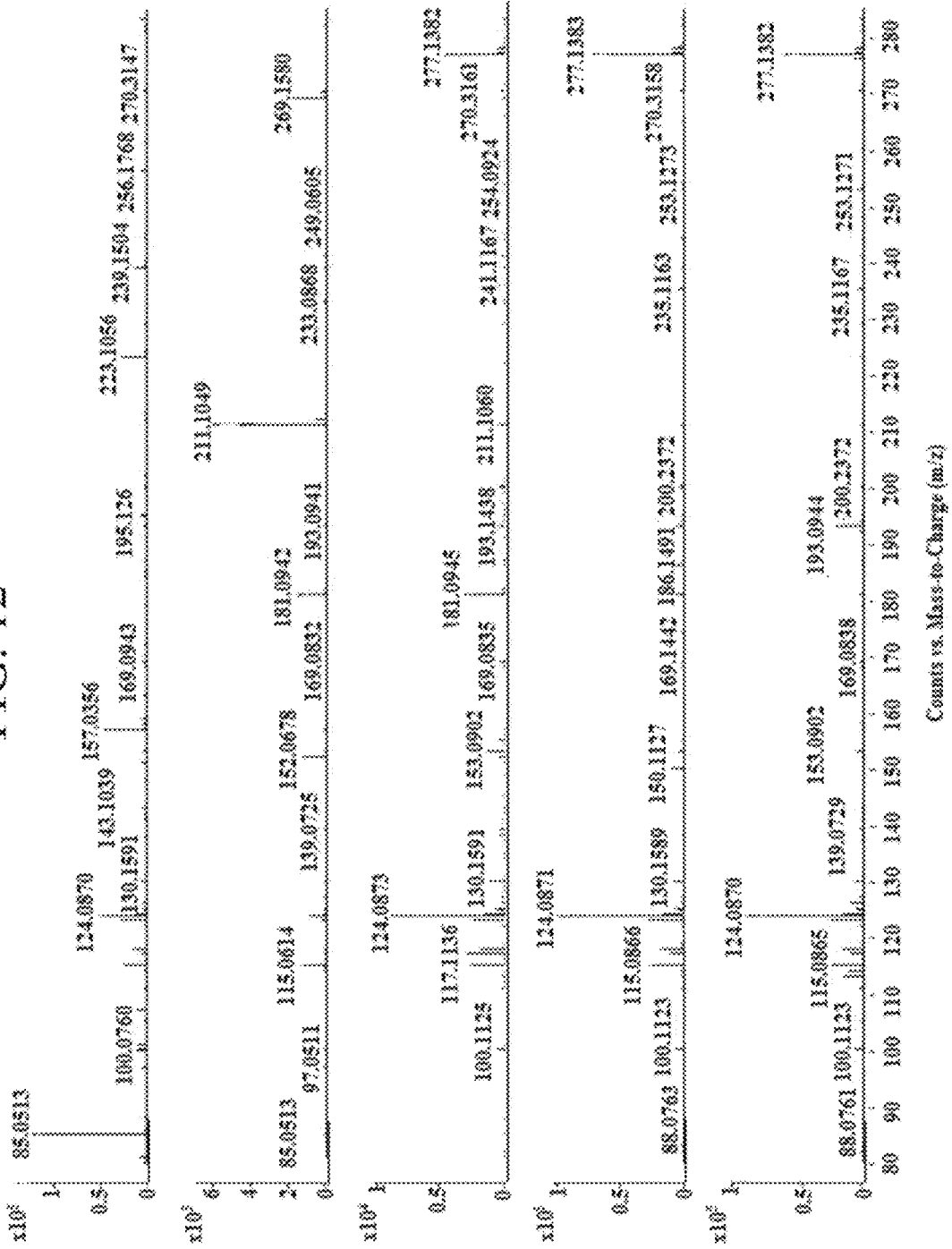
FIG. 12 is the mass spectra of Example 78.

FIG. 11 shows the chromatograph of example 78 while FIG. 12 shows the MS of the peaks in the chromatograph of example 78. The protonated molecule of DCD with a m/z 85.051 and the sodiated adduct of DCD with an m/z 107.033 were observed under electrospray ionization (ESI) conditions. The protonated form of the dimer (C$_5$H$_8$N$_8$) appears at m/z of 181.095 and a sodiated form at 203.076 and the protonated trimer (C$_8$H$_{12}$N$_{12}$) appears at m/z of 277.138 under ESI conditions. However, no sodium adduct was observed for the trimer. More DCD-methylol structures at m/z of 115.0867 and DCD-formaldehyde dimer-methylol structures at m/z of 211.1049 were also observed in the MS of example 78 versus example 76. Without being bound by theory, this is due to the higher ratio of formaldehyde to DCD. There are a number of unidentified small peaks within the MS, however, in ESI, different ions related to the analyte and solvent can be formed, so it is very difficult to identify all the masses in a spectrum and some peaks that relate to other molecular fragments. For example, the two m/z's at 169.0832 and at 193.0944 represent fragments from the polymer break at the methylene bridge of a tetramer. An intense response (peak) was also measured at an m/z of 124.0873. However this m/z is due to ACN, under ESI conditions, forming a trimer. The trimer show up under three peaks related to retention time of the chromatograph. This is due to the sticky nature of these compounds causing them to reside in the QTOF for some time or sticking to the walls of the tubing.

The results from qualitative analysis are summarized in Table 12.

TABLE 12

Retention and m/z Data for DCD and Samples.

| Sample source | Retention time(min) | mass-to-charge ratio | Protonated Structure DCD and DCD formaldehyde structure |
|---|---|---|---|
| DCD calibration standard | 0.76 | 85.0513 | DCD |
| | 0.75 | 107.0328 | * DCD-Na |
| Example 76 | 0.75 | 85.0513 | DCD |
| | 1.42 | 181.0942 | Dimer |
| | 2.24 | 181.0946 | Dimer |
| | 2.24 | 277.1386 | Timer |
| | 2.94 | 277.1384 | DCD Timer |
| | 2.94 | 115.0867 | DCD with methylol group |
| | 3.72 | 277.1390 | Timer |
| Example 78 | 0.75 | 85.0513 | DCD |
| | 1.43 | 181.0942 | Dimer |

TABLE 12-continued

Retention and m/z Data for DCD and Samples.

| Sample source | Retention time(min) | mass-to-charge ratio | Protonated Structure DCD and DCD formaldehyde structure |
|---|---|---|---|
| | 1.43 | 115.0614 | DCD with methylol group |
| | 1.43 | 211.1049 | Dimer with methylol group |
| | 2.26 | 181.0945 | Dimer |
| | 2.26 | 277.1382 | Timer |
| | 2.97 | 115.0866 | DCD with methylol group |
| | 2.97 | 277.1383 | Timer |
| | 3.75 | 115.0865 | DCD with methylol group |
| | 3.75 | 277.1382 | Timer |

* DCD-Na is not a protonated structure but a sodiated structure

TABLE 13

DAD peak areas from DAD and Mass Spec

| Sample | Molecule | DCD Monomer | | DCD Dimmer | | DCD Trimer | | |
|---|---|---|---|---|---|---|---|---|
| | | | | Example 76 (Coded 17K13) | | | | |
| 17K13 | m/2 | 85.0513 | 107.0327 | 181.0942 | 203.0764 | 277.1386 | 277.1384 | 277.139 |
| | EIC Area | 7584378 | 785355 | 4275011 | 1518747 | 434659 | 2241808 | 1291096 |
| | EIC SUM | 8369733 | | 5793758 | | 3967563 | | |
| | % Area sum | 46.16% | | 31.95% | | 21.88% | | |
| | | | | Example 78 (Coded 18C14) | | | | |
| 18C14 | m/2 | 85.0513 | 107.033 | 181.0942 | 203.0766 | 277.1386 | 277.1384 | 277.139 |
| | EIC Area | 6336128 | 744701 | 3469611 | 714232 | 306897 | 1237643 | 1191386 |
| | EIC SUM | 7080829 | | 4183843 | | 2735926 | | |
| | % Area sum | 50.58% | | 29.88% | | 19.54% | | |

EIC (Extracted Ion Chromatogram) was obtained by extracting the Total Ion Chromatogram at a specific exact m/z value. The normalized Ratio of DCD, Dimer and Trimer is obtained by dividing the area of the individual components by the sum of those three components and multiplying the product by 100 as in the below Equation:

Normalized Ratio of DCD=100*(Area DCD/(Area DCD+Area Dimer+Area Trimer)

Because of the limits of the MS that was utilized, all other DCD/formaldehyde oligomers with polymer/molecular weights greater than 300 will not generate an m/z measurement.

In an embodiment, the NOSDS not only provides the solvating property for the hydrophobic, biodegradable polymer but also serves as the delivery system for the hydrophobic, biodegradable polymers to the surface of fertilizer granules. In a variation, the NOSDS provides solvating properties to one of more biologically active agents selected from the group consisting of urease inhibitors, nitrification inhibitor(s), pesticide(s), herbicide(s), fungicides(s), and insecticide(s).

In an embodiment, incorporating within the NOSDS one of more biologically active agents selected from the group consisting of urease inhibitors, nitrification inhibitor(s), pesticide(s), herbicide(s), fungicides(s), and insecticide(s) with the biodegradable, hydrophobic polymers that are the reaction product of aldehyde(s) and nitrogen containing compounds will result in lower dissolution of these biologically active agents that are encapsulated within the hydrophobic film thereby improving performance by increasing the length of time these biologically active agents are available.

In an embodiment, the composition of the biodegradable, hydrophobic polymers that are the reaction product of aldehyde(s) and nitrogen containing compounds dispersed within a NOSDS can further comprise one or more urease inhibitors selected from the group consisting of aliphatic phosphoric triamide, phosphoramides and N-alkyl thiophosphoric triamides, (aminomethyl)phosphinic acids and their salts and aminomethyl (alkylaminomethyl)phosphinic acids and their salts. In a variation the urease inhibitor is N-(n-butyl) thiophosphoric triamide.

In an embodiment, the composition of the biodegradable, hydrophobic polymers that are the reaction product of aldehyde(s) and nitrogen containing compounds dispersed within a NOSDS can further comprise one or more nitrification inhibitors selected from the group consisting of 2-chloro-6-trichloromethyl)pyridine, 4-amino-1,2,4-6-triazole-HCl, 2,4-diamino-6-trichloromethyltriazine CL-1580, dicyandiamide (DCD), thiourea, 1-mercapto-1,2,4-triazole, ammonium thiosulfate, dimethylpyrazole organic and inorganic salts and 2-amino-4-chloro-6-methylpyrimidine In a variation the nitrification inhibitor is dicyandiamide.

In an embodiment the composition of the biodegradable, hydrophobic polymers that are the reaction product of aldehyde(s) and nitrogen containing compounds dispersed within a NOSDS can further comprise one or more nitrification inhibitors selected from the group consisting of 2-chloro-6-trichloromethyl)pyridine, 4-amino-1,2,4-6-triazole-HCl, 2,4-diamino-6-trichloromethyltriazine CL-1580, dicyandiamide (DCD), thiourea, 1-mercapto-1,2,4-triazole, ammonium thiosulfate, dimethylpyrazole organic and inorganic salts and 2-amino-4-chloro-6-methylpyrimidine and one or more urease inhibitors selected from the group consisting of aliphatic phosphoric triamide, phosphoramides and N-alkyl thiophosphoric triamides, (aminomethyl)phosphinic acids and their salts and aminomethyl (alkylaminomethyl) phosphinic acids and their salts.

In an embodiment, one can coat a granule of treated urea with the biodegradable, hydrophobic polymers that are the reaction product of aldehyde(s) and nitrogen containing compounds dispersed within a NOSDS. Treated urea is defined as a urea composition comprising urea and a biologically active agent added either through a coating application or added to the urea during the urea production process either in the melt portion or deposited to the urea during the formation of the urea granule when the urea is still hot. In a variation, the treated urea can be mixed with other fertilizer components and then coated with the biodegradable, hydrophobic polymers that are the reaction product of aldehyde(s) and nitrogen containing compounds. This will impart slower dissolution of these fertilizer components and urea into water because they have been encapsulated within the hydrophobic film, thereby improving performance by increasing the length of time the fertilizer is available.

In one embodiment, the composition of the liquid formulation comprises one or more biodegradable, hydrophobic polymers that are the reaction product of aldehyde(s) and nitrogen containing compounds and NOSDS. This composition is used to coat a dry granular urea, which is then applied to cropland and turf. The hydrophobic coating makes the urea more effective in providing nutrients for plant growth over an extended period of time. In a variation, the composition of the liquid formulation comprising urea and the biodegradable, hydrophobic polymers that are the reaction product of aldehyde(s) and nitrogen containing compounds and NOSDS further comprise one of more biologically active agents selected from the group consisting of urease inhibitors, nitrification inhibitor(s), pesticide(s), herbicide(s), fungicides(s), and insecticide(s) which when applied to cropland and turf makes the urea more effective in providing nutrients for plant growth over an extended period of time.

In an embodiment, biodegradable, hydrophobic polymers that are the reaction product of aldehyde(s) and nitrogen containing compounds can be produced by reacting the aldehyde(s) with the nitrogen containing compounds within the NOSDS. In a variation, the NOSDS comprises dimethyl sulfoxide.

In an embodiment, dicyandiamide can be dispersed within dimethyl sulfoxide and then reacted with paraformaldehyde in a molar ratio of 3-4 moles of dicyandiamide to one reactive unit of paraformaldehyde. This results in a composition comprised of dicyandiamide, that has reacted as well as some unreacted dicyandiamide. The composition unexpectedly contains DCD that is present at 35-60% by weight that will survive 3 freeze/thaw cycles (that is, the DCD does not crash out of solution). This is an unexpected result since the compositional percentage of dicyandiamide in a solution with dimethyl sulfoxide at a temperature of less than 35° C. was thought to not be able to exceed 35% by weight. In a variation, such a composition can also be applied to urea as a nitrification inhibitor providing extended nitrification inhibition due to the slow release of DCD into a plant growth media. In another variation, the composition can be added to an anhydrous ammonia formulation for sub-surface applications by injection of the anhydrous ammonia formula directly into the soil.

In an embodiment, the composition of the active hydrophobic coating agent comprises 5-60% of the biodegradable, hydrophobic polymers that are the reaction product of aldehyde(s) and nitrogen containing compounds and 95-40% of NOSDS. In a variation, the composition can further comprise 1 to 45% of biologically active agents.

In an embodiment, the method to make biodegradable, hydrophobic polymers that are the reaction product of aldehyde(s) and nitrogen containing compounds is a) dissolve the nitrogen containing compounds in an aprotic solvent at temperatures in the range of 30-110° C., then cool to 40-60° C. and insure that pH is in the range of 8-10, b) slowly add the aldehyde and allow the exotherm to be controlled either through charge rate or removing the heat of reaction through a cooling median, c) slowly heat the composition to 70-90° C. and hold for a period of time, d) cool the composition to 40-70° C., and slowly charge enough of an acid catalyst to drop the pH to 5-6.5 and let mix for an extended period of time to control the exotherm, e) slowly heat the composition to 90-115° C., f) after holding for a period of time, one can elect to place the batch under a vacuum to assist in removing water by-products, driving the reaction to more completion and removing any unreacted aldehyde and then cooling the batch. In a variation, one can charge protic and aprotic solvents to improve flow properties and storage stability. In another variation, one can charge a low molecular weight alcohol to improve and control the reaction. One can also cap unreacted methylene hydroxides through charging low molecular weight alcohols.

In an embodiment the % composition of the biodegradable, hydrophobic polymers that are the reaction product of aldehyde(s) and nitrogen containing compounds is stoichiometrically set to insure that there is no free formaldehyde or unreacted methylol groups remaining in the final product. In a variation, residual methylol groups can be capped by the addition of a low molecular weight alcohol such as but not limited to methanol, ethanol, propanol and butanol. In another variation, due to the penetration of urea by dimethyl sulfoxide, the alcohol capped methylol groups can be further reacted onto and with the surface of the urea utilizing temperature and catalysts known to those skilled in the art of reacting alcohol capped methylol groups, further improving the hydrophobic properties of the coating.

In an embodiment, the minimum application level of the liquid composition (of the biodegradable, hydrophobic polymers) is 3 quarts applied to one ton of urea. This mix provides extended time for plants to receive the nutrients from the treated fertilizer. In a variation, the liquid composition that is applied at a level of 3 quarts/ton of urea further comprises biologically active agents.

In an embodiment, the liquid composition of the biodegradable, hydrophobic polymers that are the reaction product of aldehyde(s) and nitrogen containing compounds dispersed within a NOSDS can further comprise monomers such as but not limited to tetramethoxy glycoluril or hexamethoxymethylmelamine. These additional monomers impart further crosslinking of the polymer to the surface of urea due to the penetration of urea by dimethyl sulfoxide. In a variation, Example 18 is a ready to use crosslinker dispersed in dimethyl sulfoxide that can be readily incorporated into the liquid composition.

In an embodiment, the water resistance of fertilizer coated with the liquid composition of the biodegradable, hydrophobic polymers that are the reaction product of aldehyde(s) and nitrogen containing compounds dispersed within a NOSDS can improve with time and with heat.

In an embodiment, a water resistant fertilizer is comprised of urea and the liquid composition of the biodegradable, hydrophobic polymers that are the reaction product of aldehyde(s) and nitrogen containing compounds dispersed within a NOSDS. In a variation the water resistant fertilizer is further comprised of one or more biologically active agents selected from the group consisting of urease inhibitors, nitrification inhibitor(s), pesticide(s), herbicide(s), fungicides(s), insecticide(s), flow modifiers and methylol capped monomers that are the reaction product of aldehyde(s) and nitrogen containing compounds. In a variation the flow modifier is a hydrophobic silica. In another variation, the one or more methylol capped monomers that are the reaction product of aldehyde(s) and nitrogen containing compounds are selected from the group consisting of tetramethoxy glycoluril, Tetra(methoxymethyl) urea, di(methoxymethyl) urea and hexamethoxymethylmelamine.

In an embodiment, the present invention relates to a composition comprising one or more biodegradable hydrophobic polymers of a molecular weight range of 50-200,000 Daltons and a Non-aqueous Organo Solvent Delivery System (NOSDS), wherein said composition is a stable dispersion ideally suited to coat man-made and/or natural fertilizer components, wherein the biodegradable, hydrophobic polymers comprise the reaction products of aldehyde(s) and nitrogen containing compounds and wherein the NOSDS is comprised of a) one or more protic solvents selected from the group consisting of: 1) an alcohol from the family of $C_{1-10}$ alkanols, 2) one or more polyols selected from the group consisting of trimethylol propane, trimethylol ethane, pentaerythritol, sorbitol, sorbitan, glucose, fructose, galactose, and glycerin, 3) one or more poly($C_{1-10}$ alkylene) glycols represented by the structure:

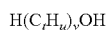

t is an integer: 1-10 u is an integer: 2-20 and v is an integer: 1-20, 4) one or more alkylene glycols selected from the group consisting of ethylene glycol, 1,3 propylene glycol, 1,2 propylene glycol, and butylene glycol, 5) isopropylidene glycerol 6) one or more alkylene glycol alkyl ethers selected from the group represented by the structure:

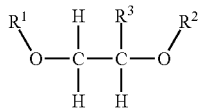

Where $R^1$ is: $CH_3$, $C_2H_5$, $C_3H_7$ or $C_4H_9$

Where $R^2$ is: H or the structure

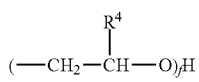

where $R^3$ is: H or $CH_3$ where $R^4$ is H and $CH_3$ and f is an integer between 1 and 15

7) one or more alkyl lactates selected from the group consisting of ethyl, propyl and butyl lactate, 8) one or more alkanolamines selected from the group represented by the structure:

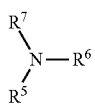

where $R^5$ is: $C_2H_4OR^8$ or $C_3H_6OH$ where $R^6$ is: H, $C_2H_4OR^8$ or $C_3H_6OH$ where $R^7$ is: H, $C_2H_4OR^8$ or $C_3H_6OH$ where $R^8$ is: $(C_2H_4O)_gH$ and g is an integer between 1-10 and 9) glycerol carbonate, b) and one or more aprotic solvents selected from the group consisting of 1) dimethyl sulfoxide and 2) dialkyl, diaryl, or alkylaryl sulfoxide(s) having the formula:

wherein $R_9$ and $R_{10}$ are each independently a $C_{1-6}$ alkylene group, an aryl group, or $C_{1-3}$ alkylenearyl group, or $R_9$ or $R_{10}$ with the sulfur to which they are attached form a 4 to 8 membered ring wherein $R_9$ and $R_{10}$ together are a $C_{1-6}$ alkylene group which optionally contains one or more atoms selected from the group consisting of O, S, Se, Te, N, and P in the ring and x is 1 or 2, 3) one or more alkylene carbonates selected from the group consisting of ethylene carbonate, propylene carbonate and butylene carbonate, 4) one or more polyols capped with acetate or formate wherein the polyol portion selected from the group consisting of ethylene glycol, 1,3 propylene glycol, 1,2 propylene glycol, butylene glycol, trimethylol propane, trimethylol ethane, pentaerythritol, sorbitol and sorbitan, glucose, fructose, galactose and glycerin, 5) one or more alkylene glycol alkyl ethers acetates selected from the group consisting of dipropylene glycol methyl ether acetate, tripropylene glycol methyl ether acetate, and tripropylene glycol butyl ether acetate and, 6) isophorone, 7) one or more diesters selected from the group consisting of dimethylsuccinate, dimethyl adipate, diethyl glutarate, and dimethyl glutarate, 8) dimethylacetamide, 9) dimethylformamide, 10) dimethyl-2-imidazolidinone, 11) 1-Methyl-2-pyrrolidone, 12) hexamethylphosphoramide, 13) 1,2-dimethyloxyethane, 14) 2-methoxyethyl ether, 15)cyclohexylpyrrolidone and 16) limonene.

In an embodiment, the aldehyde(s) portion of biodegradable, hydrophobic polymers resulting from the reaction products of aldehyde(s) and nitrogen containing compounds comprise one or more aldehyde(s) selected from the group represented by the structure:

a)

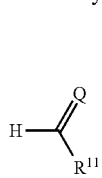

where Q is: O, S where $R^{11}$ is: —H, alkyl radical —$C_1H_3$ to —$C_6H_{13}$, —CH=$CH_2$, —$C_4H_3O$, —$C_7H_7$, —$C_6H_5$, —$C_6H_{11}$, CHO, $C_2H_3O$, $C_3H_5O$, $C_4H_7O$, $C_7H_5O$ or —$R^{12}O_2R^{13}$, where $R^{12}$ is: —C, —$C_2H_2$, —$C_3H_4$, —$C_4H_6$, —$C_5H_8$, —$C_6H_{10}$ where $R^{13}$ is: —H, $CH_3$, $C_2H_3$, $C_3H_7$, $C_4H_9$.

In an embodiment, the nitrogen containing compounds portion of biodegradable, hydrophobic polymers resulting from the reaction products of aldehyde(s) and nitrogen containing compounds comprise one or more nitrogen containing compounds selected from the group represented by the structures:

a)

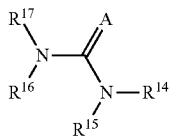

where A is: O, S
where $R^{14}$ is: —H, alkyl radical —$C_1H_3$ to —$C_6H_{13}$, —$C_6H_5$, —$CONH_2$, —$(CONH)_aNH_2$
where a is an integer: 1-10
where $R^{15}$ is: —H, alkyl radical —$C_1H_3$ to —$C_6H_{13}$, —$C_6H_5$, —$CONH_2$, —$(CONH)_bNH_2$
where b is an integer: 1-10
where $R^{16}$ is: —H, alkyl radical —$C_1H_3$ to —$C_6H_{13}$, —$C_6H_5$, —$CONH_2$, —$(CONH)_cNH_2$
where c is an integer: 1-10
where $R^{17}$ is: —H, alkyl radical —$C_1H_3$ to —$C_6H_{13}$, —$C_6H_5$, —$CONH_2$, —$(CONH)_dNH_2$
where d is an integer: 1-10, b)

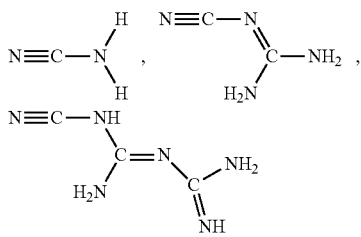

and their tautomeric forms, c)

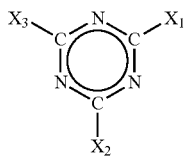

where $X_1$ is: —$NHR^{18}$, —H, —OH, —$C_6H_5$, —$N(CH_3)_2$, —$CH_3$
where $R^{18}$ is: H, an alkyl radical —$CH_3$ to —$C_{12}H_{25}$, —$C_2H_4OC_2H_4OH$, $C_2H_4OC_2H_4NH_2$, $C_3H_6$—$N(CH_3)_2$, $C_2H_4OH$, —$C_6H_5$
where $X_2$ is: —$NHR^{19}$, —H, —OH, —$C_6H_5$, —$N(CH_3)_2$, —$CH_3$
where $R^{19}$ is: H, an alkyl radical —$CH_3$ to —$C_{12}H_{25}$, —$C_2H_4OC_2H_4OH$, $C_2H_4OC_2H_4NH_2$, —$C_3H_6$—$N(CH_3)_2$, $C_2H_4OH$, —$C_6H_5$
where $X_3$ is: —$NHR^{20}$, —H, —OH, —$C_6H_5$, —$N(CH_3)_2$, —$CH_3$
where $R^{20}$ is: H, an alkyl radical —$CH_3$ to —$C_{12}H_{25}$, —$C_2H_4OC_2H_4OH$, $C_2H_4OC_2H_4NH_2$, —$C_3H_6$—$N(CH_3)_2$, $C_2H_4OH$, —$C_6H_5$ and d)
$NH_2CO$—$R^{21}$
where $R^{21}$ is an alkyl radical $CH_3$ to —$C_{17}H_{35}$.

In an embodiment, the composition of the biodegradable hydrophobic polymers comprise the reaction products of aldehyde(s) and nitrogen containing compounds which comprise one or more aldehydes selected from the group consisting of:

methanal, ethanal, propanal, butanal, pentanal, hexanal, methylethanal, methylpropanal, methylbutanal, phenylacetaldehyde, benzaldehyde, 2-propenal, 3-oxopropanoic, 2-methyl-3-oxopropanoic acid, 4-oxobutanoic acid, oxoacetic acid, 5-oxopentanoic acid, 6-oxohexanoic acid, 2-oxopropanal, cyclohexanal, furfural, methyl esters of 3-oxopropanoic, 2-methyl-3-oxopropanoic acid, 4-oxobutanoic acid, oxoacetic acid, 5-oxopentanoic acid and 6-oxohexanoic acid, ethandial, 1,3-propanedial, butanedial, pentanedial, phthalaldehyde or methanethial.

In an embodiment, the composition of the biodegradable hydrophobic polymers comprise the reaction products of aldehyde(s) and nitrogen containing compounds which comprise one or more nitrogen containing compounds comprise selected from the group consisting of:

urea, biuret, polyurea, thiourea, methylurea, dimethylurea, ethylurea, diethylurea, propylurea, dipropylurea, butylurea, dibutylurea, phenylurea, diphenyl urea, pentylurea, dipentylurea, hexyl urea, dihexyl urea, methylthiourea, dimethylthiourea, ethylthiourea, diethylthiourea, propylthiourea, diporpylthiourea, butylthiourea, dibutylthiourea, pentylthiourea, dipentylthiourea, hexylthiourea, dihexylthiourea, phenylthiourea, diphenylthiourea, cyanamide, dicyandiamide, tricyantriamide, melamine, hydroxy oxypentyl melamine, methylaminomelamine, dimethylaminopropylmelamine, 1,3,5-Triazine-2,4,6 triamine, 2,4-diamino-1,3,5-triazine, 2,4-diol-6-Amino-1,3,5-triazine, 2,4-Diamino-6-hydroxy-1,3,5-triazine, 2-Butylamino-4,6-diamino-1,3,5-triazine, 2,4-Diamino-6-methyl-1,3,5-triazine, 2,4-Diamino-6-dimethylamino-1,3,5-triazine, 2-Amino-1,3,5-triazine, ethanamide, propanamide, butanamide, pentanamide, hexanamide, heptanamide, octanamide, nonanamide, decanamide, dodecanamide, tetradecanamide, hexadecanamide, and octadecanamide.

In an embodiment, the composition of the biodegradable, hydrophobic polymer(s) further comprises, 0.1-5.0% of the polymer weight a) polyamines comprising of one or more members selected from the group consisting of:

ethylenediamine, diethylenetriamine, triethylenetetramine tetraethylenepentamine and aminoethylethanolamine, b) one or more polyol compounds selected form the group consisting of:

trimethylol propane, trimethylol ethane, pentaerythritol, sorbitol and sorbitan, glucose, fructose, galactose, and glycerin, poly($C_{1-10}$ alkylene) glycols, ethylene glycol, 1,3 propylene glycol, 1,2 propylene glycol, and butylene glycol, and c) one or more monoprotic compound(s) selected from the group consisting of:

diethylamine, diethanolamine, methylethanolamine, diisopropanolamine, methylispropylamine, cyclohexalamine, methanol, ethanol, butanol, hexanol, isopropylidene glycerol, tripropylene glycol methyl ether, tripropylene glycol butyl ether, dipropylene glycol butyl ether and tripropylene glycol butyl ether.

In an embodiment, the composition of the one or more biodegradable hydrophobic polymers is present in an amount that is between about 5-65% of a total composition.

In an embodiment, the composition of the biodegradable, hydrophobic polymers which comprises the reaction products of aldehyde(s) and nitrogen containing compounds dispersed in NOSDS further comprises one or more of surfactants, buffers, fragrance/odor masking agents, colorants, flow modifiers, silicas, hydrophobized silicas, one or more biologically active agents selected from the group consisting of a) urease inhibitors, nitrification inhibitors, pesticides, herbicides fungicides(s), and insecticide(s) and one or more catalysts selected from the group consisting of methane sulfonic acid, sulfuric acid, para-toluene sulfonic acid, phosphoric acid and methane phosphonic acid.

In an embodiment, the composition of the biodegradable, hydrophobic polymers comprise the reaction products of aldehyde(s) and nitrogen containing compounds dispersed in NOSDS wherein said aldehyde comprises paraformaldehyde. In an embodiment, said nitrogen containing compounds comprise dicyandiamide and said NOSDS is dimethyl sulfoxide. In a variation, the composition further comprises one or more of surfactants, buffers, fragrance/odor masking agents, colorants, flow modifiers, silicas, hydrophobized silicas, one or more biologically active agents selected from the group consisting of a) urease inhibitors, nitrification inhibitors, pesticides, herbicides fungicides(s), and insecticide(s) and one or more catalysts selected from the group consisting of methane sulfonic acid, sulfuric acid, para-toluene sulfonic acid, phosphoric acid and methane phosphonic acid.

In an embodiment, the method of use of the composition comprising dicyandiamide, paraformaldehyde and dimethyl sulfoxide that provides high levels of the nitrification inhibitor, dicyandiamide, is as a coating onto fertilizer granules. Alternatively and/or additionally, the composition can be added to anhydrous ammonia for direct injection into the soil to provide extended availability of nutrients for plant growth through inhibiting the conversion of ammonia to nitrate.

In an embodiment, the method for making the composition of the biodegradable, hydrophobic polymers which comprises the reaction products of aldehyde(s) and nitrogen containing compounds dispersed in NOSDS for application to fertilizer comprises adding biodegradable hydrophobic polymers that are the reaction product of aldehydes and nitrogen containing compound powders to the NOSDS under agitation at temperatures of 15-140° C., and optionally using a high shear mixer to reduce viscosity of the mixture.

In an embodiment, the present invention relates to a method for making the composition of the biodegradable, hydrophobic polymers which comprises the reaction products of aldehyde(s) and nitrogen containing compounds dispersed in NOSDS for application to fertilizer. In a variation, the method comprises adding a) biodegradable hydrophobic polymers that involves the reaction of aldehydes and nitrogen containing compound that are pre-dispersed in a liquid with undesirable properties such as flash point, health, shipping or environmental hazards and/or destabilize components of fertilizer or additives to the fertilizer to b) a NOSDS in which the liquid is displaced through differential boiling points by temperature and/or reduced pressure.

In an embodiment, the present invention relates to a method for making the composition of the biodegradable, hydrophobic polymers which comprises the reaction products of aldehyde(s) and nitrogen containing compounds dispersed in NOSDS for application to fertilizer comprised of procuring 1) one or more aldehydes represented by the structure:

a)

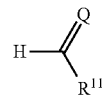

where Q is: O, S
where $R^{11}$ is: —H, alkyl radical —$C_1H_3$ to —$C_6H_{13}$, —CH=$CH_2$, —$C_4H_3O$, —$C_7H_7$, —$C_6H_5$, —$C_6H_{11}$, CHO, $C_2H_3O$, $C_3H_5O$, $C_4H_7O$, $C_7H_5O$ or —$R^{12}O_2R^{13}$,
where $R^{12}$ is: —C, —$C_2H_2$, —$C_3H_4$, —$C_4H_6$, —$C_5H_8$, —$C_6H_{10}$
where $R^{13}$ is: —H, $CH_3$, $C_2H_3$, $C_3H_7$, $C_4H_9$ and reacting said aldehydes with 2) one or more nitrogen containing compounds selected from the group represented by the structures:

a)

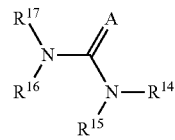

where A is: O, S
where $R^{14}$ is: —H, alkyl radical —$C_1H_3$ to —$C_6H_{13}$, —$C_6H_5$, —$CONH_2$, —$(CONH)_aNH_2$
where a is an integer: 1-10
where $R^{15}$ is: —H, alkyl radical —$C_1H_3$ to —$C_6H_{13}$, —$C_6H_5$, —$CONH_2$, —$(CONH)_bNH_2$
where b is an integer: 1-10
where $R^{16}$ is: —H, alkyl radical —$C_1H_3$ to —$C_6H_{13}$, —$C_6H_5$, —$CONH_2$, —$(CONH)_cNH_2$
where c is an integer: 1-10
where $R^{17}$ is: —H, alkyl radical —$C_1H_3$ to —$C_6H_{13}$, —$C_6H_5$, —$CONH_2$, —$(CONH)_dNH_2$
where d is an integer: 1-10, b)

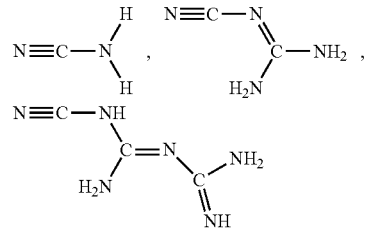

and their tautomeric forms, c)

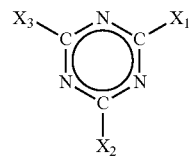

where $X_1$ is: —$NHR^{18}$, —H, —OH, —$C_6H_5$, —$N(CH_3)_2$, —$CH_3$ where $R^{18}$ is: H, an alkyl radical —$CH_3$ to —$C_{12}H_{25}$, —$C_2H_4OC_2H_4OH$, $C_2H_4OC_2H_4NH_2$, $C_3H_6$—$N(CH_3)_2$, $C_2H_4OH$, —$C_6H_5$ where $X_2$ is: —$NHR^{19}$, —H, —OH, —$C_6H_5$, —$N(CH_3)_2$, —$CH_3$ where $R^{19}$ is: H, an alkyl radical —$CH_3$ to —$C_{12}H_{25}$, —$C_2H_4OC_2H_4OH$, $C_2H_4OC_2H_4NH_2$, —$C_3H_6$—N$(CH_3)_2$, $C_2H_4OH$, —$C_6H_5$ where $X_3$ is: —$NHR^{20}$, —H, —OH, —$C_6H_5$, —$N(CH_3)_2$, —$CH_3$ where $R^{20}$ is: H, an alkyl radical —$CH_3$ to —$C_{12}H_{25}$, —$C_2H_4OC_2H_4OH$, $C_2H_4OC_2H_4NH_2$, —$C_3H_6$—N$(CH_3)_2$, $C_2H_4OH$, —$C_6H_5$ and d)

$NH_2CO$—$R^{21}$ where $R^{21}$ is an alkyl radical $CH_3$ to —$C_{17}H_{35}$ 3) dispersing the nitrogen containing compound(s) at temperatures of 10-140° C. into a non-aqueous organo solvent delivery system (NOSDS), wherein the NOSDS comprises one or more aprotic solvents selected from the group consisting of 1) dimethyl sulfoxide and 2) dialkyl, diaryl, or alkylaryl sulfoxide(s) having the formula:

$R_9S(O)_xR_{10}$ wherein $R_9$ and $R_{10}$ are each independently a $C_{1-6}$ alkylene group, an aryl group, or $C_{1-3}$alkylenearyl group or $R_9$ and $R_{10}$ together with the sulfur to which they are attached form a 4 to 8 membered ring wherein $R_9$ and $R_{10}$ together are a $C_{1-6}$ alkylene group which optionally contains one or more atoms selected from the group consisting of O, S, Se, Te, N, and P in the ring and x is 1 or 2, and optionally further comprising one or more alkylene carbonates selected from the group consisting of ethylene carbonate, propylene carbonate and butylene carbonate, 4) one or more polyols capped with acetate or formate wherein the polyol portion selected from the group consisting of ethylene glycol, 1,3 propylene glycol, 1,2 propylene glycol, butylene glycol, trimethylol propane, trimethylol ethane, pentaerythritol, sorbitol and sorbitan, glucose, fructose, galactose and glycerin, 5) one or more alkylene glycol alkyl ethers acetates selected from the group consisting of dipropylene glycol methyl ether acetate, tripropylene glycol methyl ether acetate, and tripropylene glycol butyl ether acetate and, 6) isophorone, 7) one or more diesters selected from the group consisting of dimethylsuccinate, dimethyl adipate, diethyl glutarate, and dimethyl glutarate, 8) dimethylacetamide, 9) dimethylformamide, 10) dimethyl-2-imidazolidinone, 11) 1-Methyl-2-pyrrolidone, 12) hexamethylphosphoramide, 13) 1,2-dimethyloxyethane, 14) 2-methoxyethyl ether, 15) cyclohexylpyrrolidone and 16) limonene, 4) wherein said composition is cooled to 30-60° C. and the aldehydes are charged at a rate that controls the exotherm with 5-20° C. of the reaction temperature of 30-70° C. in a molar ratio of aldehyde to aldehyde reactive sites on the nitrogen containing compound of 0.10-0.90/1.0;

5) wherein the reaction is held at 30-70° C. and at a pH of 7.5-10.0 for 1 to 12 hours until the free formaldehyde is 40,000-5,000 ppm's; and 6) wherein the pH is adjusted to 4.0-6.5, and the reaction is heated to 70-115° C., 7) wherein the reactor is optionally placed under a vacuum with a nitrogen sparge of 0.1 mm to 200 mm and held until free formaldehyde is <700 ppm, and then the composition is cooled.

In an embodiment, the present invention relates to a process for applying the composition of the biodegradable, hydrophobic polymers said process comprising adding the reaction products of aldehyde(s) and nitrogen containing compounds dispersed in NOSDS to fertilizer granules. In an embodiment, the process comprises:

1) placing the fertilizer granules in blending equipment comprising one or more pieces of equipment selected from the group consisting of mixers, blenders and tumblers or on a conveyer belt 2) applying the composition to said fertilizer granules at a temperature of 15-130° C. through a metering or a spray injection system; and 3) mixing or spraying until the fertilizer granules show complete coverage.

In an embodiment, the present invention relates to a composition comprising one or more biodegradable hydrophobic polymers of a molecular weight range of 50-200,000 Daltons, a crosslinking agent and a Non-aqueous Organo Solvent Delivery System (NOSDS), wherein said composition is a stable dispersion ideally suited to coat man-made and/or natural fertilizer components, wherein the biodegradable, hydrophobic polymers comprise the reaction products of aldehyde(s) and nitrogen containing compounds and wherein the NOSDS is comprised of one or more aprotic solvents selected from the group consisting of 1) Dimethyl Sulfoxide and 2) dialkyl, diaryl, or alkylaryl sulfoxide(s) having the formula:

$R_9S(O)_xR_{10}$ wherein $R_9$ and $R_{10}$ are each independently a $C_{1-6}$ alkylene group, an aryl group, or $C_{1-3}$alkylenearyl group or $R_9$ and $R_{10}$ with the sulfur to which they are attached form a 4 to 8 membered ring wherein $R_9$ and $R_{10}$ together are a $C_{1-6}$ alkylene group which optionally contains one or more atoms selected from the group consisting of O, S, Se, Te, N, and P in the ring and x is 1 or 2, and optionally further comprising 3) one or more alkylene carbonates selected from the group consisting of ethylene carbonate, propylene carbonate and butylene carbonate, 4) one or more polyols capped with acetate or formate wherein the polyol portion selected from the group consisting of ethylene glycol, 1,3 propylene glycol, 1,2 propylene glycol, butylene glycol, trimethylol propane, trimethylol ethane, pentaerythritol, sorbitol and sorbitan, glucose, fructose, galactose and glycerin, 5) one or more alkylene glycol alkyl ethers acetates selected from the group consisting of dipropylene glycol methyl ether acetate, tripropylene glycol methyl ether acetate, and tripropylene glycol butyl ether acetate and, 6) isophorone, 7) one or more diesters selected from the group consisting of dimethylsuccinate, dimethyl adipate, diethyl glutarate, and dimethyl glutarate, 8) dimethylacetamide, 9) dimethylformamide, 10) dimethyl-2-imidazolidinone, 11) 1-Methyl-2-pyrrolidone, 12) hexamethylphosphoramide, 13) 1,2-dimethyloxyethane, 14) 2-methoxyethyl ether, 15)cyclohexylpyrrolidone and 16) limonene.

In a variation, the aldehyde(s) is comprised of one or more compounds represented by the structure:

where Q is: O, S
where $R^{11}$ is: —H, alkyl radical —$C_1H_3$ to —$C_6H_{13}$, —CH=$CH_2$, —$C_4H_3O$, —$C_7H_7$, —$C_6H_5$, —$C_6H_{11}$, CHO, $C_2H_3O$, $C_3H_5O$, $C_4H_7O$, $C_7H_5O$ or —$R^{12}O_2R^{13}$,
where $R^{12}$ is: —C, —$C_2H_2$, —$C_3H_4$, —$C_4H_6$, —$C_5H_8$, —$C_6H_{10}$
where $R^{13}$ is: —H, $CH_3$, $C_2H_3$, $C_3H_7$, $C_4H_9$
wherein the nitrogen containing compound comprises one or more compounds represented by the structures:

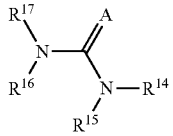

where A is: O, S
where $R^{14}$ is: —H, alkyl radical —$C_1H_3$ to —$C_6H_{13}$, —$C_6H_5$, —$CONH_2$, —$(CONH)_aNH_2$
where a is an integer: 1-10
where $R^{15}$ is: —H, alkyl radical —$C_1H_3$ to —$C_6H_{13}$, —$C_6H_5$, —$CONH_2$, —$(CONH)_bNH_2$
where b is an integer: 1-10
where $R^{16}$ is: —H, alkyl radical —$C_1H_3$ to —$C_6H_{13}$, —$C_6H_5$, —$CONH_2$, —$(CONH)_cNH_2$
where c is an integer: 1-10
where $R^{17}$ is: —H, alkyl radical —$C_1H_3$ to —$C_6H_{13}$, —$C_6H_5$, —$CONH_2$, —$(CONH)_dNH_2$
where d is an integer: 1-10,

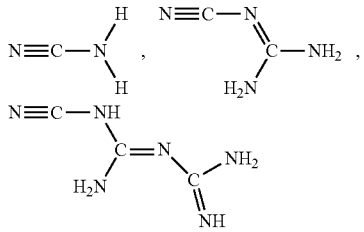

and their tautomeric forms,

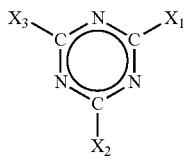

where $X_1$ is: —$NHR^{18}$, —H, —OH, —$C_6H_5$, —$N(CH_3)_2$, —$CH_3$
where $R^{18}$ is: H, an alkyl radical —$CH_3$ to —$C_{12}H_{25}$, —$C_2H_4OC_2H_4OH$, $C_2H_4OC_2H_4NH_2$, —$C_3H_6$—N$(CH_3)_2$, $C_2H_4OH$, —$C_6H_5$ where $X_2$ is: —$NHR^{19}$, —H, —OH, —$C_6H_5$, —$N(CH_3)_2$, —$CH_3$
where $R^{19}$ is: H, an alkyl radical —$CH_3$ to —$C_{12}H_{25}$, —$C_2H_4OC_2H_4OH$, $C_2H_4OC_2H_4NH_2$, —$C_3H_6$—N$(CH_3)_2$, $C_2H_4OH$, —$C_6H_5$
where $X_3$ is: —$NHR^{20}$, —H, —OH, —$C_6H_5$, —$N(CH_3)_2$, —$CH_3$
where $R^{20}$ is: H, an alkyl radical —$CH_3$ to —$C_{12}H_{25}$, —$C_2H_4OC_2H_4OH$, $C_2H_4OC_2H_4NH_2$, —$C_3H_6$—N$(CH_3)_2$, $C_2H_4OH$, —$C_6H_5$
and
$NH_2CO$—$R^{21}$
where $R^{21}$ is an alkyl radical $CH_3$ to —$C_{17}H_{35}$
wherein a crosslinking agent is comprised of one or more of compounds represented by the structures:

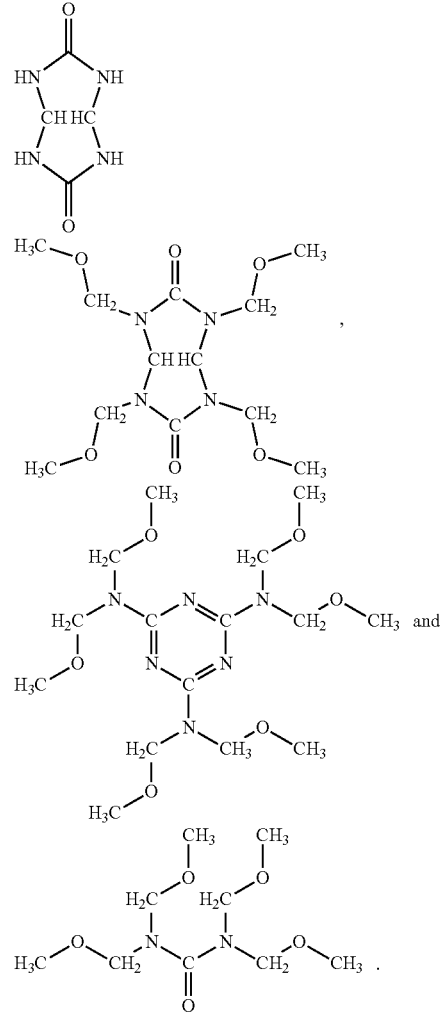

In an embodiment, the present invention relates to a composition of the biodegradable, hydrophobic polymers which comprises the reaction products of aldehyde(s) and nitrogen containing compounds dispersed in NOSDS wherein the one or more biodegradable hydrophobic polymers are present in an amount that is between about 5-65% of a total composition. In a variation, the crosslinking agent is present in an amount that is between about 0.1-10% of the total composition.

In an embodiment, the composition of the biodegradable, hydrophobic polymers which comprises the reaction products of aldehyde(s) and nitrogen containing compounds dispersed in NOSDS, further comprising one or more of surfactants, buffers, fragrance/odor masking agents, colorants, flow modifiers, silicas, hydrophobized silicas, one or more biologically active agents selected from the group consisting of a) urease inhibitors, nitrification inhibitors, pesticides, herbicides fungicides(s), and insecticide(s) and one or more catalysts selected from the group consisting of methane sulfonic acid, sulfuric acid, para-toluene sulfonic acid, phosphoric acid and methane phosphonic acid.

In an embodiment, the present invention relates to compositions and methods of making a liquid fertilizer additive of biodegradable polymeric and/or oligomeric nitrification inhibitors comprised of utilizing a non-aqueous polar, aprotic organo liquid (NAPAOL) as the reaction medium for the reaction of aldehyde(s) with cyano-containing nitrification inhibitors that have one or more aldehyde reactive groups selected from the group consisting of a) primary, b) secondary amines, c) amides, d) thiols, e) hydroxyls and f) phenols, wherein one or more of the following variants are met:
1. the reaction medium does not contain water as many nitrogen source application techniques are sensitive to the presence of moisture. The presence of water can alsolead to the degradation of the cyano-group to diaminomethylene urea under reaction conditions,
2. the reaction medium must be aprotic to prevent any solvent reaction with aldehydes,
3. the reacting materials and final product must be or become soluble in the reaction medium,
4. the reaction does not require aldehyde reactive, non-nitrification compounds (outside of catalyst) such as urea or ammonia in order to facilitate the reaction of aldehyde with a nitrification inhibitor,
5. the reaction medium can also serve as the solvent delivery system for applications to nitrogen sources utilizing one or more application techniques selected from the group consisting of a) coating the surface of fertilizer granules/prills, b) dispersing the liquid invention into an aqueous nitrogen source such as UAN, c) dispersing the liquid invention into ammonical subsurface injections, d) aiding in dissolving the liquid invention directly into molten nitrogen sources such as urea,
6. the reaction medium also serves as the solvent for incorporating biologically active agents and naturally occurring substances, substances produced by natural processes such as fermentation and/or extracts of naturally occurring substances (termed as biologics) such as but not limited one or more members selected from the group consisting of urease inhibitors, nitrification inhibitor(s), pesticide(s), herbicide(s), fungicides(s), and insecticide(s),
7. the reaction conditions are selected which favor the conservation of the cyano-group,
8. the final product is dispersed in a non-aqueous liquid,
9. the level of free aldehyde in the final product is less than 700 ppm.

In an embodiment, a method of making a liquid fertilizer additive of biodegradable polymeric and/or oligomeric nitrification inhibitors is comprised of utilizing NAPAOL as the reaction medium for the reaction of aldehyde(s) with cyano-containing nitrification inhibitors that have one or more aldehyde reactive groups selected from the group consisting of a) primary, b) secondary amines, c) amides, d) thiols, e) hydroxyls and f) phenols wherein the resulting product possesses one or more of the following improvements over reactions performed in an aqueous medium:
1. better control over polymer distribution resulting from the proper selection of process conditions,
2. lower water solubility results in slower dissolution of nitrogen sources and added biological actives once applied to the soil,
3. slow the loss of nitrification inhibition by reducing the nitrification inhibitors' volatility, limiting migration through the soil by increasing its molecular weight which lowers the nitrification inhibitors' water solubility,
4. extending the nitrification inhibitors' lifespan by utilizing incorporation into a polymer backbone which through biodegradation results in a slow release of incorporated nitrification inhibitors,
5. retaining some nitrification inhibition capability through formation of methylene bis nitrification inhibitor oligomers based on the reaction product of a total 2 moles of one or more nitrifications inhibitors that contain 1 to 2 aldehyde reactive groups reacted with one mole of aldehyde,
6. lower viscosity versus polymers formed in an aqueous medium which aides in coating solid nitrogen sources and adding to aqueous nitrogen sources as well as non-agricultural processes either further chemically modified or unmodified such as but not limited to industrial processes such as waste water color removal, paint detackification and treatment of paint or oily waste water and the treatment of leather,
7. able to maintain said biodegradable polymers at levels of 1-80% as liquids in a NAPAOL to temperatures down to at least 10° C. meaning that these compositions have improved shelf storage lives,
8. able to provide improved and even delivery of the liquid invention to the surface of fertilizer granules and solid nitrogen sources of said biodegradable polymeric/oligomeric nitrification inhibitors while not causing clumping of the granules,
9. able to safely incorporate into non-aqueous liquid nitrogen sources such as pressurized anhydrous ammonia gas,
10. able to incorporate directly into molten nitrogen sources a non-aqueous liquid product that results in better distribution of the said biodegradable polymeric/oligomeric nitrification inhibitors throughout the molten mass,
11. able to achieve higher concentration levels of the total of polymer bound and free nitrification inhibitors versus non-aqueous polar aprotic organo solvated free only nitrification inhibitors,
12. process yields a liquid product with an aldehyde content of <700 ppm.

In an embodiment, a method of making liquid fertilizer additives of biodegradable polymeric and/or oligomeric nitrification inhibitors is comprised of utilizing a NAPAOL as the reaction medium for the reaction of aldehyde(s) with cyano-containing nitrification inhibitors that have one or more aldehyde reactive groups selected from the group consisting of a) primary, b) secondary amines, c) amides, d) thiols, e) hydroxyls and f) phenols results in a product for direct application to nitrogen sources.

In an embodiment, a method of making liquid fertilizer additives of biodegradable polymeric and/or oligomeric nitrification inhibitors comprised of utilizing a NAPAOL as the reaction medium for the reaction of aldehyde(s) with cyano-containing nitrification inhibitors that have one or more aldehyde reactive groups selected from the group consisting of a) primary, b) secondary amines, c) amides, d) thiols, e) hydroxyls and f) phenols is designed wherein the molar ratio is set to ensure that the aldehyde to aldehyde reactive groups ratio available in said cyano-containing nitrification inhibitors is such that the aldehyde is completely reacted to its methylene form versus the methylol function.

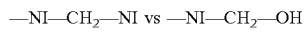

In a variation, the molar ratio of said aldehyde to said cyano-containing nitrification inhibitors is set with an excess of aldehyde reactive groups to ensure low free aldehyde products.

In an embodiment, a method of making fertilizer additives of biodegradable polymeric and/or oligomeric nitrification inhibitors is comprised of utilizing a NAPAOL as the reaction medium for the reaction of aldehyde(s) with cyano-containing nitrification inhibitors that have one or more aldehyde reactive groups selected from the group consisting of a) primary, b) secondary amines, c) amides, d) thiols, e) hydroxyls and f) phenols wherein to conserve the cyano-function of the nitrification inhibitors, one or more of the following reaction parameters are utilized: 1) limit the presence of water throughout the reaction, 2) minimize the temperature of any acid catalyst addition, and 3) minimize reaction time and/or temperature. In an embodiment, there are two reactions that occur. A first reaction is the aldehyde reaction with the amine and other groups as shown above and the second is the reaction of the methylol group with an aldehyde reactive group (as shown above), which is a reaction that can be accomplished in one embodiment by the addition of an acid catalyst. The reaction temperature should remain below about 70° C. for the addition of acid catalyst. It should be understood that as one increases the temperature, the time can be decreased and vice versa. In an embodiment, the time may range from about 8 hours to 32 hours. In an embodiment, it should be understood that water may be removed as the second reaction proceeds to further increase yield of the reaction product.

In an embodiment, a method of making fertilizer additives of biodegradable polymeric and/or oligomeric nitrification inhibitors is comprised of utilizing a NAPAOL as the reaction medium for the reaction of aldehyde(s) with cyano-containing nitrification inhibitors that have one or more aldehyde reactive groups selected from the group consisting of a) primary, b) secondary amines, c) amides, d) thiols, e) hydroxyls and f) phenols comprises the following steps:

A) procurement of
  1) one or more aldehydes represented by the structure:
    a)

wherein Q is: O, S
wherein $R^{11}$ is: —H, alkyl radical —$C_1H_3$ to —$C_6H_{13}$, —CH=$CH_2$, —$C_4H_3O$, —$C_7H_7$, —$C_6H_5$, —$C_6H_{11}$, CHO, $C_2H_3O$, $C_3H_5O$, $C_4H_7O$, $C_7H_5O$ or —$R^{12}O_2R^{13}$, wherein $R^{12}$ is: —C, —$C_2H_2$, —$C_3H_4$, —$C_4H_6$, —$C_5H_8$, —$C_6H_{10}$
wherein $R^{13}$ is: —H, $CH_3$, $C_2H_3$, $C_3H_7$, and $C_4H_9$
2) one or more cyano-containing nitrification inhibitors that have one or more aldehyde reactive groups selected from the group consisting of a) primary, b) secondary amines, c) amides, d) thiols, e) hydroxyls and f) phenols selected from the group consisting of:
  a) one or more cyano-compounds selected from the group represented by the structures

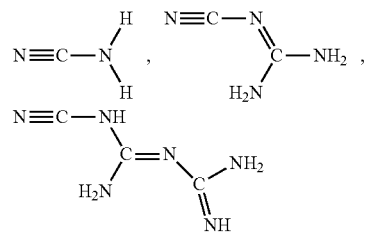

3) a non-aqueous polar aprotic organo liquid, wherein the non-aqueous polar, aprotic solvent (NAPAOL) is the reaction medium, which comprises one or more members selected from the group consisting of
  a) dimethyl sulfoxide
  b) and dialkyl, diaryl, or alkylaryl sulfoxide(s) having the formula:

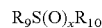

wherein $R_9$ and $R_{10}$ are each independently a $C_{1-6}$ alkylene group, an aryl group, or $C_{1-3}$alkylenearyl group or $R_9$ and $R_{10}$ together with the sulfur to which they are attached form a 4 to 8 membered ring wherein $R_9$ and $R_{10}$ together are a $C_{1-6}$ alkylene group which optionally contains one or more atoms selected from the group consisting of O, S, Se, Te, N, and P in the ring and x is 1 or 2.
  c) and one or more alkylene carbonates selected from the group consisting of ethylene carbonate, propylene carbonate and butylene carbonate d) 1-Methyl-2-pyrrolidone, e) one or more organo phosphorous liquids selected from the group consisting of hexamethylphosphoramide and one or more trialkylphosphates selected from the group represented by the formula.

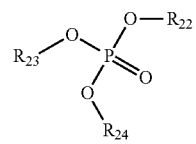

wherein:
  $R_{22}$ is alkyl radical —$C_1H_3$ to —$C_6H_{13}$
  $R_{23}$ is alkyl radical —$C_1H_3$ to —$C_6H_{13}$
  $R_{24}$ is alkyl radical —$C_1H_3$ to —$C_6H_{13}$
  f) 1,2-dimethyloxyethane, g) 2-methoxyethyl ether and h) cyclohexylpyrrolidone
B) a reaction vessel may be equipped with agitation, heating and cooling (hot oil systems are not recommended), riser, overhead condenser and a receiving vessel to capture reaction distillate, capable of a vacuum of 0.5-50 mm and sparging/sweeping with an inert gas such as but not limited to nitrogen and carbon dioxide C) charging said procured ingredients to said reactor by one or more steps selected from the group consisting of:
  a) charging said aldehydes, said cyano-nitrification inhibitors and said NAPAOL to said reaction vessel and start mixing
  b) charging said cyano-containing nitrification inhibitors and said NAPAOL to said reaction vessel, start mixing and heating mixture to 40-90° C., holding for 0-60 minutes at temperature, cooling down to 20-60° C. and then charging said aldehyde.
  c) charging said cyano-containing nitrification inhibitors and said NAPAOL to said reaction vessel, de-oxygenate the vessel by either sparging with an inert gas such as but not limited to nitrogen and carbon dioxide for a 15-60 minutes or by placing vessel under vacuum and breaking vacuum by sparging/sweeping vessel with an inert gas and repeating this exercised-oxygenation at least 3 times and then charging said aldehyde.

D) proceeding with the first reaction by one or more steps selected from the group consisting of:
  a) heating contents of the vessel to 50-90° C. and hold at temperature for 1-4 hours,
  b) heating contents of the vessel to 70-80° C. and hold at temperature for 1-4 hours
  c) heating contents of the vessel to 50-90 C and hold at temperature until contents are clear
  d) heating contents of the vessel to 70-80° C. and hold at temperature until contents are clear.

E) proceeding with the second reaction by one or more steps selected from the group consisting of:
  a) placing reaction vessel under a vacuum of 0.5-50 mm, increasing temperature to 90-120° C. and held under vacuum and at temperature until aldehyde content is 0-700 ppm.
  b) charging an acid catalyst such as but not limited to one or more members selected from the group consisting of methane sulfonic acid, sulfuric acid, para-toluene sulfonic acid phosphoric acid and methane phosphonic acid, placing reaction vessel under a vacuum of 0.5-50 mm, increasing temperature to 90-120° C. and hold under vacuum and at temperature until aldehyde content is 0-700 ppm. In a variation, cooling contents of reaction vessel, if necessary, to 20-60° C. before charging the acid catalyst F) terminating the reaction by one or more steps selected from the group consisting of:
  a) hard sparging reaction vessel contents with an inert gas to assist in removing residual aldehyde. Vacuum and hard sparge can be repeated to assist in removing aldehyde from the contents in the reaction vessel.
  b) Ensuring ppm formaldehyde is <700 ppm.
  c) cooling contents below 40° C. and off load
  d) charging a mild neutralizing agent such as triethanolamine to neutralize the acid catalyst.

In a variation, the acid catalyst is added in an amount that ensures that the pH of 5% by weight of the final product in aqueous solution will be greater than 7.0.

In an embodiment, a method of making liquid fertilizer additives of biodegradable polymeric and/or oligomeric nitrification inhibitors is comprised of utilizing a NAPAOL as the reaction medium for the reaction of aldehyde(s) with cyano-containing nitrification inhibitors that have one or more aldehyde reactive groups selected from the group consisting of a) primary, b) secondary amines, c) amides, d) thiols, e) hydroxyls and f) phenols comprises reacting cyano-containing nitrification inhibitors with aldehydes at a molar ratio of cyano-containing nitrification inhibitors' aldehyde reactive units to aldehyde units of 1:1. In an embodiment, using NAPAOL as the reaction medium results in a composition of wherein at least 70% or alternatively at least 90% of the total nitrification inhibitor content is a polymeric/oligomeric compound. In a variation, the reaction product can be dispersed within 20-80% NAPAOL.

In an embodiment, reaction product of cyano-containing nitrification inhibitors with aldehydes comprise a molar ratio of cyano-containing nitrification inhibitors' aldehyde reactive units to aldehyde units of 1:1 to 2:1. In an embodiment using NAPAOL as the reaction medium results in a composition wherein at least 50% or alternatively at least 70% of the total nitrification inhibitor content is a polymeric compound. In a variation, the reaction product can be dispersed within 20-80% NAPAOL.

In an embodiment, reaction product of cyano-containing nitrification inhibitors with aldehydes comprise a molar ratio of cyano-containing nitrification inhibitors' aldehyde reactive units to aldehyde units of 2:1 to 4:1. In an embodiment using NAPAOL as the reaction medium results in a composition of wherein at least 30% or alternatively at least 51% of the total nitrification inhibitors content as polymeric/oligomeric compounds. In a variation, the reaction product can be dispersed within 20-80% NAPAOL.

In an embodiment, a method of making liquid fertilizer additives of biodegradable polymeric and/or oligomeric nitrification inhibitors comprises utilizing the NAPAOL dimethyl sulfoxide (DMSO) as the reaction medium for the reaction of paraformaldehyde with dicyandiamide (DCD) In a variation, a method of making a liquid fertilizer additive of biodegradable polymeric and/or oligomeric nitrification inhibitors comprises reacting a molar ratio of DCD to formaldehyde of 1:1 within (DMSO) resulting in a composition wherein at least 70% or alternatively at least 90% of the total nitrification inhibitor content is a polymeric compound. In a variation, the reaction product can be dispersed within 20-80% DMSO. In another variation, a method of making a liquid fertilizer additive of biodegradable polymeric and/or oligomeric nitrification inhibitors comprises reacting a molar ratio of DCD to formaldehyde of 1:1 to 2:1 within DMSO resulting in a composition of wherein at least 50% or alternatively at least 70% of the total nitrification inhibitor content is a polymeric compound. In a variation, the reaction product can be dispersed within 20-80% DMSO.

In another variation, a method of making a liquid fertilizer additive of biodegradable polymeric and/or oligomeric nitrification inhibitors comprises reacting a molar ratio of DCD to formaldehyde of 2:1 to 4:1 within DMSO resulting in a composition of wherein at least 30% or alternatively at least 50% of the total nitrification inhibitor content is a polymeric compound. In a variation, the reaction product can be dispersed within 20-80% DMSO.

In a variation, the reaction product of DCD reacted with paraformaldehyde comprises a molar ratio of DCD to formaldehyde unit of 4:1 wherein the DMSO is the reaction medium results in a composition of approximately 51.9% of the total nitrification inhibitor content as an oligomeric compound and approximately 48.1% free DCD.

In an embodiment, a method of making fertilizer additives or a liquid composition of biodegradable polymeric and/or oligomeric nitrification inhibitors is comprised of utilizing a NAPAOL as the reaction medium for the reaction of aldehyde(s) with cyano-containing nitrification inhibitors that have one or more aldehyde reactive groups selected from the group consisting of a) primary, b) secondary amines, c) amides, d) thiols, e) hydroxyls and f) phenols comprise DCD reacted with paraformaldehyde at a molar ratio of DCD to formaldehyde unit of up to 4:1 wherein the NAPAOL, dimethyl sulfoxide (DMSO), is the reaction medium resulting in a composition of approximately 51.9% of the total nitrification inhibitor content as an oligomeric compound and approximately 48.1% free DCD wherein the total concentration of polymer bound and free DCD is 10-60% and the DMSO is 40 to 90% of said liquid fertilizer additives.

In a variation, the DCD reacted with paraformaldehyde at a molar ratio of DCD to formaldehyde unit of up to a 4:1 wherein DMSO, is the reaction medium possesses better water solubility versus a DCD/paraformaldehyde reaction product based on a 2:1 molar wherein the compositional ratio is adjusted to 51.9/48.1 of polymer to free DCD at elevated temperatures of 40-90° C. and equivalent compositional amounts of DMSO.

In an embodiment, a method of making fertilizer additives of biodegradable polymeric and/or oligomeric nitrification inhibitors is comprised of utilizing a NAPAOL as the reaction medium for the reaction of aldehyde(s) with cyano-containing nitrification inhibitors that have one or more aldehyde reactive groups selected from the group consisting of a) primary, b) secondary amines, c) amides, d) thiols, e) hydroxyls and f) phenols comprise DCD reacted with paraformaldehyde at a molar ratio of DCD to formaldehyde unit of 1:1 to 2:1 wherein the NAPAOL, dimethyl sulfoxide (DMSO), is the reaction medium resulting in a composition of at least 70% of the total nitrification inhibitor content as a polymeric compound wherein the total concentration of polymer bound and free DCD is 10-80%. In a variation, free DCD can be added to the formulation wherein the composition of free DCD is adjusted to 1-60% of the total of free and polymer bound. When free DCD is present, it increases the initial performance of the product as a nitrification inhibitor.

In an embodiment, a method of making liquid fertilizer additives of biodegradable polymeric and/or oligomeric nitrification inhibitors is comprised of utilizing a NAPAOL as the reaction medium for the reaction of aldehyde(s) with cyano-containing nitrification inhibitors that have one or more aldehyde reactive groups selected from the group consisting of a) primary, b) secondary amines, c) amides, d) thiols, e) hydroxyls and f) phenols may further comprise the addition, during the aldehyde reaction, of polyamines comprising one or more members selected from the group consisting of ethylenediamine, diethylenetriamine, triethylenetetramine tetraethylenepentamine and aminoethylethanolamine whereas the polyamines comprise 0.01-5% of the polymer composition weight in order to modify the coatings' properties such as hydrophobicity, coverage, flexibility of the formed film. In a variation, ammonia is added during the formaldehyde reaction.

In an embodiment, a method of making liquid fertilizer additives of biodegradable polymeric and/or oligomeric nitrification inhibitors is comprised of utilizing a NAPAOL as the reaction medium for the reaction of aldehyde(s) with cyano-containing nitrification inhibitors that have one or more aldehyde reactive groups selected from the group consisting of a) primary, b) secondary amines, c) amides, d) thiols, e) hydroxyls and f) phenols may further comprise the addition, during the aldehyde reaction, of polyols comprising one or more members selected from the group consisting of and/or compounds such as but not limited to one or more polyols selected from the group consisting of 1) trimethylol propane, trimethylol ethane, pentaerythritol, sorbitol and sorbitan, glucose, fructose, galactose, and glycerin, 2) poly ($C_{1-10}$ alkylene) glycols, 3) one or more alkylene glycols from the group consisting of ethylene, 1,3 propylene glycol, 1,2 propylene glycol, and butylene glycol, 4) isopropylidene glycerol 5) one or more alkylene glycol alkyl ethers from the group consisting of tripropylene glycol methyl ether, tripropylene glycol butyl ether, dipropylene glycol butyl ether and tripropylene glycol butyl ether whereas the polyols comprise 0.1-5% of the polymer weight in order to modify the coatings' properties such as hydrophobicity, coverage, flexibility of the formed film.

In an embodiment, the present invention relates to a method of making a liquid fertilizer additive of biodegradable polymeric and/or oligomeric nitrification inhibitors is comprised of utilizing a NAPAOL as the reaction medium for the reaction of aldehyde(s) with cyano-containing nitrification inhibitors that have one or more aldehyde reactive groups selected from the group consisting of a) primary, b) secondary amines, c) amides, d) thiols, e) hydroxyls and f) phenols, wherein the secondary amines may comprise one or more members selected form the group consisting of diethanolamine, diethylamine, cyclohexylamine, methylethanolamine, diisopropanolamine, methylispropylamine. In an embodiment, the secondary amines may comprise 0.1-5% of the polymer weight to assist in controlling the molecular weight build of the biodegradable polymeric and/or oligomeric nitrification inhibitors through chain termination.

In an embodiment, the present invention relates to a method of making liquid fertilizer additives of biodegradable polymeric and/or oligomeric nitrification inhibitors is comprised of utilizing a NAPAOL as the reaction medium for the reaction of aldehyde(s) with cyano-containing nitrification inhibitors that have one or more aldehyde reactive groups selected from the group consisting of a) primary, b) secondary amines, c) amides, d) thiols, e) hydroxyls and f) phenols, wherein the additives may further comprise addition of low molecular weight alcohols (during the formaldehyde reaction) wherein the low molecular weight alcohols comprise one or more members selected from the group consisting of methanol, ethanol, butanol, and hexanol. In an embodiment, the low molecular weight alcohols comprise 0.1-5% of the polymer weight to assist in controlling the molecular weight build of the biodegradable polymeric and/or oligomeric nitrification inhibitors through chain termination.

In an embodiment, the composition of liquid fertilizer additive comprising utilizing a NAPAOL as the reaction medium for the reaction of aldehyde(s) with cyano-containing nitrification inhibitors that have one or more aldehyde reactive groups selected from the group consisting of a) primary, b) secondary amines, c) amides, d) thiols, e) hydroxyls and f) phenols, wherein the composition may further comprise the addition of one or more alkoxy capped monomers selected from the group consisting of 1,3,4,6-tetrakis(methoxymethyl)glycoluril, N,N,N',N',N'',N''-hexakis(methoxymethyl)-1,3,5-triazine-2,4,6-triamine, tetra(methoxymethyl) urea and di(methoxymethyl) urea for coating of fertilizer granules to promote further crosslinking of compounds containing aldehyde reactive groups on the surface of the fertilizer granule and with the surface of urea granules and for adding to molten urea to increase crosslinking of compounds containing aldehyde reactive groups and reaction with the urea. In a variation, the composition can further comprise urea-formaldehyde polymers, ammonia-formaldehyde polymers, urea-ammonia-formaldehyde polymer and triazone-formaldehyde structures.

In a variation, the present invention relates to a composition or liquid fertilizer additives of biodegradable polymeric and/or oligomeric nitrification inhibitors is comprised of utilizing a NAPAOL as the reaction medium for the reaction of aldehyde(s) with cyano-containing nitrification inhibitors that have one or more aldehyde reactive groups selected from the group consisting of a) primary, b) secondary amines, c) amides, d) thiols, e) hydroxyls and f) phenols, wherein the composition may further comprise one or more of members selected from the group consisting of surfactants, buffers, fragrance/odor masking agents, colorants, flow modifiers, silicas, hydrophobized silicas and/or one or more catalysts selected from the group consisting of methane sulfonic acid, sulfuric acid, para-toluene sulfonic acid, phosphoric acid and methane phosphonic acid.

In another variation, the composition may optionally contain one or more biologically active agents and/or biologics selected from the group consisting of a) urease inhibitors, nitrification inhibitors, pesticides, herbicides fungicides(s), and insecticide(s).

In an embodiment, the post reaction composition of liquid fertilizer additive comprising biodegradable polymeric and/or oligomeric nitrification inhibitors using a NAPAOL as the reaction medium for the reaction of aldehyde(s) with cyano-containing nitrification inhibitors that have one or more aldehyde reactive groups wherein the reactive groups are selected from the group consisting of a) primary, b) secondary amines, c) amides, d) thiols, e) hydroxyls and f) phenols may further comprise one or more non-aqueous organo liquids selected from the group consisting of polar aprotic, aprotic and protic organo solvents wherein these groups are as follows:
  a) one or more aprotic solvents selected from the group consisting of 1) one or more polyols capped with acetate or formate wherein the polyol portion selected from the group consisting of ethylene glycol, 1,3 propylene glycol, 1,2 propylene glycol, butylene glycol, trimethylol propane, trimethylol ethane, pentaerythritol, sorbitol and sorbitan, glucose, fructose, galactose and glycerin, 2) one or more alkylene glycol alkyl ethers acetates selected from the group consisting of dipropylene glycol methyl ether acetate, tripropylene glycol methyl ether acetate, and tripropylene glycol butyl ether acetate and, 3) isophorone, 4) one or more diesters selected from the group consisting of dimethylsuccinate, dimethyl adipate, diethyl glutarate, and dimethyl glutarate, 5) dimethylacetamide, 6) dimethylformamide, 7) dimethyl-2-imidazolidinone, 8) 1-Methyl-2-pyrrolidone and 9) limonene,
  b) one or more protic solvents selected from the group consisting of: 1) an alcohol from the family of $C_{1-10}$ alkanols, 2) one or more polyols selected from the group consisting of trimethylol propane, trimethylol ethane, pentaerythritol, sorbitol, sorbitan, glucose, fructose, galactose, and glycerin, 3) one or more poly ($C_{1-10}$ alkylene) glycols represented by the structure:

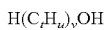
H(C$_t$H$_u$)$_v$OH t is an integer: 1-10
  u is an integer: 2-20
  and v is an integer: 1-20,
  4) one or more alkylene glycols selected from the group consisting of ethylene glycol, 1,3 propylene glycol, 1,2 propylene glycol, and butylene glycol, 5) isopropylidene glycerol 6) one or more alkylene glycol alkyl ethers selected from the group represented by the structure:

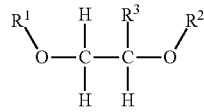

wherein $R^1$ is: $CH_3$, $C_2H_5$, $C_3H_7$ or $C_4H_9$
  wherein $R^2$ is: H or the structure

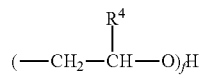

wherein $R^3$ is: H or $CH_3$
  wherein $R^4$ is H and $CH_3$
  and f is an integer between 1 and 15,
  7) one or more alkyl lactates selected from the group consisting of ethyl, propyl and butyl lactate, 8) one or more alkanolamines selected from the group represented by the structure:

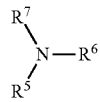

wherein $R^5$ is: $C_2H_4OR^8$ or $C_3H_6OH$
  wherein $R^6$ is: H, $C_2H_4OR^8$ or $C_3H_6OH$
  wherein $R^7$ is: H, $C_2H_4OR^8$ or $C_3H_6OH$
  wherein $R^8$ is: $(C_2H_4O)_gH$
  and g is an integer between 1-10,
and 9) glycerol carbonate,
c) and one or more polar aprotic solvents selected from the group consisting of
  1) dimethyl sulfoxide
  2) and dialkyl, diaryl, or alkylaryl sulfoxide(s) having the formula:

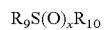
R$_9$S(O)$_x$R$_{10}$ wherein $R_9$ and $R_{10}$ are each independently a $C_{1-6}$ alkylene group, an aryl group, or $C_{1-3}$alkylenearyl group or $R_9$ and $R_{10}$ together with the sulfur to which they are attached form a 4 to 8 membered ring
    wherein $R_9$ and $R_{10}$ together are a $C_{1-6}$ alkylene group which optionally contains one or more atoms selected from the group consisting of O, S, Se, Te, N, and P in the ring and x is 1 or 2, and optionally further comprising:
  3) one or more alkylene carbonates selected from the group consisting of ethylene carbonate, propylene carbonate and butylene carbonate 4) 1-Methyl-2-pyrrolidone, 5) one or more organo phosphorous liquids selected from the group consisting of hexamethylphosphoramide and one or more trialkylphosphates selected from the group represented by the formula.

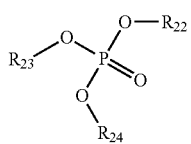

wherein:
$R_{22}$ is alkyl radical —$C_1H_3$ to —$C_6H_{13}$
$R_{23}$ is alkyl radical —$C_1H_3$ to —$C_6H_{13}$
$R_{24}$ is alkyl radical —$C_1H_3$ to —$C_6H_{13}$
6) 1,2-dimethyloxyethane, 7) 2-methoxyethyl ether and 8) cyclohexylpyrrolidone.

In an embodiment, said non-aqueous organo liquid solvents can be added to improve the properties of said liquid fertilizer additives, wherein the properties that can be improved include but are not limited to evenness of the coating, viscosity, solubility in aqueous fertilizer such as UAN, dispersibility in anhydrous ammonia and dispersibility in urea and modified ureas such as urea formaldehyde polymer (UFP), shelf life stability and cold weather flowability In another variation, said non-aqueous organo liquid solvents can be added to impact the properties of the treated nitrogen source such as but not limited to water resistance, clumping of solid nitrogen sources and homogeneity of the dispersion within liquid/molten nitrogen sources.

In a variation, said liquid fertilizer additives may further comprise one or more of members selected from the group consisting of surfactants, buffers, fragrance/odor masking agents, colorants, flow modifiers, silicas, hydrophobized silicas.

In a variation, said liquid fertilizer additives may further comprise one or more biologically active agents and biologics selected from the group consisting of a) urease inhibitors, nitrification inhibitors, pesticides, herbicides fungicides(s), and insecticide(s).

In an embodiment, the present invention relates to a method of making liquid fertilizer additives of biodegradable polymeric and/or oligomeric nitrification inhibitors, wherein the method is comprised of utilizing a NAPAOL as the reaction medium for the reaction of aldehyde(s) with cyano-containing nitrification inhibitors that have one or more aldehyde reactive groups selected from the group consisting of a) primary, b) secondary amines, c) amides, d) thiols, e) hydroxyls and f) phenols. In an embodiment, the composition may further comprise one or more non-cyano-nitrification inhibitors selected from the group consisting of:

a) one or more pyrazoles represented by the structure

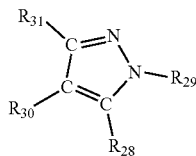

Whereas $R_{28}$=—H, —$CH_3$, —$CH_2CH_3$, —$NH_2$ or —$NHCH_3$
Whereas $R_{29}$=—H, —OH, —SH, —$CONH_2$ or —$CONHCH_3$
Whereas $R_{30}$=—H, —$CH_3$, —$CH_2CH_3$, —$NH_2$ or —$NHCH_3$
Whereas $R_{31}$=—H, —$CH_3$, —$CH_2CH_3$, —$NH_2$ or —$NHCH_3$ b) one or more members selected from the group consisting of 2-amino-4-chloro-6-methyl-pyrimidine, 1,3-benzothiazole-2-thiol, 4-amino-N-1,3-thiazol-2-ylbenzenesulfonamide, thiourea, 2,4-diamino-6-trichloromethyl-5-triazine, 4-amino-1,2,4-triazole, 3-mercapto-1,2,4-triazole, 2,3, dihydro-2,2-dimethyl-7-benzofuranol methyl-carbamate, In an embodiment, a liquid fertilizer additive of biodegradable polymeric and/or oligomeric nitrification inhibitors comprises utilizing a NAPAOL as the reaction medium for the reaction of aldehyde(s) with non-cyano-containing nitrification inhibitors that have one or more aldehyde reactive groups selected from the group consisting of a) primary, b) secondary amines, c) amides, d) thiols, e) hydroxyls and f) phenols. In an embodiment, a liquid fertilizer additive of biodegradable polymeric and/or oligomeric nitrification inhibitors comprises said non-cyano-nitrification inhibitors reacting with paraformaldehyde at a molar ratio of non-cyano-nitrification inhibitors to formaldehyde compounds of 2:1 to 2.5:1 with NAPAOL as the reaction medium. In a variation, the composition results in a composition that comprises at least 50% or alternatively at least 70% of methylene bis non-cyano-nitrification inhibitor oligomers. In another variation, methylene bis non-cyano-nitrification inhibitor oligomers are believed to show improvements on performance issues such as lowering atmospheric volatility and decreasing migration through the soil due to low molecular weight and/or water solubility. In a variation, the resulting product may also possess nitrification inhibition properties. In a variation, the resulting product may also deliver nitrification inhibition properties due to the biodegradation of the polymer.

In an embodiment, a liquid fertilizer additive of biodegradable polymeric and/or oligomeric nitrification inhibitors is comprised of utilizing a NAPAOL as the reaction medium for the reaction of aldehyde(s) with non-cyano-containing nitrification inhibitors that have one or more aldehyde reactive groups selected from the group consisting of a) primary, b) secondary amines, c) amides, d) thiols, e) hydroxyls and f) phenols comprise dimethyl pyrazole (DMP) reacting with paraformaldehyde at a molar ratio of DMP to formaldehyde unit of 2:1. In a variation, the NAPAOL comprises one or more members selected from the group consisting of sulfolane and dimethyl sulfoxide as the reaction medium. In another variation, the composition comprises at least 70% of a methylene bis DMP oligomer. In another variation, the resulting liquid fertilizer additive possesses lower atmospheric volatility relative to unreacted DMP. In a variation, the NAPAOL is sulfolane.

In an embodiment, a liquid fertilizer additive of biodegradable polymeric and/or oligomeric nitrification inhibitors is comprised of utilizing a NAPAOL as the reaction medium for the reaction of aldehyde(s) with non-cyano-containing nitrification inhibitors that have one or more aldehyde reactive groups selected from the group consisting of a) primary, b) secondary amines, c) amides, d) thiols, e) hydroxyls and f) phenols. In a variation, the method may comprise 1) dissolving the non-cyano-nitrification inhibitor in NAPAOL at temperatures in the range of 30-110° C. and cooling to 40-60° C. and ensuring that pH is in the range of 8-10, 2) slowly adding the aldehyde and allowing the exotherm to be controlled either through charge rate or removing the heat of reaction through a cooling median, 3) slowly heating the composition to 70-90° C. and waiting for a period of time, (e.g., 1-10 hours) 4) cooling the composition to 40-70° C. and slowly charging enough of acid catalyst such as but not limited to one or more members selected from the group consisting of methane sulfonic acid, sulfuric acid, para-toluene sulfonic acid phosphoric acid and methane phosphonic acid to drop the pH to 5-8 and let mix for an extended period of time to control the exotherm, 5) slowly heating the composition to 90-115° C.

In a variation, after holding the reaction product enumerated above for a period of time, one can elect to place the batch under a vacuum of 0.1-100 mm to assist in removing water by-products, driving the reaction to more completion and removing any unreacted aldehyde until residual aldehyde content is <700 ppm and then cooling the batch. In a variation, one can remove oxygen from the reactor before the addition of the formaldehyde. In another variation, one can apply a vacuum to the vessel after the addition of the acid catalyst to assist in driving the reaction to completion in a shorter period of time. In another variation, one can alternate between a hard sparge and vacuum to remove excess aldehyde.

In an embodiment, a liquid fertilizer additive of biodegradable polymeric and/or oligomeric nitrification inhibitors is comprised of utilizing a NAPAOL as the reaction medium for the reaction of aldehyde(s) with cyano-containing nitrification inhibitors and/or non-cyano-containing nitrification inhibitors that have one or more aldehyde reactive groups selected from the group consisting of a) primary, b) secondary amines, c) amides, d) thiols, e) hydroxyls and f) phenols wherein the NAPAOL comprises one or more members selected from the group consisting of:
a) dimethyl sulfoxide,
b) and dialkyl, diaryl, or alkylaryl sulfoxide(s) having the formula:

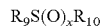

wherein $R_9$ and $R_{10}$ are each independently a $C_{1-6}$ alkylene group, an aryl group, or $C_{1-3}$alkylenearyl group or $R_9$ and $R_{10}$ together with the sulfur to which they are attached form a 4 to 8 membered ring wherein $R_9$ and $R_{10}$ together are a $C_{1-6}$ alkylene group which optionally contains one or more atoms selected from the group consisting of O, S, Se, Te, N, and P in the ring and x is 1 or 2,
c) and one or more alkylene carbonates selected from the group consisting of ethylene carbonate, propylene carbonate and butylene carbonate d) 1-Methyl-2-pyrrolidone, e) one or more organo phosphorous liquids selected from the group consisting of hexamethylphosphoramide and one or more trialkylphosphates selected from the group represented by the formula:

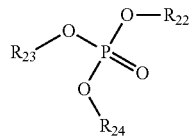

wherein:
$R_{22}$ is alkyl radical —$C_1H_3$ to —$C_6H_{13}$
$R_{23}$ is alkyl radical —$C_1H_3$ to —$C_6H_{13}$
$R_{24}$ is alkyl radical —$C_1H_3$ to —$C_6H_{13}$
f) 1,2-dimethyloxyethane, g) 2-methoxyethyl ether and h) cyclohexylpyrrolidone,
wherein said nitrification inhibitors that contain one or more aldehyde reactive groups are selected from the group consisting of:

a) one or more cyano-containing nitrification inhibitors selected from the group represented by the structures:

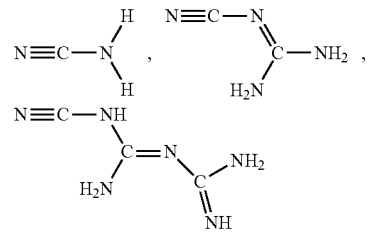

b) one or more non-cyano-containing nitrification inhibitors selected from the group consisting of:
1) one or more pyrazoles represented by the structure

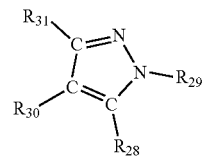

wherein $R_{28}$=—H, —$CH_3$, —$CH_2CH_3$, —$NH_2$ or —$NHCH_3$
wherein $R_{29}$=—H, —OH, —SH, —$CONH_2$ or —$CONHCH_3$
wherein $R_{30}$=—H, —$CH_3$, —$CH_2CH_3$, —$NH_2$ or —$NHCH_3$
wherein $R_{31}$=—H, —$CH_3$, —$CH_2CH_3$, —$NH_2$ or —$NHCH_3$
2) one or more members selected from the group consisting of 2-amino-4-chloro-6-methyl-pyrimidine, 1,3-benzothiazole-2-thiol, 4-amino-N-1,3-thiazol-2-ylbenzenesulfonamide, thiourea, 2,4-diamino-6-trichloromethyl-5-triazine, 4-amino-1,2,4-triazole, 3-mercapto-1,2,4-triazole, 2,3, dihydro-2,2-dimethyl-7-benzofuranol methyl-carbamate,
wherein the nitrification inhibitors are reacted with said aldehydes utilizing the NAPAOL as the reaction medium wherein the one or more aldehydes are selected from the group consisting of:
methanal, ethanal, propanal, butanal, pentanal, hexanal, methylethanal, methylpropanal, methylbutanal, phenylacetaldehyde, benzaldehyde, 2-propenal, 3-oxopropanoic, 2-methyl-3-oxopropanoic acid, 4-oxobutanoic acid, oxoacetic acid, 5-oxopentanoic acid, 6-oxohexanoic acid, 2-oxopropanal, cyclohexanal, furfural, methyl esters of 3-oxopropanoic, 2-methyl-3-oxopropanoic acid, 4-oxobutanoic acid, oxoacetic acid, 5-oxopentanoic acid and 6-oxohexanoic acid, ethandial, 1,3-propanedial, butanedial, pentanedial, phthalaldehyde and methanethial.

In a variation, a liquid fertilizer additive of biodegradable polymeric and/or oligomeric nitrification inhibitors is part of a method comprised of utilizing NAPAOL as the reaction medium for the reaction of aldehyde(s) with nitrification inhibitors may further comprise acid catalyst such as but not limited to one or more members selected from the group consisting of methane sulfonic acid, sulfuric acid, para-toluene sulfonic acid, phosphoric acid and methane phosphonic acid.

In another variation, a liquid fertilizer additive of biodegradable polymeric and/or oligomeric nitrification inhibitors is comprised of utilizing said NAPAOL as the reaction medium for the reaction of said aldehyde(s) with said nitrification may further comprise an agent to neutralize the acid catalyst after the reaction is completed such as but not limited to one or more members selected from the group consisting of NaOH, NaOCH$_3$, Na$_2$CO$_3$, KOH, K$_2$CO$_3$, NH$_3$ and one or more alkanolamines selected from the group represented by the structure:

wherein R$^5$ is: C$_2$H$_4$OR$^8$ or C$_3$H$_6$OH
wherein R$^6$ is: H, C$_2$H$_4$OR$^8$ or C$_3$H$_6$OH
wherein R$^7$ is: H, C$_2$H$_4$OR$^8$ or C$_3$H$_6$OH
wherein R$^8$ is: (C$_2$H$_4$O)$_g$H
and g is an integer between 1-10.

In another variation, the post reaction composition of liquid fertilizer additive comprising said biodegradable polymeric and/or oligomeric nitrification inhibitors is comprised of utilizing a NAPAOL as the reaction medium for the reaction of aldehyde(s) with cyano-containing nitrification inhibitors and/or non-cyano-containing nitrification inhibitors that have one or more aldehyde reactive groups selected from the group consisting of a) primary, b) secondary amines, c) amides, d) thiols, e) hydroxyls and f) phenols. In a variation, the post reaction composition may further comprise polar aprotic, aprotic and protic organo solvent wherein the composition of the non-aqueous liquid organo solvents may further comprise:
 a) one or more aprotic solvents selected from the group consisting of 1) one or more polyols capped with acetate or formate wherein the polyol portion selected from the group consisting of ethylene glycol, 1,3 propylene glycol, 1,2 propylene glycol, butylene glycol, trimethylol propane, trimethylol ethane, pentaerythritol, sorbitol and sorbitan, glucose, fructose, galactose and glycerin, 2) one or more alkylene glycol alkyl ethers acetates selected from the group consisting of dipropylene glycol methyl ether acetate, tripropylene glycol methyl ether acetate, and tripropylene glycol butyl ether acetate and, 3) isophorone, 4) one or more diesters selected from the group consisting of dimethylsuccinate, dimethyl adipate, diethyl glutarate, and dimethyl glutarate, 5) dimethylacetamide, 6) dimethylformamide, 7) dimethyl-2-imidazolidinone, 8) 1-Methyl-2-pyrrolidone and 9) limonene,
 b) one or more protic solvents selected from the group consisting of: 1) an alcohol from the family of C$_{1-10}$ alkanols, 2) one or more polyols selected from the group consisting of trimethylol propane, trimethylol ethane, pentaerythritol, sorbitol, sorbitan, glucose, fructose, galactose, and glycerin, 3) one or more poly (C$_{1-10}$ alkylene) glycols represented by the structure:

H(C$_t$H$_u$)$_v$OH t is an integer: 1-10
 u is an integer: 2-20
 and
 v is an integer: 1-20,
 4) one or more alkylene glycols selected from the group consisting of ethylene glycol, 1,3 propylene glycol, 1,2 propylene glycol, and butylene glycol, 5) isopropylidene glycerol 6) one or more alkylene glycol alkyl ethers selected from the group represented by the structure:

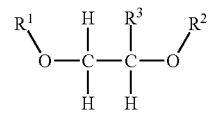

wherein R$^1$ is: CH$_3$, C$_2$H$_5$, C$_3$H$_7$ or C$_4$H$_9$
wherein R$^2$ is: H or the structure

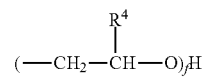

wherein R$^3$ is: H or CH$_3$
wherein R$^4$ is H and CH$_3$
and f is an integer between 1 and 15
 7) one or more alkyl lactates selected from the group consisting of ethyl, propyl and butyl lactate, 8) one or more alkanolamines selected from the group represented by the structure:

where R$^5$ is: C$_2$H$_4$OR$^8$ or C$_3$H$_6$OH
where R$^6$ is: H, C$_2$H$_4$OR$^8$ or C$_3$H$_6$OH
where R$^7$ is: H, C$_2$H$_4$OR$^8$ or C$_3$H$_6$OH
where R$^8$ is: (C$_2$H$_4$O)$_g$H
and g is an integer between 1-10
and 9) glycerol carbonate,
 c) and one or more polar aprotic solvents selected from the group consisting of
  1) dimethyl sulfoxide
  2) and dialkyl, diaryl, or alkylaryl sulfoxide(s) having the formula:

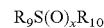

R$_9$S(O)$_x$R$_{10}$ wherein R$_9$ and R$_{10}$ are each independently a C$_{1-6}$ alkylene group, an aryl group, or C$_{1-3}$alkylenearyl group or R$_9$ and R$_{10}$ together with the sulfur to which they are attached form a 4 to 8 membered ring wherein R$_9$ and R$_{10}$ together are a C$_{1-6}$ alkylene group which optionally contains one or more atoms selected from the group consisting of O, S, Se, Te, N, and P in the ring and x is 1 or 2, and optionally further comprising
  3) one or more alkylene carbonates selected from the group consisting of ethylene carbonate, propylene carbonate and butylene carbonate 4) 1-Methyl-2-pyrrolidone, 5) one or more organo phosphorous liquids selected from the group consisting of hexamethylphosphoramide and one or more trialkylphosphates selected from the group represented by the formula.

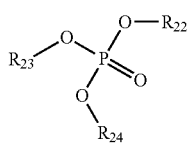

wherein:
$R_{22}$ is alkyl radical —$C_1H_3$ to —$C_6H_{13}$
$R_{23}$ is alkyl radical —$C_1H_3$ to —$C_6H_{13}$
$R_{24}$ is alkyl radical —$C_1H_3$ to —$C_6H_{13}$
6) 1,2-dimethyloxyethane, 7) 2-methoxyethyl ether and 8) cyclohexylpyrrolidone In an embodiment, said non-aqueous organo liquid solvents can be added to improve the properties of said liquid fertilizer additives such as but not limited to hydrophobicity, viscosity and cold weather flowability and/or the properties of the treated nitrogen source such as but not limited to water resistance, clumping of solid nitrogen sources and solubility in liquid/molten nitrogen sources.

In another variation, the composition may further comprise one or more members selected from the group consisting of:
a food coloring or dye that may be used to improve the visual evidence of complete coverage and serve as a visual marker,
scents or masking agents to improve the odor of the formulations,
nonionic, anionic, cationic, zwitterionic, and/or amphoteric surfactants to improve formula application performance of fertilizer granules;
buffering agents
flow modifiers, silicas and hydrophobized silicas and
catalyst(s) to improve reaction completion.

In another variation, the composition may further comprise one or more members selected from the group consisting of: a) one or more biologically active agents and b) biologics wherein the biologically active agents and biologics may possess one or more properties selected from the group consisting of a) urease inhibitors, nitrification inhibitors, pesticides, herbicides fungicides(s) and insecticide(s)

In an embodiment, a liquid fertilizer additive of biodegradable polymeric and/or oligomeric nitrification inhibitors is comprised of utilizing a NAPAOL as the reaction medium for the reaction of aldehyde(s) with cyano- and/or non-cyano-containing nitrification inhibitors that have one or more aldehyde reactive groups selected from the group consisting of a) primary, b) secondary amines, c) amides, d) thiols, e) hydroxyls and f) phenols may further comprise one or more members selected from the group consisting of: a) one of more biologically active agents and b) one or more biologics wherein the biologically active agents and biologics may possess one or more properties selected from the group consisting of urease inhibitors, nitrification inhibitor(s), pesticide(s), herbicide(s), fungicides(s), and insecticide(s). In a variation, the use of a liquid fertilizer additive of biodegradable polymeric and/or oligomeric nitrification inhibitors will result in lower dissolution of these biologically active agents that are encapsulated within the hydrophobic film thereby improving performance by increasing the length of time these biologically active agents and biologics are available.

In an embodiment, a liquid fertilizer additive of biodegradable polymeric and/or oligomeric nitrification inhibitors is comprised of utilizing a NAPAOL as the reaction medium for the reaction of aldehyde(s) with cyano-containing nitrification inhibitors and/or non-cyano-containing nitrification inhibitors that have one or more aldehyde reactive groups selected from the group consisting of a) primary, b) secondary amines, c) amides, d) thiols, e) hydroxyls and f) phenols may further comprise one or more urease inhibitors selected from the group consisting of aliphatic phosphoric triamide, phosphoramides and N-alkyl thiophosphoric triamides, (aminomethyl)phosphinic acids and their salts and aminomethyl (alkylaminomethyl)phosphinic acids and their salts. In a variation the urease inhibitor is N-(n-butyl) thiophosphoric triamide.

In an embodiment, a liquid fertilizer additive of biodegradable polymeric and/or oligomeric nitrification inhibitors is comprised of utilizing a NAPAOL as the reaction medium for the reaction of aldehyde(s) with cyano-containing nitrification inhibitors and/or non-cyano-containing nitrification inhibitors that have one or more aldehyde reactive groups selected from the group consisting of a) primary, b) secondary amines, c) amides, d) thiols, e) hydroxyls and f) phenols may further comprise one or more nitrification inhibitors selected from the group consisting of 2-chloro-6-trichloromethyl)pyridine, 4-amino-1,2,4-6-triazole-HCl, 2,4-diamino-6-trichloromethyltriazine CL-1580, dicyandiamide (DCD), thiourea, 1-mercapto-1,2,4-triazole, ammonium thiosulfate, dimethylpyrazole organic and inorganic salts and 2-amino-4-chloro-6-methylpyrimidine In a variation the nitrification inhibitor comprises dicyandiamide.

In an embodiment a liquid fertilizer additive of biodegradable polymeric and/or oligomeric nitrification inhibitors is comprised of utilizing a NAPAOL as the reaction medium for the reaction of aldehyde(s) with cyano-containing nitrification inhibitors and/or non-cyano-containing nitrification inhibitors that have one or more aldehyde reactive groups selected from the group consisting of a) primary, b) secondary amines, c) amides, d) thiols, e) hydroxyls and f) phenols may further comprise one or more nitrification inhibitors selected from the group consisting of 2-chloro-6-trichloromethyl)pyridine, 4-amino-1,2,4-6-triazole-HCl, 2,4-diamino-6-trichloromethyltriazine CL-1580, dicyandiamide (DCD), thiourea, 1-mercapto-1,2,4-triazole, ammonium thiosulfate, dimethylpyrazole organic and inorganic salts and 2-amino-4-chloro-6-methylpyrimidine and one or more urease inhibitors selected from the group consisting of aliphatic phosphoric triamide, phosphoramides and N-alkyl thiophosphoric triamides, (aminomethyl)phosphinic acids and their salts and aminomethyl (alkylaminomethyl) phosphinic acids and their salts.

In an embodiment a liquid fertilizer additive of biodegradable polymeric and/or oligomeric nitrification inhibitors is comprised of utilizing a NAPAOL as the reaction medium for the reaction of aldehyde(s) with cyano-containing nitrification inhibitors and/or non-cyano-containing nitrification inhibitors that have one or more aldehyde reactive groups selected from the group consisting of a) primary, b) secondary amines, c) amides, d) thiols, e) hydroxyls and f) phenols may further comprise one or more biologics selected from the group consisting of
a) one or more *Bacillus* biologics selected from the group consisting of
1) *Bacillus mucilaginosas*
2) *Bacillus subtilus*
3) *Lactobacillus acidophilus*
4) *Bacillus amylofliquifaciens*
5) *Bacillus itcheniformis*
6) *Bacillus megaterium*
7) *Bacillus pumilus*
8) *Bacillus megaterium*

9) *Bacillus pumilus*
10) *Bacillus circulans*
11) *Bacillus globisporus*
12) *Bacillus firmus*
13) *Bacillus thuringiensis galleriae*
14) *Bacillus thuringiensis kurstaki*
15) *Bacillus cereus*
16) *Bacillus globisporus*
17) *Bacillus amyloliquefaciens*
18) *Bacillus thuringiensis galleriae*
19) *Bacillus thuringiensis kurstaki*
20) *Bacillus mycoide isolate*
21) *Bacillus aryabhattai*
22) *B. flexus*
23) *B. nealsonii*
24) *Bacillus sphaericus*
25) *B. vallismortis*
b) *Rhizobium*
c) *Bradyrhiwbium* species
d) *Bradyrhiwbium japonicum*
e) *Rhizobium meliloti*
f) One or more *Azospirillum* biologics selected from the group consisting of
  1) *Azospirillum lipoferum*
  2) *Azospirillum brasilense*
  3) *Azospirillum amazonense*
  4) *Azospirillum halopreaferens*
  5) *Azospirillum irankense*
g) One or more *Azobacter* and *Gluconacetobacter* biologics selected from the group consisting of
  1) *Azotobacter agilis*
  2) *Azotobacter armeniacus*
  3) *Azotobacter* sp. AR
  4) *Azotobacter beijerinckii*
  5) *Azotobacter chroococcum*
  6) *Azotobacter* sp. DCU26
  7) *Azotobacter* sp. FA8
  8) *Azotobacter nigricans*
  9) *Azotobacter paspali*
  10) *Azotobacter salinestris*
  11) *Azotobacter tropicalis*
  12) *Azotobacter vinelandii*
h) *Phosphobacteria*
i) *Cyanobacteria*
j) *Herbaspirillum*
k) *Burkholderia*,
l) *Pseudomonas*
m) *Gluconacetobacter*
n) *Enterobacter*
o) *Klebsiella*
p) *Burkholderia*
q) *Laccaria bicolor*
r) *Glomus imraradices timanita*
s) *Actinomyces*
t) *Penicillium*
u) *Mesorhizobiwn cicero*
v) *Reynoutria sachalinensis*
w) One or more insecticidal or insect repellent microbial species and strains selected from the group consisting of: *Telenomus podisi, Baculovirus anticarsia, Trichogramma pretiosum, Trichogramma gallai, Chromobacterium subtsugae, Trichoderma fertile, Beauveria bassiana, Beauveria bassiana, Beauveria bassiana, Paecilomyces jknwsoroseu, Trichoderma harzianum, Verticillium lecanii, lsarfofumosarosea Lecanicillium muscarium, Streptomyces microflavus, Muscodor albus,*
x) one or more nematodal microbial species and strains selected from the group consisting of: *Myrothecium verrucaria, Pasteuria species, Pasteuria Metarhizium species, Flavobacteriwn* species and
y) one or more antifungal, antimicrobial and/or plant growth promoting microbial species and strains selected from a group consisting of: *Gliocladium* species, *Pseudomonas* species (e.g. *Pseudomonas fluorescens, Pseudomonas fluorescens. putida* and *P. chlororaphis*), *Pseudomonasfluorescens* VP5, *Pseudomonas diazotrophicus, Enterobacter cloacae, Trichodema* species, *Trichoderma virens, Trichoderma atroviride* strains, *Coniothyrium minitans, Gliocladium* species, *Gliacladium virens, Gliacladium roseum, Trichodemw harzianum* species.

In an embodiment, these new liquid fertilizer additives can be added to a nitrogen source through methods comprising one or more application techniques selected from the group consisting of:

a. coating a nitrogen source particle with said liquid fertilizer additives utilizing spraying, metering or slowly pouring onto a nitrogen source that is in a temperature range of −20° C. to 100° C. In a variation the mixing of the materials may be accomplished in a simple mixing tank mixing materials prior to use, using a metering system to inject materials simultaneously, or mixing via a spray injection system. In another variation, the mixture can be mixed in any common mixing tank, blenders and tumblers or on a conveyer belt. In another variation, the metering of all ingredients can be based on a weight, it may also be on a volumetric basis, b. generating during the process a nitrogen source particle, granule and/or prill in which the liquid formulation can be added directly into the molten nitrogen source before formation of a particle, granule or a prill and/or sprayed into the prilling tower when molten nitrogen source is released from the top of prilling tower and the falling liquid nitrogen source is crystallized by air in the tower, c. dissolving liquid fertilizer additive into aqueous liquid fertilizers and d. incorporating said liquid fertilizer additives into non-aqueous liquid nitrogen sources such as pressurized anhydrous ammonia gas.

In a variation, these compositions can be sprayed directly on the soil and/or on natural fertilizers such as manure or compost.

In an embodiment, the usage rates of these new liquid formulations with a nitrogen source is dependent on the application technique, the weight or volume of the nitrogen source applied per acre of soil to be treated, the nitrification inhibitor type, the concentration of polymer bound and free nitrification inhibitors present in the liquid formulation's composition. In a variation, if the application technique is the addition of said liquid fertilizer additives to a liquid/molten nitrogen source, the usage rate will be dependent on the solubility and impact of the desired granule/prill properties.

In a variation, higher levels of total nitrification inhibitors, which are defined as polymer bound and free, can be applied to the soil directly or as a liquid fertilizer additive to natural and manmade nitrogen sources. Moreover, due to the slow release of nitrification inhibitors through the biodegradation of the polymer backbone and the maintenance of an effective level of free nitrification inhibitors, the nitrogen source is made more effective in providing nutrients for plant growth over an extended period of time. In a variation, a liquid fertilizer additive of biodegradable polymeric and/or oligomeric nitrification inhibitors is comprised of utilizing a NAPAOL as the reaction medium for the reaction of aldehyde(s) with cyano-containing nitrification inhibitors and/or non-cyano-containing nitrification inhibitors that have one or more aldehyde reactive groups selected from the group consisting of a) primary, b) secondary amines, c) amides, d) thiols, e) hydroxyls and f) phenols may have low percentages of 20-30% of a NAPAOL resulting in lower negative impact of a nitrogen source particles' physical properties such as but not limited to a low hardness index. In a variation, a low hardness index of a particle negatively impacts storage, packaging, blending and distribution. In another variation, low percent composition of NAPAOL in a liquid fertilizer additive may be achieved by running the first reaction process at lower temperatures of 60-80° C. for a longer period of time (e.g. 4-12 hours).

In another variation, low percent composition of NAPAOL in a liquid fertilizer additive may be achieved by running the second reaction process at a lower vacuum (e.g. 0.01-1 mm), increasing the temperature after the second reaction has been completed and any acid catalyst has been neutralized (e.g. 90-120° C.) stripping out NAPAOL to desired levels.

In another variation, a liquid fertilizer additive of biodegradable polymeric and/or oligomeric nitrification inhibitors is comprised of utilizing a NAPAOL as the reaction medium for the reaction of aldehyde(s) with cyano-containing nitrification inhibitors and/or non-cyano-containing nitrification inhibitors that have one or more aldehyde reactive groups selected from the group consisting of a) primary, b) secondary amines, c) amides, d) thiols, e) hydroxyls and f) phenols may be added to molten nitrogen sources at elevated temperatures (e.g. 80-140° C.) to lower said liquid fertilizer additive's viscosity and aide in ensuring a homogeneous distribution within the molten nitrogen source.

In an embodiment, the composition of a fertilizer comprises liquid fertilizer additives of biodegradable polymeric and/or oligomeric nitrification inhibitors that are comprised of utilizing a NAPAOL as the reaction medium for the reaction of aldehyde(s) with cyano-containing nitrification inhibitors and/or non-cyano-containing nitrification inhibitors that have one or more aldehyde reactive groups selected from the group consisting of a) primary, b) secondary amines, c) amides, d) thiols, e) hydroxyls and f) phenols and one or more nitrogen sources selected from a group consisting of urea, urea formaldehyde polymer, treated urea. In an embodiment, the treated urea is defined as a composition comprising a urea and biologically active agents and/or biologics added either through a coating application or added to the urea during the urea production process either in the melt portion or deposited to the urea during the formation of the urea granule when the urea is still hot. In a variation, a liquid fertilizer additives of biodegradable polymeric and/or oligomeric nitrification inhibitors comprise 0.05-10% of the fertilizer composition. In another variation, the NAPAOL comprises 0.01-9.5% of the fertilizer composition.

In an embodiment, one can coat a granule of treated nitrogen source with a liquid fertilizer additive of biodegradable polymeric and/or oligomeric nitrification inhibitors that is comprised of utilizing a NAPAOL as the reaction medium for the reaction of aldehyde(s) with cyano-containing nitrification inhibitors and/or non-cyano-containing nitrification inhibitors that have one or more aldehyde reactive groups selected from the group consisting of a) primary, b) secondary amines, c) amides, d) thiols, e) hydroxyls and f) phenols. A treated nitrogen source is defined as a composition comprising a nitrogen source and biologically active agents and/or biologics added either through a coating application or added to the nitrogen source during the nitrogen source's production process either in the melt portion or applied to the nitrogen source during the formation of the nitrogen source's granule.

In a variation, the nitrogen sources and/or the treated nitrogen sources can be mixed with other fertilizer components and then the liquid fertilizer additives of biodegradable polymeric and/or oligomeric nitrification inhibitors comprised of utilizing a NAPAOL as the reaction medium for the reaction of aldehyde(s) with cyano-containing nitrification inhibitors and/or non-cyano-containing nitrification inhibitors that have one or more aldehyde reactive groups selected from the group consisting of a) primary, b) secondary amines, c) amides, d) thiols, e) hydroxyls and f) phenols can be applied. This will impart slower dissolution of these fertilizer components and nitrogen and/or treated nitrogen sources into water because they have been encapsulated within the hydrophobic film. In an embodiment said liquid fertilizer additives will provide free and polymer bound nitrification inhibition, thereby improving performance in providing nutrients for plant growth over an extended period of time.

In one embodiment, a fertilizer comprises a) a liquid fertilizer additive of biodegradable polymeric and/or oligomeric nitrification inhibitors that is comprised of utilizing a NAPAOL as the reaction medium for the reaction of aldehyde(s) with cyano-containing nitrification inhibitors and/or non-cyano-containing nitrification inhibitors that have one or more aldehyde reactive groups selected from the group consisting of 1) primary and secondary amines, 2) amides, 3) thiols, 4) hydroxyls and 5) phenols and urea. In a variation, said liquid fertilizer additives deliver a more hydrophobic coating of free and polymer bound nitrification inhibitors making the urea more effective in providing nutrients for plant growth over an extended period of time.

In an embodiment, the composition of a fertilizer comprises urea and a liquid fertilizer additives of biodegradable polymeric and/or oligomeric nitrification inhibitors that is comprised of utilizing a NAPAOL as the reaction medium for the reaction of aldehyde(s) with cyano-containing nitrification inhibitors and/or non-cyano-containing nitrification inhibitors that have one or more aldehyde reactive groups selected from the group consisting of a) primary, b) secondary amines, c) amides, d) thiols, e) hydroxyls and f) phenols. In another embodiment, the composition of a fertilizer may further comprise one or more members selected from the group consisting of: a) one of more biologically active agents and b) one or more biologics wherein the biologically active agents and biologics may possess one or more properties selected from the group consisting of urease inhibitors, nitrification inhibitor(s), pesticide(s), herbicide(s), fungicides(s), and insecticide(s). In a variation, when the fertilizer is applied to cropland and turf, the new liquid fertilizer additive composition makes the urea more effective in providing nutrients for plant growth over an extended period of time.

In an embodiment, a liquid fertilizer additive of biodegradable polymeric and/or oligomeric nitrification inhibitors is comprised of utilizing a NAPAOL as the reaction medium for the reaction of aldehyde(s) with cyano-containing nitrification inhibitors and/or non-cyano-containing nitrification inhibitors that have one or more aldehyde reactive groups selected from the group consisting of a) primary, b) secondary amines, c) amides, d) thiols, e) hydroxyls and f) phenols comprises DCD. In a variation, the NAPAOL comprises dimethyl sulfoxide.

In an embodiment, the composition of said liquid fertilizer additives comprises 5-80% the reaction product of aldehyde(s) reacted with cyano-containing nitrification inhibitors and/or non-cyano-containing nitrification inhibitors that have one or more aldehyde reactive groups selected from the group consisting of a) primary, b) secondary amines, c) amides, d) thiols, e) hydroxyls and f) phenols and 95-20% of a NAPAOL. In a variation, the composition may further comprise 0.05 to 50% of biologically active agents and/or biologics.

In an embodiment, a liquid fertilizer additive of biodegradable polymeric and/or oligomeric nitrification inhibitors comprises utilizing a NAPAOL as the reaction medium for the reaction of aldehyde(s) with cyano-containing nitrification inhibitors and/or non-cyano-containing nitrification inhibitors that have one or more aldehyde reactive groups selected from the group consisting of a) primary, b) secondary amines, c) amides, d) thiols, e) hydroxyls and f) phenols. In a variation, said liquid fertilizer additive composition may further comprise one or more organo polyorganic acids and/or their salts. In a variation, the composition of the polyacid one or more members selected from the group consisting of a monomer homopolymer, a copolymer and/or a terpolymer or one or more members selected from a group consisting of:
  aspartic acid
  glutamic acid
  maleic anhydride
  itaconic anhydride
  citraconic anhydride
  citric acid; or
  acrylic acid;
wherein the organo polyorganic acids are present in an amount that is about 5-50% of the total composition. In a variation, the cation of the salts of the polyacids comprise one or more metals selected from the group consisting of Na, K, Mg, Ca, Fe, Zn, Mn, Cu, Co, Mo, or Ni and one or more organoamine selected from the group consisting of mono $C_{1-6}$ amine, di $C_{1-6}$ amine, tri $C_{1-6}$ amine, mono ethanol amine, diethanol amine, triethanol amine, monoisopropyl amine, diisopropyl amine, triisopropyl amine, diethyl amine, diethylene triamine, triethyl tetraamine, tetraethyl pentamine.

In another variation, the composition comprised of said liquid fertilizer additives and said polyacids and/or their salts can be applied to natural and manmade nitrogen sources utilizing one or more application techniques selected from the group consisting of:
  a. coating a nitrogen source particle with said liquid fertilizer additives utilizing spraying, metering or slowly pouring onto a nitrogen source that is in a temperature range of −20° C. to 100° C. In a variation the mixing of the materials may be accomplished in a simple mixing tank mixing materials prior to use, using a metering system to inject materials simultaneously, or mixing via a spray injection system. In another variation, the mixture can be mixed in any common mixing tank, blenders and tumblers or on a conveyer belt. In another variation, the metering of all ingredients can be based on a weight, it may also be based on a volumetric basis,
  b. incorporating during the process a nitrogen source particle, granule and/or prill in which the liquid formulation can be added directly into the molten nitrogen source before formation of a particle, granule or a prill and/or sprayed into the prilling tower when molten nitrogen source is released from the top of prilling tower and the falling liquid nitrogen source is crystallized by air in the tower,
  c. dissolving liquid fertilizer additive into aqueous liquid fertilizers and
  d. incorporating said liquid fertilizer additives into non-aqueous liquid nitrogen sources such as pressurized anhydrous ammonia gas.

In a variation, said liquid formulations can be sprayed directly onto the soil and onto natural fertilizers such as manure.

In another variation, application of the composition comprised of said liquid fertilizer additives and said polyacids and/or their salts will improve the effectiveness of the treated fertilizer due to the slow release of nitrification inhibitors through the biodegradation of the polymer backbone resulting in the maintenance of an effective level of free nitrification inhibitors. In another variation, the presence of the organo polyacids and/or their salts will assist in freeing soil bound phosphates and micronutrients, provide a micronutrient transport and moisture protection in the root zone when injected subsurface in applications such as anhydrous ammonia. In another variation, the organo polyacids in an acid/anhydride/imide configuration can provide nitrogen conservation to the nitrogen source making the fertilizer more effective in providing nutrients for plant growth over an extended period of time.

In an embodiment, the capability of the NAPAOL to also serve as a non-aqueous organo solvent delivery system (abbreviated as NOSDS) allows the application of the liquid composition to nitrogen sources that utilize moisture sensitive application methods. It has been learned that liquid biodegradable polymeric and/or oligomeric nitrification inhibitors comprised of utilizing a non-aqueous polar, aprotic organo liquid (NAPAOL) as the reaction medium for the reaction of aldehyde(s) with cyano-containing nitrification inhibitors that have one or more aldehyde reactive groups selected from the group consisting of a) primary, b) secondary amines, c) amides, d) thiols, e) hydroxyls and f) phenols assist to conserve the cyano-group. In a variation, the liquid biodegradable polymeric and/or oligomeric nitrification inhibitors is comprised of utilizing a non-aqueous polar, aprotic organo liquid (NAPAOL) as the reaction medium for the reaction of aldehyde(s) with nitrification inhibitors that have one or more aldehyde reactive groups selected from the group consisting of a) primary, b) secondary amines, c) amides, d) thiols, e) hydroxyls and f) phenols can possess higher levels of polymer bound and free nitrification inhibitors versus products utilizing a NAPAOL to make solutions of free nitrification inhibitors. In a variation, it has been learned that utilizing a NAPAOL as the reaction medium results in higher compositional weight percent of said liquid biodegradable polymeric and/or oligomeric nitrification inhibitors versus those produced in an aqueous medium nitrification inhibitors.

In an embodiment, the compositions and methods of making a liquid fertilizer additive of biodegradable polymeric and/or oligomeric nitrification inhibitors are comprised of utilizing a non-aqueous polar, aprotic organo liquid (NAPAOL) as the reaction medium for the reaction of aldehyde(s) with cyano-containing nitrification inhibitors that have one or more aldehyde reactive groups selected from the group consisting of a) primary, b) secondary amines, c) amides, d) thiols, e) hydroxyls and f) phenols, wherein said liquid fertilizer additive is applied to the soil directly either before or after the application of a nitrogen source or in a composition with a nitrogen source inhibits the loss of the nitrogen source's nitrogen caused by the microbial process termed nitrification. In a variation, the method of making a liquid fertilizer additive of biodegradable polymeric and/or oligomeric nitrification inhibitors wherein the process parameters are optimized to conserve the cyano group of the nitrification inhibitor preventing it from being converted to diaminomethylene urea comprise a) controlling pH of the reaction, b) utilization of a NAPAOL as the reaction medium, c) using a two-step reaction strategy wherein the first reaction incorporates an aldehyde with a cyano-containing nitrification inhibitor that have one or more aldehyde reactive groups selected from the group consisting of i) primary, ii) secondary amines, iii) amides, iv) thiols, v) hydroxyls and vi) phenol to form methylol groups and the second is the reaction of the methylol group with an aldehyde reactive group of the nitrification inhibitor to form polymeric and/or oligomeric nitrification inhibitors and d) removing water during the second reaction resulting in improved nitrification inhibition properties.

In an embodiment, a liquid fertilizer additive comprised of biodegradable polymeric and/or oligomeric nitrification inhibitors resulting from the reaction of aldehyde(s) with cyano-containing nitrification inhibitors that have one or more aldehyde reactive groups selected from the group consisting of a) primary, b) secondary amines, c) amides, d) thiols, e) hydroxyls and f) phenols utilizing a NAPAOL as the reaction medium has improved nitrification inhibition properties when compared to its monomeric form.

In an embodiment, there is a maximum polymer weight of biodegradable polymeric and/or oligomeric nitrification inhibitors resulting from the reaction of aldehyde(s) with cyano-containing nitrification inhibitors that have one or more aldehyde reactive groups selected from the group consisting of a) primary, b) secondary amines, c) amides, d) thiols, e) hydroxyls and f) phenols utilizing a NAPAOL as the reaction medium wherein the viscosity, water solubility and biodegradability properties of the liquid fertilizer additive negatively impact nitrification inhibition.

In an embodiment, a liquid fertilizer additive comprised of a) biodegradable polymeric and/or oligomeric nitrification inhibitors resulting from the reaction of aldehyde(s) with cyano-containing nitrification inhibitors that have one or more aldehyde reactive groups selected from the group consisting of i) primary, ii) secondary amines, iii) amides, iv) thiols, v) hydroxyls and vi) phenols b) utilizing a NAPAOL as the reaction medium and c) one or more nitrification inhibitors selected from the group consisting of 2-chloro-6-trichloromethyl)pyridine, 4-amino-1,2,4-6-triazole-HCl, 2,4-diamino-6-trichloromethyltriazine CL-1580, dicyandiamide (DCD), thiourea, 1-mercapto-1,2,4-triazole, ammonium thiosulfate, dimethylpyrazole and/or its organic and inorganic salts and 2-amino-4-chloro-6-methylpyrimidine has improved nitrification inhibition properties when compared to the monomeric form of the added nitrification inhibitors. In a variation, the composition can further comprise protic and aprotic solvents.

In an embodiment, liquid fertilizer additives comprises:
1) a NAPAOL,
2) aldehydes
3) one or more nitrification inhibitors selected from the group consisting of 2-chloro-6-trichloromethyl)pyridine, 4-amino-1,2,4-6-triazole-HCl, 2,4-diamino-6-trichloromethyltriazine CL-1580, dicyandiamide (DCD), thiourea, 1-mercapto-1,2,4-triazole, ammonium thiosulfate, dimethylpyrazole and/or its organic and inorganic salts and 2-amino-4-chloro-6-methylpyrimidine,
4) one or more dicyandiamide-formaldehyde adducts selected from the group consisting of the following structures:
i)

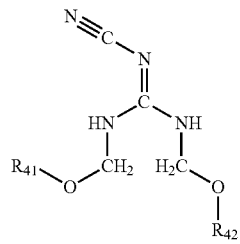

wherein $R_{41}$ & $R_{42}$=H or $CH_2$—$OR_{43}$
wherein $R_{43}$=H or —$CH_3$ to —$C_4H_9$ alkyl radical
ii)

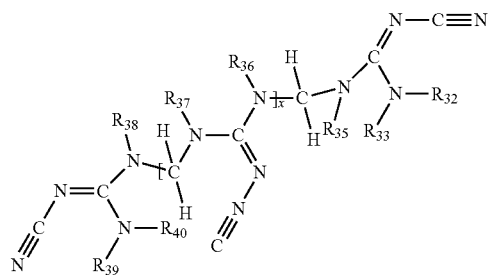

wherein X=0-10
wherein $R_{32}$, $R_{33}$, $R_{35}$, $R_{36}$, $R_{37}$, $R_{38}$, $R_{39}$, $R_{40}$ are independently selected from the group consisting of: H or $CH_2OR_{41}$
wherein $R_{41}$ is H or —$C_1H_3$ to —$C_4H_9$ alkyl radical
wherein the NAPAOL comprises one or more members selected from the group consisting of:
a) dimethyl sulfoxide,
b) and dialkyl, diaryl, or alkylaryl sulfoxide(s) having the formula:

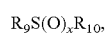

wherein $R_9$ and $R_{10}$ are each independently a $C_{1-6}$ alkylene group, an aryl group, or $C_{1-3}$alkylenearyl group or $R_9$ and $R_{10}$ together with the sulfur to which they are attached form a 4 to 8 membered ring wherein $R_9$ and $R_{10}$ together are a $C_{1-6}$ alkylene group which optionally contains one or more atoms selected from the group consisting of O, S, Se, Te, N, and P in the ring and x is 1 or 2,
c) and one or more alkylene carbonates selected from the group consisting of ethylene carbonate, propylene carbonate and butylene carbonate d) 1-Methyl-2-pyrrolidone, e) one or more organo phosphorous liquids selected from the group consisting of hexamethylphosphoramide and one or more trialkylphosphates selected from the group represented by the formula:

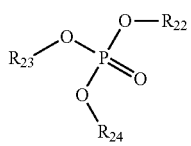

wherein:
$R_{22}$ is alkyl radical $—C_1H_3$ to $—C_6H_{13}$
$R_{23}$ is alkyl radical $—C_1H_3$ to $—C_6H_{13}$
$R_{24}$ is alkyl radical $—C_1H_3$ to $—C_6H_{13}$ f) 1,2-dimethyloxyethane, g) 2-methoxyethyl ether and h) cyclohexylpyrrolidone, wherein the one or more aldehydes are selected from the group consisting of:

methanal, ethanal, propanal, butanal, pentanal, hexanal, methylethanal, methylpropanal, methylbutanal, phenylacetaldehyde, benzaldehyde, 2-propenal, 3-oxopropanoic, 2-methyl-3-oxopropanoic acid, 4-oxobutanoic acid, oxoacetic acid, 5-oxopentanoic acid, 6-oxohexanoic acid, 2-oxopropanal, cyclohexanal, furfural, methyl esters of 3-oxopropanoic, 2-methyl-3-oxopropanoic acid, 4-oxobutanoic acid, oxoacetic acid, 5-oxopentanoic acid and 6-oxohexanoic acid, ethandial, 1,3-propanedial, butanedial, pentanedial, phthalaldehyde and methanethial, wherein the said liquid fertilizer composition can added to molten urea and/or ammonia resulting in an insitu modification of urea and/or ammonia within the urea manufacturing process, and wherein the NAPAOL would have urea solubilizing properties ensuring a more homogeneous distribution of nitrification inhibitors within the urea.

In a variation $R_{32}$-$R_{41}$ further comprise one or more members independently selected from the group consisting of: $CH_2$—Z, wherein Z=DCD or a DCD-formaldehyde adduct.

In a variation, the NAPAOL is dimethyl sulfoxide.

In an embodiment, a method of making liquid fertilizer additives of biodegradable polymeric and/or oligomeric nitrification inhibitors comprises utilizing a NAPAOL as the reaction medium for the reaction of aldehyde(s) with cyano-containing nitrification inhibitors that have one or more aldehyde reactive groups selected from the group consisting of a) primary, b) secondary amines, c) amides, d) thiols, e) hydroxyls and f) phenols is designed such that the aldehyde is reacted to its methylol function versus continued reaction with formaldehyde reactive groups crosslinking to the methylene function wherein the molar ratio is set to ensure that the aldehyde to aldehyde reactive groups ratio available in said cyano-containing nitrification inhibitors. In a variation, the methylol function can be capped to an alkoxy group comprising of —CH3 to —C4H9 alkyl radical —NI—CH2-OH vs NI—CH2-NI In an embodiment, the following drawings of dicyandiamide reacted with formaldehyde would represent desired structure formed versus crosslinking to the methylene function:

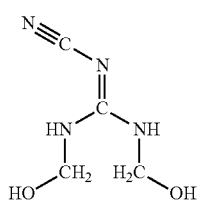

and/or

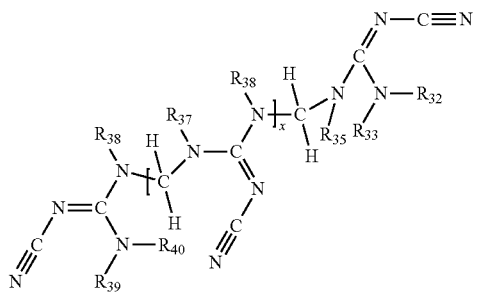

wherein X=0-10
wherein $R_{32}$, $R_{33}$, $R_{34}$, $R_{35}$, $R_{36}$, $R_{37}$, $R_{38}$, $R_{39}$, $R_{40}$ are independently selected from the group consisting of: H or $CH_2OR_{41}$
wherein $R_{41}$ is H or $—C_1H_3$ to $—C_4H_9$ alkyl radical
versus

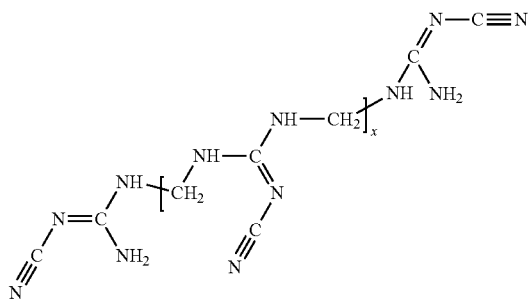

In an embodiment, the molar ratio of said aldehyde to said cyano-containing nitrification inhibitors' aldehyde reactive groups comprise 1:1 to 4:1. In a variation, the molar ratio of said aldehyde to said cyano-containing nitrification inhibitors is set with an excess of aldehyde groups to ensure reactive methylol groups present after the reaction is terminated. In a variation, the ratio of aldehyde groups to aldehyde reactive groups further comprise >4:1

In an embodiment, the reaction parameters and molar ratios can be set such that the formation of methylene bridges is limited resulting in a liquid fertilizer additive—AMC (aldehyde-methylol containing) comprising unreacted aldehyde, nitrification inhibitors and nitrification inhibitors-aldehyde reaction product containing methylol functions wherein the method to make may comprise 1) dissolving the nitrification inhibitor in NAPAOL at temperatures in the range of 20-110° C. and cooling to 20-60° C. and ensuring that pH is in the range of 8-10, 2) slowly adding the aldehyde and allowing the exotherm to be controlled either through charge rate or removing the heat of reaction through a cooling medium while holding the temperature at 40-60° C., 3) Heat vessel contents at 60-100° C. for 2 to 18 hours and then cool to <40° C. In a variation, the nitrification inhibitor is dissolved in a NAPAOL at 20-80° C. and the aldehyde is subsequently dispersed into the dissolved and/or dispersed nitrification inhibitor wherein the composition is a liquid fertilizer additive-A (aldehyde).

In a variation, the reaction parameters and molar ratios can be set such that the formation of methylene bridges is limited resulting in a liquid fertilizer additive-AMC comprising unreacted aldehyde, nitrification inhibitors and/or nitrification inhibitors-aldehyde reaction product containing methylol functions wherein the method to make may comprise 1) charging the nitrification inhibitor and aldehyde in a NAPAOL at temperatures in the range of 20-40° C. and then removing oxygen from the vessel's headspace, 2) slowly heat vessel contents to 60-100° C., 3) Hold at 60-100° C. for 2 to 18 hours and then cool to <40° C.

In an embodiment, a liquid fertilizer additive—AMC and or a liquid fertilizer-A can be added to molten urea, molten urea/ammonia and ammonia to disperse into the nitrogen source and react with the urea, urea and ammonia and ammonia incorporating nitrification inhibitors into the backbone of a urea-formaldehyde and/or a urea-ammonia-formaldehyde polymer with even distribution of the nitrification inhibitor throughout the resulting polymer.

The reaction parameters and molar ratios can be set such that the formation of methylene bridges is favored, the said nitrification inhibitors-aldehyde adduct can be further reacted with an aldehyde resulting in a liquid fertilizer additive comprising unreacted aldehyde, nitrification inhibitors, nitrification inhibitors-aldehyde reaction product and nitrification inhibitors-aldehyde reaction product containing methylol functions wherein the method to make comprises one or more of the following steps selected from the group consisting of:
  a) charging said aldehydes, said nitrification inhibitors and said NAPAOL to reaction vessel and start mixing,
  b) heating contents of the vessel to 50-90° C. and hold at temperature for 1-7 hours,
  c) cooling to 40-60° C., charging an acid catalyst such as but not limited to one or more members selected from the group consisting of methane sulfonic acid, sulfuric acid, para-toluene sulfonic acid phosphoric acid and methane phosphonic acid, placing reaction vessel under a vacuum of 0.5-50 mm, increasing temperature to 90-120° C. and hold under vacuum and at temperature until distillation ceases, cool to 40° C.,
  d) adjust pH to 8-10 with 10% NaOH or KOH and then 10-200% more aldehyde calculated on the amount of initial aldehyde charged,
  e) Heat contents of vessel to 70-80° C. and hold for 1-5 hours,
  f) Optional to cool batch below 40° C. for storage, In a variation, the material from step "d" can be added as is to molten urea, molten urea/ammonia and ammonia to disperse into the nitrogen source and react with the urea, urea and ammonia and ammonia incorporating blocks of nitrification inhibitors into the backbone of a urea-formaldehyde and/or a urea-ammonia-formaldehyde polymer. In another variation, the polymeric/oligomeric nitrification inhibitor comprises dicyandiamide wherein when added to a molten nitrogen source can form hydrophobic DCD blocks creating zones of water resistance within the resulting urea particle, In another variation, the material from step "e" can be added as is to molten urea, molten urea/ammonia and ammonia to disperse into the nitrogen source and react with the urea, urea and ammonia and ammonia incorporating blocks of nitrification inhibitors into the backbone of a urea-formaldehyde and/or a urea-ammonia-formaldehyde polymer. In another variation, the polymeric/oligomeric nitrification inhibitor comprises dicyandiamide segments wherein when added to a molten nitrogen source can form hydrophobic DCD blocks creating zones of water resistance within the resulting urea particle.

In an embodiment, the nitrogen source fertilizer particles formed from the urea and/or urea-ammonia molten liquid containing the insitu polymerization of the urea and urea ammonia with the liquid fertilizer additives that comprise:
  1) a NAPAOL,
  2) aldehydes
  3) one or more nitrification inhibitors selected from the group consisting of 2-chloro-6-trichloromethyl)pyridine, 4-amino-1,2,4-6-triazole-HCl, 2,4-diamino-6-trichloromethyltriazine CL-1580, dicyandiamide (DCD), thiourea, 1-mercapto-1,2,4-triazole, ammonium thiosulfate, dimethylpyrazole and/or its organic and inorganic salts and 2-amino-4-chloro-6-methylpyrimidine,
  4) one or more dicyandiamide-formaldehyde adducts selected from the group consisting of the following structures:
  i)

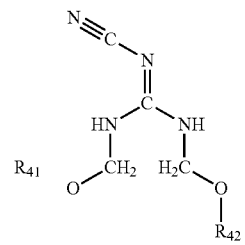

wherein $R_{41}$ & $R_{42}$=H or $CH_2$—$OR_{43}$
wherein $R_{43}$=H or —$CH_3$ to —$C_4H_9$ alkyl radical
ii)

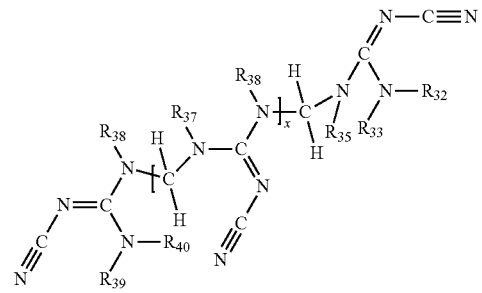

wherein X=0-10
wherein $R_{32}$, $R_{33}$, $R_{34}$, $R_{35}$, $R_{36}$, $R_{37}$, $R_{38}$, $R_{39}$, $R_{40}$ are independently selected from the group consisting of: H or $CH_2OR_{41}$
wherein $R_{41}$ is H or —$C_1H_3$ to —$C_4H_9$ alkyl radical
wherein the NAPAOL comprises one or more members selected from the group consisting of:
  a) dimethyl sulfoxide,
  b) and dialkyl, diaryl, or alkylaryl sulfoxide(s) having the formula:

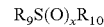

wherein $R_9$ and $R_{10}$ are each independently a $C_{1-6}$ alkylene group, an aryl group, or $C_{1-3}$alkylenearyl group or $R_9$ and $R_{10}$ together with the sulfur to which they are attached form a 4 to 8 membered ring wherein $R_9$ and $R_{10}$ together are a $C_{1-6}$ alkylene group which optionally contains one or more atoms selected from the group consisting of O, S, Se, Te, N, and P in the ring and x is 1 or 2,
  c) and one or more alkylene carbonates selected from the group consisting of ethylene carbonate, propylene carbonate and butylene carbonate d) 1-Methyl-2-pyrrolidone, e) one or more organo phosphorous liquids selected from the group consisting of hexamethylphosphoramide and one or more trialkylphosphates selected from the group represented by the formula:

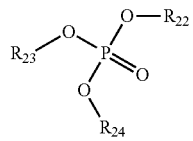

wherein:

$R_{22}$ is alkyl radical —$C_1H_3$ to —$C_6H_{13}$ $R_{23}$ is alkyl radical —$C_1H_3$ to —$C_6H_{13}$ $R_{24}$ is alkyl radical —$C_1H_3$ to —$C_6H_{13}$ f) 1,2-dimethyloxyethane, g) 2-methoxyethyl ether and h) cyclohexylpyrrolidone, wherein the one or more aldehydes are selected from the group consisting of:

methanal, ethanal, propanal, butanal, pentanal, hexanal, methylethanal, methylpropanal, methylbutanal, phenylacetaldehyde, benzaldehyde, 2-propenal, 3-oxopropanoic, 2-methyl-3-oxopropanoic acid, 4-oxobutanoic acid, oxoacetic acid, 5-oxopentanoic acid, 6-oxohexanoic acid, 2-oxopropanal, cyclohexanal, furfural, methyl esters of 3-oxopropanoic, 2-methyl-3-oxopropanoic acid, 4-oxobutanoic acid, oxoacetic acid, 5-oxopentanoic acid and 6-oxohexanoic acid, ethandial, 1,3-propanedial, butanedial, pentanedial, phthalaldehyde and methanethial, wherein the said liquid fertilizer composition can added to molten urea and/or ammonia resulting in an insitu modification of urea and/or ammonia within the urea manufacturing process, and wherein the NAPAOL would have urea solubilizing properties ensuring a more homogeneous distribution of nitrification inhibitors within the urea.

have one or more properties selected from the group consisting of higher crush resistance lower water solubility due to the formation of zones of water resistance nitrification inhibition extended available of nitrogen in a plant available form reduced migration of nitrification inhibitor through the soil In a variation, the resulting polymers formed have through the in situ polymerization method of making have better distribution of DCD within the polymer/oligomer structure ensuring lower levels of free DCD within the fertilizer nitrogen source particles and extending the availability of the nitrogen from the fertilizer in a plant available form.

In another variation, because of the slower release of the nitrification inhibitors into the soil due to poorer water solubility and to the time for biodegradation of the nitrification inhibitor-formaldehyde adduct that has been further reacted with urea and/or urea-ammonia, increased levels of application of the said liquid fertilizer additive can be added with improved benefits from additional nitrification inhibition.

In an embodiment, a composition of a fertilizer additive of biodegradable polymeric and/or oligomeric nitrification inhibitors is comprised of DCD and one or more members selected from the group consisting of:

a) Modified DCD represented by the structure

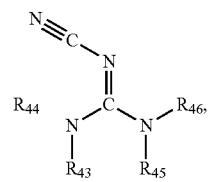

wherein $R_{43}$, $R_{44}$, $R_{45}$ and $R_{46}$ are one or more members independently selected from the group consisting of: H and —$CH_2OH$ b) a methylene bis dicyandiamide represented by the structure:

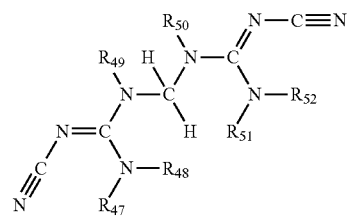

wherein $R_{47}$, $R_{48}$, $R_{49}$ $R_{50}$, $R_{51}$ and $R_{52}$ are one or more members independently selected from the group consisting of: H, and —$CH_2OH$ c) a trimer of a dicyandiamide-formaldehyde reaction product represented by the structure:

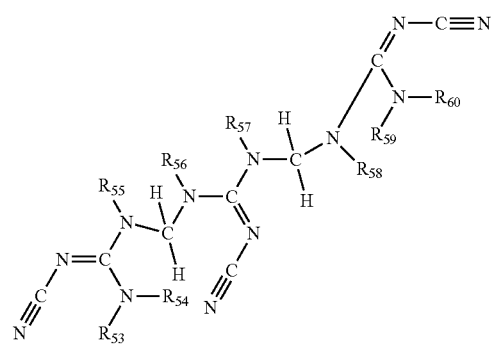

wherein $R_{53}$, $R_{54}$, $R_{55}$, $R_{56}$, $R_{57}$, $R_{58}$, $R_{59}$ and $R_{60}$ are one or more members independently selected from the group consisting of: H and —$CH_2OH$ d) and a polymer of a dicyandiamide-formaldehyde reaction product represented by the structure:

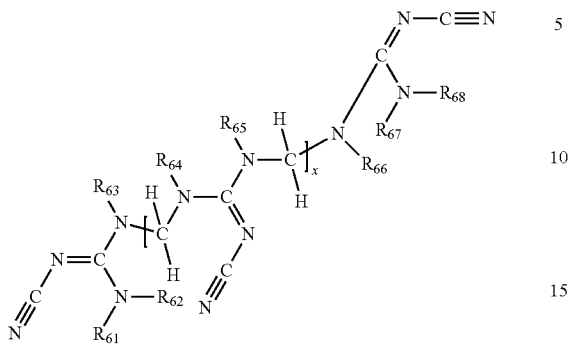

wherein $R_{61}$, $R_{62}$, $R_{63}$, $R_{64}$, $R_{65}$, $R_{66}$, $R_{67}$ and $R_{68}$ are one or more members independently selected from the group consisting of: H and —CH$_2$OH e) Formaldehyde In a variation, it is recognized that generic dicyandiamide structure as described herein also has tautomer shown below:

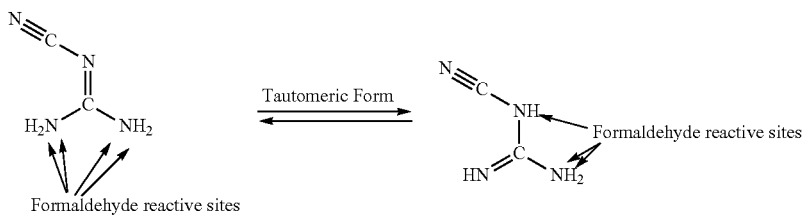 [SMILES: N#CN=C(N)N ; N#CNC(=N)N]

and therefore both are included in structural description.

In an embodiment, the compositions and methods of making nitrification inhibitors are comprised of DCD and one or more members selected from the group consisting of:

f) Modified DCD represented by the structure

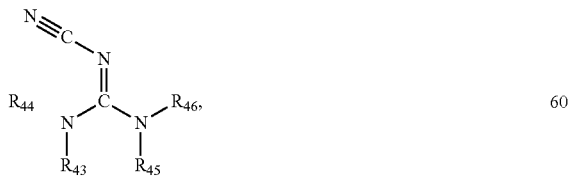

wherein $R_{43}$, $R_{44}$, $R_{45}$ and $R_{46}$ are one or more members independently selected from the group consisting of: H and —CH$_2$OH g) a methylene bis dicyandiamide represented by the structure:

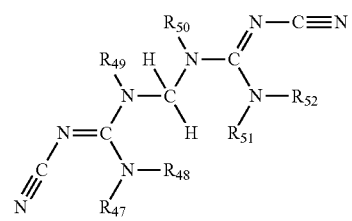

wherein $R_{47}$, $R_{48}$, $R_{49}$ $R_{50}$, $R_{51}$ and $R_{52}$ are one or more members independently selected from the group consisting of: H, and —CH$_2$OH h) a trimer of a dicyandiamide-formaldehyde reaction product represented by the structure:

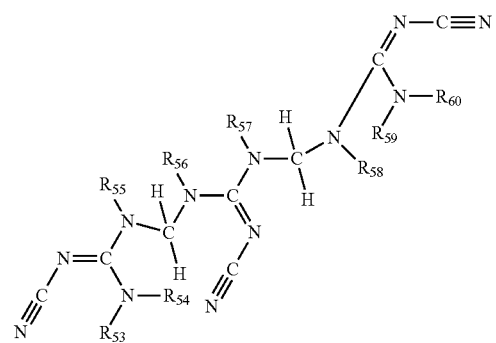

wherein $R_{53}$, $R_{54}$, $R_{55}$, $R_{56}$, $R_{57}$, $R_{58}$, $R_{59}$ and $R_{60}$ are one or more members independently selected from the group consisting of: H and —CH$_2$OH i) and a polymer of a dicyandiamide-formaldehyde reaction product represented by the structure:

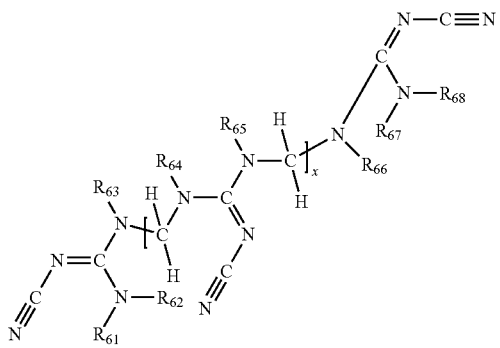

wherein $R_{61}$, $R_{62}$, $R_{63}$, $R_{64}$, $R_{65}$, $R_{66}$, $R_{67}$ and $R_{68}$ are one or more members independently selected from the group consisting of: H and —CH$_2$OH and wherein x=2-20 j) Formaldehyde.

The compositions and methods of the instant invention are comprised of a) utilizing one or more non-aqueous polar, aprotic organo liquid (NAPAOL) selected from the group consisting of:

a) dimethyl sulfoxide, b) an dialkyl, diaryl, or alkylaryl sulfoxide(s) having the formula:

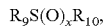

wherein $R_9$ and $R_{10}$ are each independently a $C_{1-6}$ alkylene group, an aryl group, or $C_{1-3}$alkylenearyl group or $R_9$ and $R_{10}$ together with the sulfur to which they are attached form a 4 to 8 membered ring wherein $R_9$ and $R_{10}$ together are a $C_{1-6}$ alkylene group which optionally contains one or more atoms selected from the group consisting of O, S, Se, Te, N, and P in the ring and x is 1 or 2, c) one or more alkylene carbonates selected from the group consisting of ethylene carbonate, propylene carbonate and butylene carbonate d) 1-Methyl-2-pyrrolidone, e) one or more organo phosphorous liquids selected from the group consisting of hexamethylphosphoramide and one or more trialkylphosphates selected from the group represented by the formula:

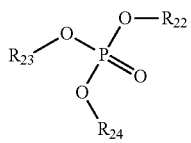

wherein:
$R_{22}$ is alkyl radical —C$_1$H$_3$ to —C$_6$H$_{13}$
$R_{23}$ is alkyl radical —C$_1$H$_3$ to —C$_6$H$_{13}$
$R_{24}$ is alkyl radical —C$_1$H$_3$ to —C$_6$H$_{13}$ f) 1,2-dimethyloxyethane, g) 2-methoxyethyl ether and h) cyclohexylpyrrolidone, as the reaction medium for the reaction of formaldehyde with dicyandiamide wherein said nitrification inhibitor composition is applied to the soil directly either before or after the application of a nitrogen source or in a composition with a nitrogen source to inhibit the loss of the nitrogen source's nitrogen caused by the microbial process termed nitrification.

In a variation, the method of making said nitrification inhibitor compositions wherein the process parameters are optimized to conserve the cyano group of the nitrification inhibitor preventing it from being converted to diaminomethylene urea comprise a) controlling pH of the reaction, b) utilization of a NAPAOL as the reaction medium, c) using a two-step reaction strategy wherein the first reaction incorporates formaldehyde with dicyandiamide forming a methylol group and the second is the reaction of the methylol group with an aldehyde reactive group dicyandiamide to form polymeric and/or oligomeric nitrification inhibitor composition and d) removing water during the second reaction resulting in improved nitrification inhibition properties.

In an embodiment, a fertilizer comprises one or more nitrogen sources selected from the group consisting of a) urea, b) urea formaldehyde reaction products, c) ammonia, d) urea formaldehyde and ammonia reaction products, e) ammonium nitrate, f) ammonium sulfate, e) manure and f) compost liquid, and a nitrification inhibitor composition is comprised of DCD and one or more nitrification inhibitors selected from the group consisting of:

a) Modified DCD represented by the structure

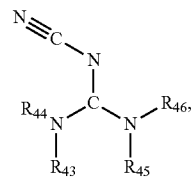

wherein $R_{43}$, $R_{44}$, $R_{45}$ and $R_{46}$ are one or more members independently selected from the group consisting of: H and —CH$_2$OH b) a methylene bis dicyandiamide represented by the structure:

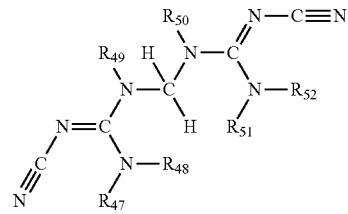

wherein $R_{47}$, $R_{48}$, $R_{49}$ $R_{50}$, $R_{51}$ and $R_{52}$ are one or more members independently selected from the group consisting of: H, and —CH$_2$OH c) a trimer of a dicyandiamide-formaldehyde reaction product represented by the structure:

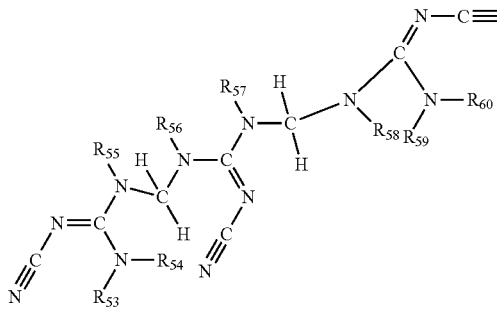

wherein $R_{53}$, $R_{54}$, $R_{55}$, $R_{56}$, $R_{57}$, $R_{58}$, $R_{59}$ and $R_{60}$ are one or more members independently selected from the group consisting of: H and —$CH_2OH$ d) and a polymer of a dicyandiamide-formaldehyde reaction product represented by the structure:

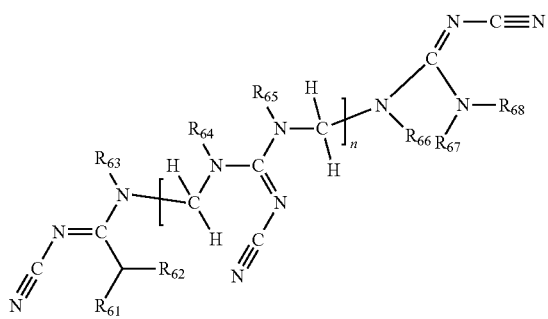

wherein $R_{61}$, $R_{62}$, $R_{63}$, $R_{64}$, $R_{65}$, $R_{66}$, $R_{67}$ and $R_{68}$ are one or more members independently selected from the group consisting of: H and —$CH_2OH$ and x=2-20, e) Formaldehyde.

In a variation, said nitrification inhibitor composition can be applied to a nitrogen source through a coating or spraying application, added to the urea during the urea production process either in the melt portion or deposited to the urea during the formation of the urea granule when the urea is still hot, blended into liquefied ammonia gas and added to an aqueous fertilizers such as UAN. In a variation, application levels of said nitrification inhibitors comprise 0.05-10% of the nitrogen source composition. In another variation, the NAPAOL comprises 0.01-9.5% of the fertilizer composition.

In an embodiment, when a nitrification inhibitor containing methylol groups is added to a molten urea, the methylol groups can further react with urea, chemically incorporating the nitrification inhibitors composition into the urea granule. In a variation, the urea particle will have better physical properties, more hydrophobic and contain slow release nitrification inhibitors in combination with more traditional inhibitors. In a variation, the nitrification inhibitor compositions can be added to molten urea and/or to the surface of the resulting hot urea particle aiding in slowing down the dissolution of the urea particle.

The following references are incorporated by reference in their entireties for all purposes.

| | |
|---|---|
| 3,264,089 | Hansen |
| 3,342,577 | Blauin |
| 3,475,154 | Kato |
| 5,219,465 | Goertz |
| 5,538,531 | Hudson |
| 5,599,374 | Detrick |
| 5,653,782 | Stern |
| 5,803,946 | Petcavich |
| 6,338,746 | Detrick |
| 6,663,686 | Geiger |
| 9,440,890 | Gabrielson |
| 20100011825 | Ogle |
| 20040016276 | Wynnyk |
| CN104803807 | Yuan |
| CN 104446875 | Li |
| CN 104609983 | Chen |
| 4,551,166 | Behnke |

Baligar V C, B. O. (1986). "NPK-fertilizer efficiency—a situation analysis for the tropics." Fertilizer Research 10(2): 147-164.

Bennett E M, C. S. a. C. N. (2001). "Human Impact on Erodable Phosphorus and Eutrophication: A Global Perspective Increasing accumulation of phosphorus in soil threatens rivers, lakes, and coastal oceans with eutrophication." BioScience 51: 227-234.

Christians, N. (2004). ""Fertilization". Fundamentals of Turfgrass Management (2nd ed.)." 137-138.

Dobermann, A. and K. G. Cassman (2005). "Cereal area and nitrogen use efficiency are drivers of future nitrogen fertilizer consumption." Sci China C Life Sci 48 Spec No: 745-758.

Fan, X., Li, F., Liu, F., and Kumar, D. (2004). "Fertilization with a new type of coated urea: Evaluation for nitrogen efficiency and yield in winter wheat." J. Plant Nutr. 27: 853-865.

Kross, B. C., et al. (1993). "The nitrate contamination of private well water in Iowa." Am J Public Health 83(2): 270-272.

TLAL (1998). "Soil quality and agricultural sustainability." 58.

Linsay, W. (1979). "Chemical Equilibrium in Soils."

S, S. (2012). "An Agricultural Pollutant: Chemical Fertilizer." International Journal of Environmental Science and Development 3(1): 77.

Ebisuno, Takimoto, Takahashi, Shiba, (1993) "Preparation and Structure of a Tetrasubstituted Derivative of N'''—Cyanoguanidine, N,N,N',N'-Tetrabenzyl-N''-cyanoguanidine."

It should be understood that the present invention is not to be limited by the above description. Modifications can be made to the above without departing from the spirit and scope of the invention. It is contemplated and therefore within the scope of the present invention that any feature that is described above can be combined with any other feature that is described above. Moreover, it should be understood that the present invention contemplates minor modifications that can be made to the formulations, compositions, fertilizer additives and methods of the present invention. When ranges are discussed, any number that may not be explicitly disclosed but fits within the range is contemplated as an endpoint for the range. For example, if a range of 35-60 is given, it should be understood, that any number between 35 and 60 can be used as the end point for said range (e.g., 36, 37, 38, etc.). Moreover, if a list of species within a genus are listed, it is contemplated that any particular species or any group of species within the genus is contemplated as being a subgenus that fits within the scope of the invention. The scope of protection to be afforded is to be determined by the claims which follow and the breadth of interpretation which the law allows.

We claim:

1. A nitrification inhibitor composition comprising one or more members selected from the structures consisting of:

a)

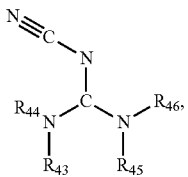

wherein $R_{43}$, $R_{44}$, $R_{45}$ and $R_{46}$ are one or more members independently selected from the group consisting of: H and —$CH_2OH$ wherein at least one of $R_{43}$, $R_{44}$, $R_{45}$ and $R_{46}$ is $CH_2OH$, b)

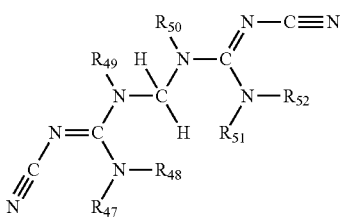

wherein $R_{47}$, $R_{48}$, $R_{49}$ $R_{50}$, $R_{51}$ and $R_{52}$ are one or more members independently selected from the group consisting of: H, and —$CH_2OH$ and, c)

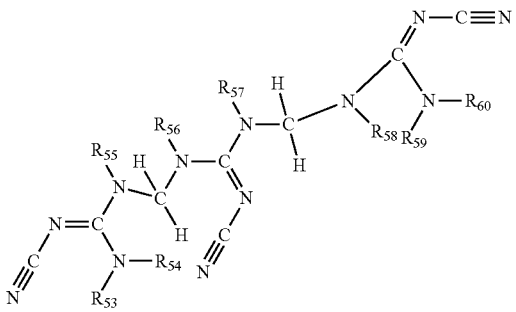

wherein $R_{53}$, $R_{54}$, $R_{55}$, $R_{56}$, $R_{57}$, $R_{58}$, $R_{59}$ and $R_{60}$ are one or more members independently selected from the group consisting of: H and —$CH_2OH$, wherein said structures are made by using non-aqueous conditions, and wherein the structures comprise more than 10% by weight of the nitrification inhibitor composition.

2. The composition of claim 1, wherein the composition further comprises the structure:

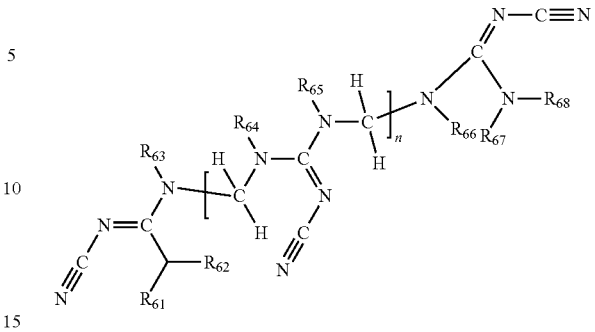

wherein $R_{61}$, $R_{62}$, $R_{63}$, $R_{64}$, $R_{65}$, $R_{66}$, $R_{67}$ and $R_{68}$ are one or more members independently selected from the group consisting of: H and —$CH_2OH$ wherein x is 2-20.

3. The composition of claim 1, wherein the composition further comprises one or more members selected from the group consisting of paraformaldehyde, dicyandiamide (DCD) and formaldehyde.

4. The composition of claim 1, wherein the nitrification inhibitor composition further comprises one or more members selected from the group consisting of a) ammonia, b) one or more polyamines, c) one or more polyols, d) one or more primary amines, e) one or more secondary amines, f) one or more $C_{1-10}$ alkanols, and one or more non-cyano containing nitrification inhibitors wherein
said one or more polyamines are selected from the group consisting of ethylenediamine, diethylenetriamine, triethylenetetramine, tetraethylenepentamine and aminoethylethanolamine, and wherein the polyamines comprise 0.01-5% of a polymer composition weight,
wherein said one or more polyols are selected from the group consisting of trimethylol propane, trimethylol ethane, pentaerythritol, sorbitol, sorbitan, glucose, fructose, galactose, glycerin, poly($C_{1-10}$ alkylene) glycols, ethylene, 1,3 propylene glycol, 1,2 propylene glycol, butylene glycol, isopropylidene glycerol, tripropylene glycol methyl ether, tripropylene glycol butyl ether, dipropylene glycol butyl ether, and tripropylene glycol butyl ether wherein the polyols comprise 0.1-5% of the polymer weight,
wherein said one or more secondary amines are selected from the group consisting of diethanolamine, diethylamine, cyclohexylamine, methylethanolamine, diisopropanolamine, methylispropylamine wherein the secondary amines comprise 0.1-5% of the polymer composition,
wherein said one or more $C_{1-10}$ alkanols are selected from the group consisting of methanol, ethanol, butanol, pentanol, and hexanol wherein said one or more C alkanols comprise 0.1-5% of the polymer composition weight,
wherein said one or more non-cyano containing nitrification inhibitors are selected from the group consisting of:
1) one or more pyrazoles represented by the structure:

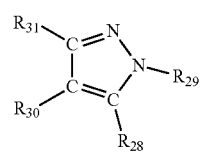

wherein R$_{28}$=—H, —CH$_3$, —CH$_2$CH$_3$, —NH$_2$ or —NHCH$_3$, wherein R$_{29}$=—H, —OH, —SH, —CONH$_2$ or —CONHCH$_3$, wherein R$_{30}$=—H, —CH$_3$, —CH$_2$CH$_3$, —NH$_2$ or —NHCH$_3$ and wherein R$_{31}$=—H, —CH$_3$, —CH$_2$CH$_3$, —NH$_2$ or —NHCH$_3$, and 2) one or more members selected from the group consisting of 2-amino-4-chloro-6-methyl-pyrimidine, 1,3-benzothiazole-2-thiol, 4-amino-N-1,3-thiazol-2-ylbenzenesulfonamide, thiourea, 2,4-diamino-6-trichloromethyl-5-triazine, 4-amino-1,2,4-triazole, 3-mercapto-1,2,4-triazole, and 2,3-dihydro-2,2-dimethyl-7-benzofuranol methyl-carbamate.

5. The composition of claim 1, wherein the composition further comprises one or more members selected from the group consisting of surfactants, buffers, fragrance/odor masking agents, colorants, flow modifiers, silicas, and hydrophobized silicas.

6. The composition of claim 1, wherein the composition further comprises one or more members selected from the group consisting of:
i. one or more biologics selected from the group consisting of: i) *Bacillus* biologics, ii) *Azospirillum* biologics, iii) *Azobacter* biologics iv) *Gluconacetobacter* biologics, v) *Phosphobacteria*, vi) *Cyanobacteria*, vii) *Herbaspirillum*, viii) *Burkholderia*, ix) *Pseudomonas*, x) *Gluconacetobacter*, xi) *Enterobacter*, xii) *Klebsiella*, xiii) *Burkholderia*, xiv) *Bradyrhiwbium* species, xv) *Bradyrhiwbium japonicum*, xvi) *Rhizobium meliloti*, xvii) *Laccaria bicolor*, xviii) *Glomus imraradices timanita*, xix) *Actinomyces*, xx) *Penicillium*, xxi) *Mesorhizobiwn cicero*, xxii) one or more insecticidal or insect repellent microbial species and strains selected from the group consisting of:
*Telenomus podisi, Baculovirus anticarsia; Trichogramma pretiosum, Trichogramma gallai, Chromobacterium subtsugae, Trichoderma fertile, Beauveria bassiana, Beauveria bassiana, Beauveria bassiana, Paecilomyces jknwsoroseu, Trichoderma harzianum, Verticillium lecanii, lsarfofumosarosea Lecanicillium muscarium, Streptomyces microflavus*, and *Muscodor albus*,
xxiii) one or more nematodal microbial species and strains selected from the group consisting of:
*Myrothecium verrucaria, Pasteuria* species, *Pasteuria Metarhizium* species, and *Flavobacteriwn* species
xxiv) *Reynoutria sachalinensis* and
xxv) one or more antifungal, antimicrobial and/or plant growth promoting microbial species and strains selected from the group consisting of:
*Gliocladium* species, *Pseudomonas* species selected from the group consisting of:
*Pseudomonas fluorescens, Pseudomonas fluorescens. putida* and *P. chlororaphis, Pseudomonasfluorescens* VP5, *Pseudomonas diazotrophicus, Enterobacter cloacae, Trichodema* species, *Trichoderma virens, Trichoderma atroviride* strains, *Coniothyrium minitans, Gliocladium* species, *Gliacladium virens, Gliacladium roseum*, and *Trichodemw harzianum* species,
ii. and one or more biologically active agents selected from the group consisting of:
i) one or more urease inhibitors selected from the group consisting of aliphatic phosphoric triamide, phosphoramides, N-alkyl thiophosphoric triamides, (aminomethyl)phosphinic acids and their salts and aminomethyl (alkylaminomethyl)phosphinic acids and their salts,
ii) one or more nitrification inhibitors selected from the group consisting of 2-chloro-6-trichloromethyl)pyridine, 4-amino-1,2,4,6-triazole-HCl, 2,4-diamino-6-trichloromethyltriazine CL-1580, dicyandiamide (DCD), thiourea, 1-mercapto-1,2,4-triazole, ammonium thiosulfate, dimethylpyrazole organic and inorganic salts, and 2-amino-4-chloro-6-methylpyrimidine,
iii) and pesticides, herbicides, fungicides(s), and insecticide(s).

7. The composition of claim 1, wherein the composition further comprises one or more organo polyorganic acids and/or their salts, wherein the organo polyorganic acids and/or their salts is a monomer homopolymer, a copolymer and/or a terpolymer and is one or more members selected from the group consisting of:
aspartic acid
glutamic acid
maleic anhydride
itaconic anhydride
citraconic anhydride
citric acid; and
acrylic acid;
wherein the organo polyorganic acids are present in an amount that is about 5-50% of a total composition and wherein a cation of salts of the polyacids comprise one or more members selected from the group consisting of one or more metals and one or more organoamines wherein the one or more metals are selected from the group consisting of Na, K, Mg, Ca, Fe, Zn, Mn, Cu, Co, Mo, and Ni and wherein the one or more organoamines are selected from the group consisting of mono C$_{1-6}$ amine, di C$_{1-6}$ amine, tri C$_{1-6}$ amine, mono ethanol amine, diethanol amine, triethanol amine, monoisopropyl amine, diisopropyl amine, triisopropyl amine, and diethyl amine.

8. The composition of claim 1, further comprising soil, wherein said nitrification inhibitor composition is applied to the soil directly either before or after the application of a nitrogen source or in a composition with a nitrogen source to inhibit the loss of the nitrogen source's nitrogen caused by a microbial process of nitrification.

9. A fertilizer composition comprising:
a. one or more nitrogen sources selected from the group consisting of: i) urea, ii) urea formaldehyde reaction products, iii) ammonia, iv) urea formaldehyde and ammonia reaction products, v) ammonium nitrate, vi) ammonium sulfate, vii) manure viii) compost and ix) treated urea and
b. a nitrification inhibitor composition comprising one or more members selected from the structures consisting of:
1.

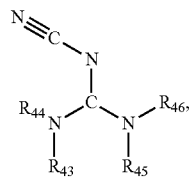

wherein $R_{43}$, $R_{44}$, $R_{45}$ and $R_{46}$ are one or more members independently selected from the group consisting of: H and —$CH_2OH$ wherein at least one of $R_{43}$ $R_{44}$, $R_{45}$ and $R_{46}$ is —$CH_2OH$,

2.

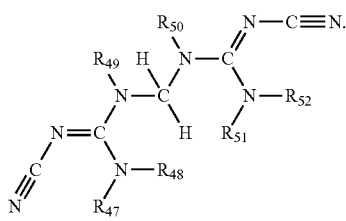

wherein $R_{47}$ $R_{48}$, $R_{49}$ $R_{50}$, $R_{51}$ and $R_{52}$ are one or more members independently selected from the group consisting of: H, and —$CH_2OH$, and

3.

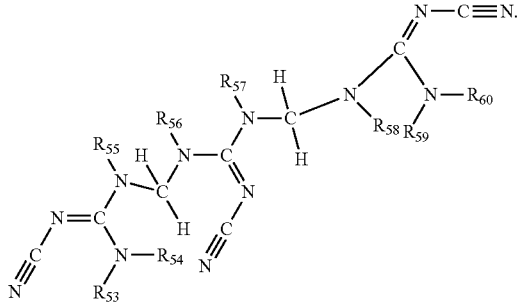

wherein $R_{53}$, $R_{54}$, $R_{55}$, $R_{56}$, $R_{57}$, $R_{58}$, $R_{59}$ and $R_{60}$ are one or more members independently selected from the group consisting of: H and —$CH_2OH$, wherein the nitrification inhibitor comprises 0.05-10% of the fertilizer composition, and wherein said structures are made by using non-aqueous conditions, and wherein the structures comprise more than 10% by weight of the nitrification inhibitor composition.

10. The composition of claim 9, wherein the composition of the nitrogen source comprises one or more members selected from the group consisting of urea and ammonium nitrate.

11. The composition of claim 10, wherein the composition further comprises water.

12. The composition of claim 9, wherein the nitrification inhibitor composition further comprises the structure:

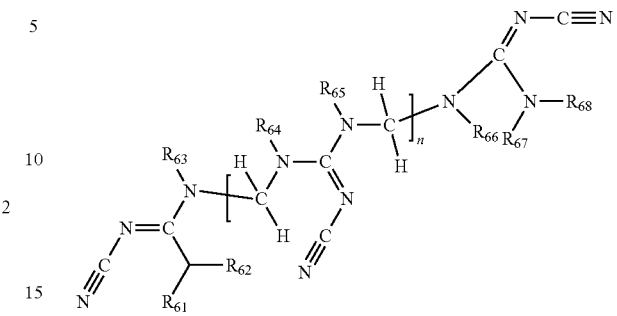

wherein $R_{61}$, $R_{62}$, $R_{63}$, $R_{64}$, $R_{65}$, $R_{66}$, $R_{67}$ and $R_{68}$ are one or more members independently selected from the group consisting of: H and —$CH_2OH$ wherein x is 2-20.

13. The composition of claim 9, wherein the nitrification inhibitor composition further comprises one or more members selected from the group consisting of paraformaldehyde, DCD and formaldehyde.

14. The composition of claim 9, wherein the nitrification inhibitor composition further comprises one or more members selected from the group consisting of a) ammonia, b) one or more polyamines, c) one or more polyols, d) one or more primary amines, e) one or more secondary amines, f) one or more $C_{1-10}$ alkanols, and one or more non-cyano containing nitrification inhibitors wherein
one or more polyamines are selected from the group consisting of ethylenediamine, diethylenetriamine, triethylenetetramine, tetraethylenepentamine and aminoethylethanolamine, and wherein the polyamines comprise 0.01-5% of a polymer composition weight,
wherein one or more polyols are selected from the group consisting of trimethylol propane, trimethylol ethane, pentaerythritol, sorbitol, sorbitan, glucose, fructose, galactose, glycerin, poly($C_{1-10}$ alkylene) glycols, ethylene, 1,3 propylene glycol, 1,2 propylene glycol, butylene glycol, isopropylidene glycerol, tripropylene glycol methyl ether, tripropylene glycol butyl ether, dipropylene glycol butyl ether, and tripropylene glycol butyl ether wherein the polyols comprise 0.1-5% of the polymer weight,
wherein one or more secondary amines are selected from the group consisting of diethanolamine, diethylamine, cyclohexylamine, methylethanolamine, diisopropanolamine, methylispropylamine wherein the secondary amines comprise 0.1-5% of the polymer composition,
wherein one or more low molecular weight alcohols are selected from the group consisting of methanol, ethanol, butanol, pentanol, and hexanol wherein the low molecular weight alcohols comprise 0.1-5% of the polymer composition weight,
wherein one or more non-cyano containing nitrification inhibitors are selected from the group consisting of:
1) one or more pyrazoles represented by the structure:

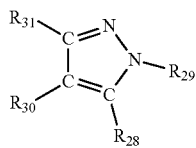

wherein $R_{28}$=—H, —CH$_3$, —CH$_2$CH$_3$, —NH$_2$ or —NHCH$_3$, wherein $R_{29}$=—H, —OH, —SH, —CONH$_2$ or —CONHCH$_3$, wherein $R_{30}$=—H, —CH$_3$, —CH$_2$CH$_3$, —NH$_2$ or —NHCH$_3$ and wherein $R_{31}$=—H, —CH$_3$, —CH$_2$CH$_3$, —NH$_2$ or —NHCH$_3$, and 3) one or more members selected from the group consisting of 2-amino-4-chloro-6-methyl-pyrimidine, 1,3-benzothiazole-2-thiol, 4-amino-N-1,3-thiazol-2-ylbenzenesulfonamide, thiourea, 2,4-diamino-6-trichloromethyl-5-triazine, 4-amino-1,2,4-triazole, 3-mercapto-1,2,4-triazole, and 2,3-dihydro-2,2-dimethyl-7-benzofuranol methyl-carbamate.

15. The composition of claim 9, wherein the composition further comprises one or more members selected from the group consisting of surfactants, buffers, fragrance/odor masking agents, colorants, flow modifiers, silicas, and hydrophobized silicas.

16. The composition of claim 9, wherein the composition further comprises one or more members selected from the group consisting of:
  i. one or more biologics selected from the group consisting of:
  i) *Bacillus* biologics, ii) *Azospirillum* biologics, iii) *Azobacter* biologics iv) *Gluconacetobacter* biologics, v) *Phosphobacteria*, vi) *Cyanobacteria*, vii) *Herbaspirillum*, viii) *Burkholderia*, ix) *Pseudomonas*, x) *Gluconacetobacter*, xi) *Enterobacter*, xii) *Klebsiella*, xiii) *Burkholderia*, xiv) *Bradyrhiwbium* species, xv) *Bradyrhiwbium japonicum*, xvi) *Rhizobium meliloti*, xvii) *Laccaria bicolor*, xviii) *Glomus imraradices timanita*, xix) *Actinomyces*, xx) *Penicillium*, xxi) *Mesorhizobiwn cicero*, xxii) one or more insecticidal or insect repellent microbial species and strains selected from the group consisting of:
    *Telenomus podisi, Baculovirus anticarsia; Trichogramma pretiosum, Trichogramma gallai, Chromobacterium subtsugae, Trichoderma fertile, Beauveria bassiana, Beauveria bassiana, Beauveria bassiana, Paecilomyces jknwsoroseu, Trichoderma harzianum, Verticillium lecanii, lsarfofumosarosea Lecanicillium muscarium, Streptomyces microflavus,* and *Muscodor albus,*
  xxiii) one or more nematodal microbial species and strains selected from the group consisting of:
    *Myrothecium verrucaria, Pasteuria* species, *Pasteuria Metarhizium* species and *Flavobacteriwn* species
  xxiv) *Reynoutria sachalinensis* and
  xxv) one or more antifungal, antimicrobial and/or plant growth promoting microbial species and strains selected from the group consisting of:
    *Gliocladium* species, *Pseudomonas* species selected from the group consisting of:
      *Pseudomonas fluorescens, Pseudomonas fluorescens. putida* and *P. chlororaphis, Pseudomonasfluorescens* VP5, *Pseudomonas diazotrophicus, Enterobacter cloacae, Trichodema species, Trichoderma virens, Trichoderma atroviride* strains, *Coniothyrium minitans, Gliocladium* species, *Gliacladium vixens, Gliacladium roseum,* and *Trichodemw harzianum* species,
  ii. and one or more biologically active agents selected from the group consisting of:
  i) one or more urease inhibitors selected from the group consisting of aliphatic phosphoric triamide, phosphoramides, N-alkyl thiophosphoric triamides, (aminomethyl)phosphinic acids and their salts and aminomethyl (alkylaminomethyl)phosphinic acids and their salts,
  ii) one or more nitrification inhibitors selected from the group consisting of 2-chloro-6-trichloromethyl)pyridine, 4-amino-1,2,4,6-triazole-HCl, 2,4-diamino-6-trichloromethyltriazine CL-1580, dicyandiamide (DCD), thiourea, 1-mercapto-1,2,4-triazole, ammonium thiosulfate, dimethylpyrazole organic and inorganic salts, and 2-amino-4-chloro-6-methylpyrimidine,
  iii) and pesticides, herbicides, fungicides(s), and insecticide(s).

17. The composition of claim 9, wherein the composition further comprises one or more organo polyorganic acids and/or their salts, wherein the organo polyorganic acids and/or their salts is a monomer homopolymer, a copolymer and/or a terpolymer and is one or more members selected from the group consisting of:

aspartic acid, glutamic acid, maleic anhydride, itaconic anhydride, citraconic anhydride, citric acid, and acrylic acid, wherein the organo polyorganic acids are present in an amount that is about 5-50% of a total composition and wherein a cation of salts of the polyacids comprise one or more members selected from the group consisting of one or more metals and one or more organoamines wherein the one or more metals are selected from the group consisting of Na, K, Mg, Ca, Fe, Zn, Mn, Cu, Co, Mo, and Ni and wherein the one or more organoamines are selected from the group consisting of mono $C_{1-6}$ amine, di $C_{1-6}$ amine, tri $C_{1-6}$ amine, mono ethanol amine, diethanol amine, triethanol amine, monoisopropyl amine, diisopropyl amine, triisopropyl amine, and diethyl amine.

18. The composition of claim 9, wherein said treated urea is comprising urea and one or more members selected from the group consisting of a) urea formaldehyde polymer, b) urea formaldehyde reaction adducts, c) one or more biologics d) one or more biologically active agents and e) organo polyorganic acids and/or their salts wherein the one or more biologics are selected from the group consisting of:
  i) *Bacillus* biologics, ii) *Azospirillum* biologics, iii) *Azobacter* biologics iv) *Gluconacetobacter* biologics, v) *Phosphobacteria*, vi) *Cyanobacteria*, vii) *Herbaspirillum*, viii) *Burkholderia*, ix) *Pseudomonas*, x) *Gluconacetobacter*, xi) *Enterobacter*, xii) *Klebsiella*, xiii) *Burkholderia*, xiv) *Bradyrhiwbium* species, xv) *Bradyrhiwbium japonicum*, xvi) *Rhizobium meliloti*, xvii) *Laccaria bicolor*, xviii) *Glomus imraradices timanita*, xix) *Actinomyces*, xx) *Penicillium*, xxi) *Mesorhizobiwn cicero*, xxii) one or more insecticidal or insect repellent microbial species and strains selected from the group consisting of:
    *Telenomus podisi, Baculovirus anticarsia; Trichogramma pretiosum, Trichogramma gallai, Chromobacterium subtsugae, Trichoderma fertile, Beauveria bassiana, Beauveria bassiana, Beauveria bassiana, Paecilomyces jknwsoroseu, Trichoderma harzianum, Verticillium lecanii, lsarfofumosarosea*

*Lecanicillium muscarium, Streptomyces microflavus,* and *Muscodor albus,* xxiii) one or more nematodal microbial species and strains selected from the group consisting of:

*Myrothecium verrucaria, Pasteuria* species, *Pasteuria Metarhizium* species, and *Flavobacteriwn* species xxiv) *Reynoutria sachalinensis* and xxv) one or more antifungal, antimicrobial and/or plant growth promoting microbial species and strains selected from the group consisting of:

*Gliocladium* species, *Pseudomonas* species selected from the group consisting of:

*Pseudomonas fluorescens, Pseudomonas fluorescens. putida* and *P. chlororaphis, Pseudomonasfluorescens* VP5, *Pseudomonas diazotrophicus, Enterobacter cloacae, Trichodema species, Trichoderma virens, Trichoderma atroviride* strains, *Coniothyrium minitans, Gliocladium* species, *Gliacladium virens, Gliacladium roseum, Trichodemw harzianum* species, and wherein said one or more biologically active agents are selected from the group consisting of:

i) one or more urease inhibitors selected from the group consisting of aliphatic phosphoric triamide, phosphoramides, N-alkyl thiophosphoric triamides, (aminomethyl)phosphinic acids and their salts and aminomethyl (alkylaminomethyl)phosphinic acids and their salts, ii) one or more nitrification inhibitors selected from the group consisting of 2-chloro-6-trichloromethyl)pyridine, 4-amino-1,2,4,6-triazole-HCl, 2,4-diamino-6-trichloromethyltriazine CL-1580, dicyandiamide (DCD), thiourea, 1-mercapto-1,2,4-triazole, ammonium thiosulfate, dimethylpyrazole organic and inorganic salts, and 2-amino-4-chloro-6-methylpyrimidine, iii) and one or more members selected from the group consisting of pesticides, herbicides, fungicides(s), and insecticide(s).

19. The composition of claim 9, wherein the composition of the nitrogen source comprises urea.

20. The composition of claim 9, wherein the composition of the nitrogen source comprises ammonia.

* * * * *